(12) United States Patent
Bikram

(10) Patent No.: US 8,323,618 B2
(45) Date of Patent: *Dec. 4, 2012

(54) ULTRASMALL SUPERPARAMAGNETIC IRON OXIDE NANOPARTICLES AND USES THEREOF

(75) Inventor: Malavosklish Bikram, Spring, TX (US)

(73) Assignee: University of Houston System, Houston, TX (US)

( * ) Notice: Subject to any disclaimer, the term of this patent is extended or adjusted under 35 U.S.C. 154(b) by 831 days.

This patent is subject to a terminal disclaimer.

(21) Appl. No.: 12/378,100

(22) Filed: Feb. 11, 2009

(65) Prior Publication Data

US 2010/0003197 A1    Jan. 7, 2010

Related U.S. Application Data

(63) Continuation-in-part of application No. 12/291,195, filed on Nov. 7, 2008, now Pat. No. 8,147,803.

(60) Provisional application No. 61/002,201, filed on Nov. 7, 2007.

(51) Int. Cl.
*A61K 49/06* (2006.01)

(52) U.S. Cl. ............. 424/9.323; 424/9.1; 424/9.32; 428/402; 428/403

(58) Field of Classification Search .......... 424/9.1, 424/9.32, 9.34, 486; 428/402, 403, 263, 428/632

See application file for complete search history.

(56) References Cited

U.S. PATENT DOCUMENTS

| 6,514,481 | B1 * | 2/2003 | Prasad et al. | 424/9.32 |
| 7,504,082 | B2 * | 3/2009 | Cho et al. | 423/263 |
| 2005/0025969 | A1 * | 2/2005 | Berning et al. | 428/403 |
| 2006/0228551 | A1 * | 10/2006 | Chen et al. | 428/402 |
| 2007/0190551 | A1 * | 8/2007 | Mirkin et al. | 435/6 |

OTHER PUBLICATIONS

Jun-Hyun Kim, William W. Bryan and T Randall Lee, Preparation, Characterization, and Optical Properties of Gold, Silver, and Gold-Silver Allowy Nanoshells Having Silica Cores, Langmuir 2008, 11147-11152.*

* cited by examiner

*Primary Examiner* — Michael G Hartley
*Assistant Examiner* — Jagadishwar Samala
(74) *Attorney, Agent, or Firm* — Benjamin Aaron Adler

(57) ABSTRACT

The present invention provides biomimetic contrast agents, dual functional contrast agents effective for therapeutic gene delivery and magnetic nanoparticles which comprise functionalized iron oxide nanoparticle cores, one of an inert gold layer, a layer of inert metal seeds or a silica layer and, optionally, one or both of an outer gold-silver nanoshell or a targeting ligand attached to the inert gold layer or the gold-silver nanoshell. Also provided are methods of in vivo magnetic resonance imaging, of treating primary or metastatic cancers or of ablating atherosclerotic plaque using the contrast agents and magnetic particles. In addition, kits comprising the biomimetic contrast agents, dual contrast agents and magnetic nanoparticles.

17 Claims, 32 Drawing Sheets

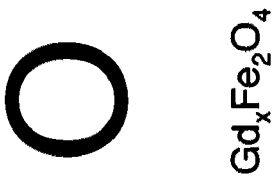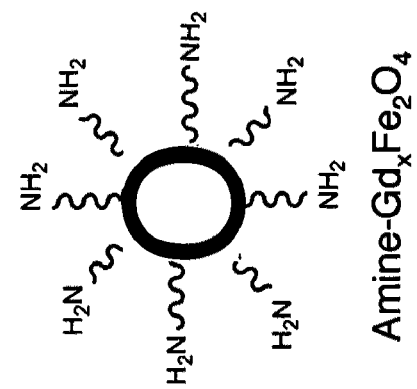
$FeCl_2 \cdot 4H_2O + FeCl_3 \cdot 6H_2O + GdCl_3$ $\xrightarrow[N_2(g)]{1.5\ M\ NaOH,\ pH\ 12}$ $Gd_xFe_2O_4$
Fig. 1A
$Gd_xFe_2O_4$ $\xrightarrow[\text{3-aminopropyltrimethoxysilane (APTMS)}]{\text{Conc. } NH_4OH,\ pH\ 11\text{-}12,\ N_2(g)}$ Amine-$Gd_xFe_2O_4$
Fig. 1B

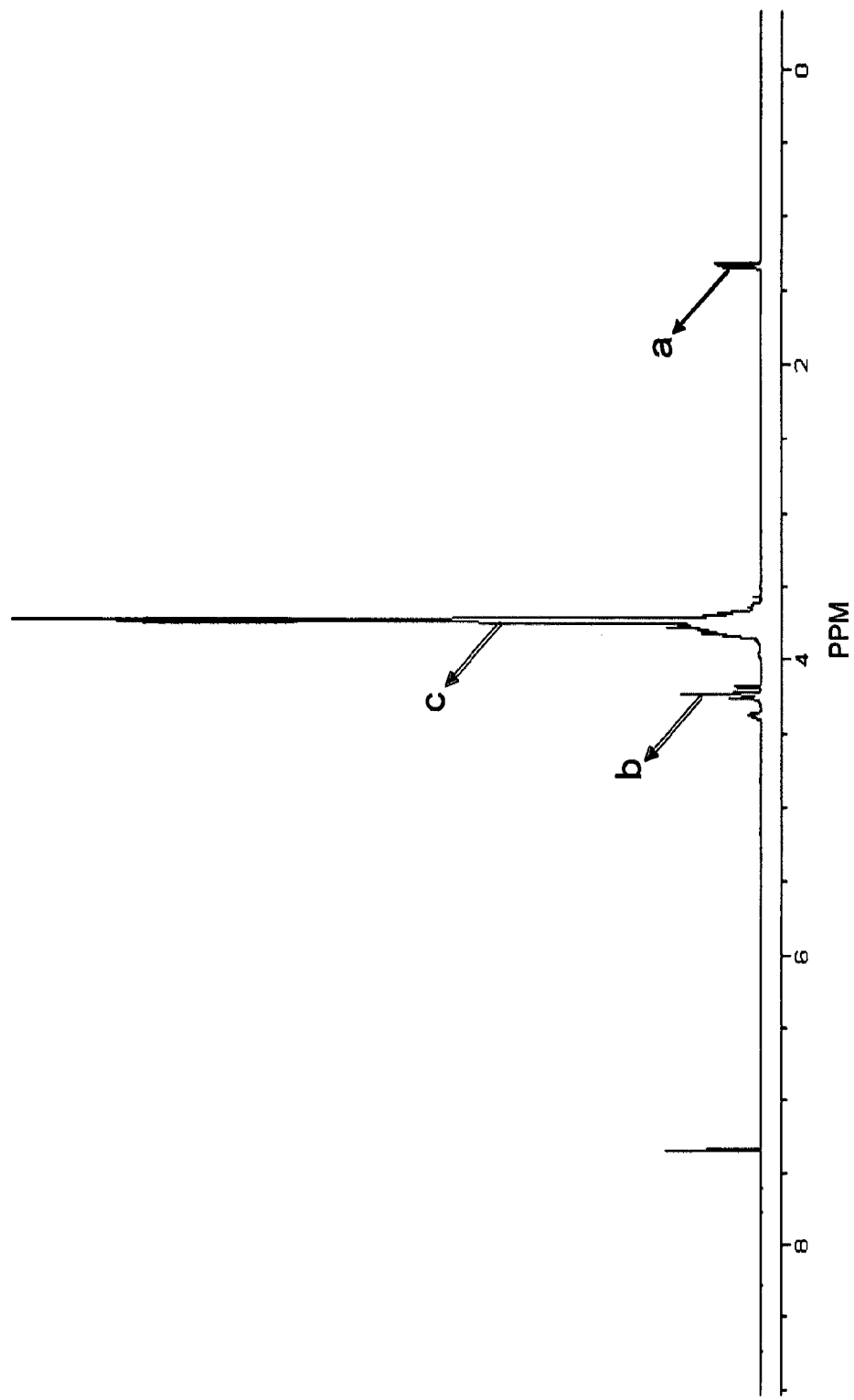

$2FeCl_3(aq) + FeCl_2(aq) + 8NH_4OH \rightarrow Fe_3O_4 + 8NH_4CL + 4H_2O$ $3 H_2C=O + 2NaAuCl_4 + 6H_2O \rightarrow 3CH_3OH + 2Au + 2NaCl + 6HCl$

SEQUENCE LISTING

```
<160> NUMBER OF SEQ ID NOS: 7

<210> SEQ ID NO 1
<211> LENGTH: 5
<212> TYPE: PRT
<213> ORGANISM: Artificial Sequence
<220> FEATURE:
<223> OTHER INFORMATION: peptide sequence cleavable by
      metalloproteinase-13 enzyme (MMP-13)

<400> SEQUENCE: 1

Pro Gln Gly Leu Ala
1               5

<210> SEQ ID NO 2
<211> LENGTH: 21
<212> TYPE: PRT
<213> ORGANISM: Artificial Sequence
<220> FEATURE:
<223> OTHER INFORMATION: an endothelin-1 (ET-1) peptide sequence

<400> SEQUENCE: 2

Cys Ser Cys Ser Ser Leu Met Asp Lys Glu Cys Val Tyr Phe Cys
1               5                   10                  15

His Leu Asp Ile Ile Trp
                20

<210> SEQ ID NO 3
<211> LENGTH: 4
<212> TYPE: PRT
<213> ORGANISM: Artificial Sequence
<220> FEATURE:
<223> OTHER INFORMATION: an integrin binding peptide sequence

<400> SEQUENCE: 3

Arg Gly Asp Ser
1

<210> SEQ ID NO 4
<211> LENGTH: 11
<212> TYPE: PRT
<213> ORGANISM: Artificial Sequence
<220> FEATURE:
<223> OTHER INFORMATION: a human immunobinding virus (HIV) Tat peptide
      sequence

<400> SEQUENCE: 4

Tyr Gly Arg Lys Lys Arg Arg Gln Arg Arg Arg
1               5                   10

<210> SEQ ID NO 5
<211> LENGTH: 29
<212> TYPE: PRT
<213> ORGANISM: Artificial Sequence
<220> FEATURE:
<223> OTHER INFORMATION: contiguous targeting ligand sequence  of the
```

```
                     ET-1 peptide, the MMP-13 cleavable peptide
                     and glycine spacers at positions 1, 23 and 29

<400> SEQUENCE: 5

Gly Cys Ser Cys Ser Ser Leu Met Asp Lys Glu Cys Val Tyr Phe
1               5                   10                  15

Cys His Leu Asp Ile Ile Trp Gly Pro Gln Gly Leu Ala Gly
                20                  25

<210> SEQ ID NO 6
<211> LENGTH: 12
<212> TYPE: PRT
<213> ORGANISM: Artificial Sequence
<220> FEATURE:
<223> OTHER INFORMATION: contiguous targeting ligand sequence  of the
      integrin binding peptide, the MMP-13 cleavable peptide
      and glycine spacers at positions 1, 6 and 12

<400> SEQUENCE: 6

Gly Arg Gly Asp Ser Gly Pro Gln Gly Leu Ala Gly
1               5                   10

<210> SEQ ID NO 7
<211> LENGTH: 19
<212> TYPE: PRT
<213> ORGANISM: Artificial Sequence
<220> FEATURE:
<223> OTHER INFORMATION: contiguous targeting ligand sequence  of the
      HIV Tat peptide, the MMP-13 cleavable peptide
      and glycine spacers at positions 1, 6 and 12

<400> SEQUENCE: 7

Gly Tyr Gly Arg Lys Lys Arg Arg Gln Arg Arg Arg Gly Pro Gln
1               5                   10                  15

Gly Leu Ala Gly
```

ULTRASMALL SUPERPARAMAGNETIC IRON OXIDE NANOPARTICLES AND USES THEREOF

CROSS-REFERENCE TO RELATED APPLICATION

This is a continuation-in-part of non-provisional application U.S. Ser. No. 12/291,195, filed Nov. 7, 2008 now U.S. Pat. No. 8,147,803, which claims benefit of provisional application U.S. Ser. No. 61/002,201 filed on Nov. 7, 2007, the entirety of which is hereby incorporated by reference.

FIELD OF THE INVENTION

The present invention relates to the fields of magnetic resonance imaging and contrast agents and disease diagnosis and treatment. More specifically, the invention relates to iron oxide nanoparticles that are either doped or not doped with varying amounts of metal ions and, optionally, gold-coated, and are surface-modified with a biomimetic and bioresponsive entity that imparts specificity of the contrast agent, which may include delivery of a therapeutic gene or drug, to the desired target.

DESCRIPTION OF THE RELATED ART

In recent years, magnetic nanoparticles (MNPs) have generated significant interest within the scientific community due to their huge range of potential applications such as media materials for storage systems (1-2), biotechnology (3-4), magnetic separation (5-6) targeted drug delivery (7-8) and vehicles for gene and drug delivery (9-12). Among the various MNPs, undoped and transition metal-doped, e.g., Magnetite or Maghemite, iron oxide nanoparticles, $Fe_3O_4$, $\gamma$-$Fe_2O_3$ and $M_xFe_yO_z$ have found many applications in the area of biomedical diagnostics and therapy.

In the field of imaging, the superparamagnetic nature of iron oxide nanoparticles enables their use as potential contrast agents for magnetic resonance imaging (MRI). These nanoparticles with very large magnetic susceptibilities strongly influence the $T_1$ and $T_2$ relaxation of water molecules surrounding these MRI contrast agents. In addition, the magnetic properties of these iron oxide nanoparticles are also dependent on particle size. Iron oxide nanoparticles that are below 15-20 nm retain superparamagnetism and influence the $T_2$ relaxation to the largest extent (13-14). This influence on the $T_2$ relaxation highly modulates the MRI properties of the iron oxide nanoparticles. Hence, by adjusting the core size of the nanoparticles the magnetic properties for MRI can be enhanced. Typically, MNPs are synthesized with a particle size of 10-500 nm in diameter for biomedical applications.

In addition to size, the biocompatibility, solubility, and monodispersity of these MNPs are also critical for their use in vivo (15). However, the surface-chemical properties of MNPs do not facilitate the conjugation of biomolecules. Therefore, the surface of these MNPs must undergo modification or functionalization to enable the chemistry needed for coupling biomolecules to MNPs. In other words, in order to make the magnetic nanoparticles efficient delivery vehicles, introduction of suitable functional groups onto the surface of the particle is essential so as to facilitate the conjugation of molecules that will increase its solubility and increase its availability for various conjugation processes. Also, the conjugation process has to be efficient, yielding a stable product, which does not compromise the activity of the biomolecules. Moreover, the signal of the nanoparticles for imaging or other analytical techniques should not be affected as a result of the conjugation. In addition, these nanoparticles should also have maximum surface area so as to facilitate the binding of a maximum number of linkage sites on the surface.

In the United States, breast cancer is second to lung cancer as the leading cause of cancer death in women. This year alone, ~40,000 women will die from the disease despite a decline in the death rates. Detection is the best method to prevent mortality but only 60% of cancers are detected at the earliest, subclinical stages of the disease. Also, ovarian cancer has the highest mortality rate of all gynecological malignancies. Poor prognosis of the disease is directly related to late detection after peritoneal tumor dissemination and the formation of ascites. Failure to detect early primary tumors or metastases results in very poor clinical outcome.

MRI is a powerful imaging modality for detection of cancer and other diseases because it provides high spatial resolution and excellent soft tissue contrast. However, MRI imaging systems need to be developed that are sensitive enough to detect cancers in the early stage of development and to detect metastatic cancers.

Thus, there is a recognized need in the art for improved contrast agents effective to detect early stage primary and metastatic cancers via magnetic resonance imaging, including contrast agents suitable to deliver a therapeutic gene or drug during imaging, and for tunable magnetic nanoparticles having thermolytic properties. More specifically, the prior art is deficient in biomimetic contrast agents and a dual functioning contrast agent/gene/drug delivery system effective to specifically target primary and metastatic cancer cells with MRI. The present invention fulfills this long-standing need and desire in the art.

SUMMARY OF THE INVENTION

The present invention is directed to a biomimetic contrast agent. The contrast agent comprises an amine-functionalized iron (II) oxide/iron(III) oxide nanoparticle core, a targeting ligand attached to the nanoparticle core via a linker and an inert outer layer of a hydrophilic polymer conjugated to the targeting ligand. The present invention is directed to a related biometric contrast agent further comprising a metal doping agent in the nanoparticle. core. The present invention is directed to another related biometric contrast agent further comprising a gold coating on the nanoparticle core.

The present invention also is directed to a dual contrast agent that comprises a metal-doped iron (II) oxide/iron(III) oxide nanoparticle core, an inert layer of gold coating the nanoparticle core and a biodegradable cationic polymer linked thereto. The present invention is directed to a related contrast agent further comprising a DNA encoding an antitumor cytokine complexed with the cationic polymer.

The present invention is directed further still to a kit comprising the biomimetic contrast agent described herein. The present invention is directed further still to a kit comprising the dual contrast agent described herein or the dual contrast agent complexed to a DNA encoding a therapeutic gene described herein. The present invention is directed to a related kit further comprising the buffers and reagents effective to transfect mesenchymal stem cells with the contrast agent-DNA complex.

The present invention is directed further still to a dual contrast agent and gene delivery system. The system comprises mesenchymal stem cells (MSCs) transfected with the dual contrast agent of described herein complexed with a DNA encoding an anti-tumor cytokine.

The present invention is directed further still to an in vivo method using magnetic resonance imaging for detecting an early stage primary or metastatic cancer in a subject. The method comprises administering to the subject a sufficient amount of the biomimetic contrast agent described herein to provide a detectable contrast image of the contrast agent within the primary or metastatic cancer therein, wherein a location of the image correlates to a location of the cancer.

The present invention is directed further still to a method for reducing metastasis of tumor cells in a subject. The method comprises administering to the subject an amount of the mesenchymal stem cells (MSCs) comprising the dual contrast agent and gene delivery system described herein sufficient to target metastatic tumor cells and simultaneously delivering the contrast agent and the anti-tumor cytokine thereto. A magnetic resonance image of the contrast agent within the metastatic tumor cells is obtained; where simultaneously imaging the contrast agent and delivering the anti-tumor cytokine locates a site of metastatic tumor cells and induces a pro-inflammatory response against the same, thereby reducing metastasis of the tumor cells. The present invention is directed to a related method further comprising implementing one or both of a surgical regimen or one or more other chemotherapeutic regimens.

The present invention is directed further still to a magnetic nanoparticle. The magnetic nanoparticle comprises an inner functionalized iron oxide core, an inert metal seeding the functionalized core and an outer inert metal alloy nanoshell. The present invention is directed to a related magnetic nanoparticle further comprising a metal-doping agent in the nanoparticle core. The present invention is directed to another related magnetic nanoparticle further comprising a targeting ligand attached to the nanoshell via a linker. A related invention is directed to a kit comprising the magnetic nanoparticles described herein.

The present invention is directed to a related magnetic nanoparticle comprising an amine-functionalized metal-doped iron(III) oxide core, a layer of gold seeding the amine-functionalized metal-doped iron oxide core, an outer gold-silver alloy nanoshell, and a targeting ligand attached to the nanoshell via a linker. The present invention is directed to another related magnetic nanoparticle comprising an iron(III) oxide/iron(II) core, a layer silica around the core, an outer gold-silver alloy nanoshell, and a targeting ligand attached to the nanoshell via a linker.

The present invention is directed further still to an in vivo method using magnetic resonance imaging for detecting an early stage primary or metastatic cancer in a subject. The method comprises administering to the subject a sufficient amount of the magnetic nanoparticles described herein to provide a detectable contrast image of the magnetic nanoparticles within the primary or metastatic cancer therein where a location of the image correlates to a location of the cancer. The present invention is directed to a related method further comprising irradiating the magnetic nanoparticles with a near infrared wavelength to generate heat therewithin effective to ablate the primary or metastatic cancer.

The present invention is directed further still to a method for treating metastatic or primary cancer in a subject. The method comprises administering the magnetic nanoparticles described herein to the subject to target one or both of the metastatic or primary cancers. The magnetic nanoparticles are irradiated with a near infrared wavelength effective to heat the same where the heated nanoparticles cause thermolysis of cells comprising the cancer(s) thereby treating the metastatic or primary cancer in the subject.

The present invention is directed further still to a method for ablating atherosclerotic plaque in a subject. The method comprises administering the magnetic nanoparticles described herein to the subject to target vascular tissues having atherosclerotic plaque therein. The magnetic nanoparticles are irradiated with a near infrared wavelength effective to heat the same; where the heated nanoparticles ablate the atherosclerotic plaque in the subject.

Other and further aspects, features and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention are briefly summarized. The above may be better understood by reference to certain embodiments thereof which are illustrated in the appended drawings. These drawings form a part of the specification. It is to be noted; however, that the appended drawings illustrate preferred embodiments of the invention and therefore are not to be considered limiting in their scope.

FIGS. 1A-1B depict the syntheses of Gadolinium-doped Ultrasmall Paramagnetic Iron Oxide Nanoparticles (GdUSPIO) (FIG. 1B) and amine-functionalized Gadolinium-doped Ultrasmall Paramagnetic Iron Oxide Nanoparticles (amine-GdUSPIO) (FIG. 1B).

FIGS. 6A-6E depict the $^1$H NMR spectra of homobifunctional COOH-PEG400-COOH diacid (b), the HPLC spectra for separation of bioresponsive peptide with the RGDS (GRGDSGPQGLAG; SEQ ID NO: 6) ligand on an analytical column (b) and a preparative column showing the main peaks of interest at 25 and 19 min (FIG. 6C) along with smaller peaks representing byproducts of the synthesis reaction, the $^1$H NMR spectrum of synthesized COOH-PEG$_{2000}$-OMe outer stealth layer showing proton peaks of the polymer (FIG. 6D), the relaxivities for ultra small paramagnetic iron oxide nanoparticles (r=130.8 mMol/lsec), amine-functionalized ultra small paramagnetic iron oxide nanoparticles (r=5.5 mMol/lsec) and internal control CuSO$_4$ (r=1.2 mMol/lsec) (FIG. 6E).

Figure 8A:
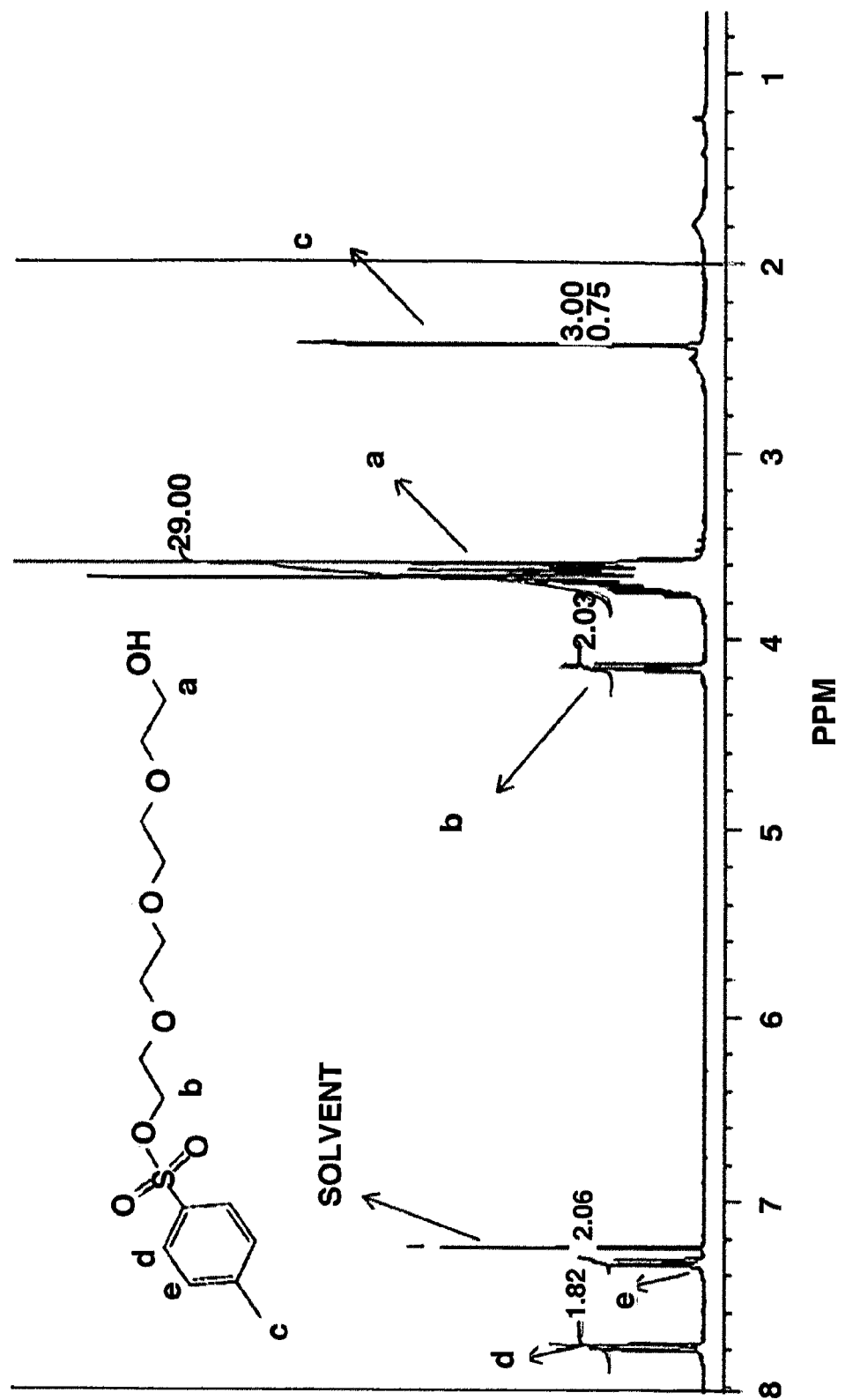
Figure 8B:
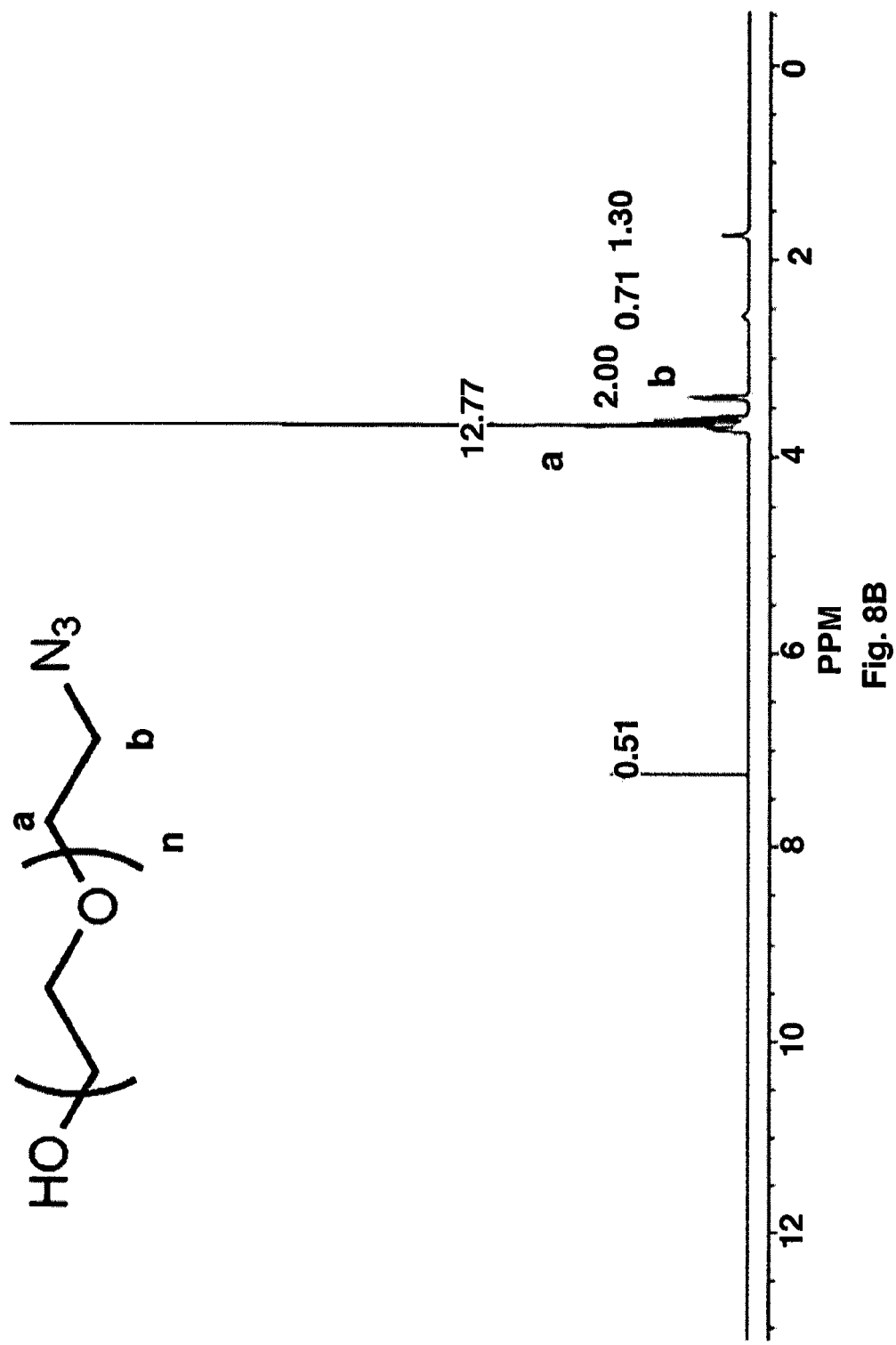
Figure 8C:
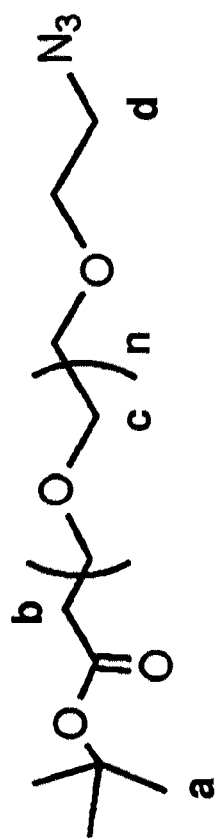
Figure 8C:
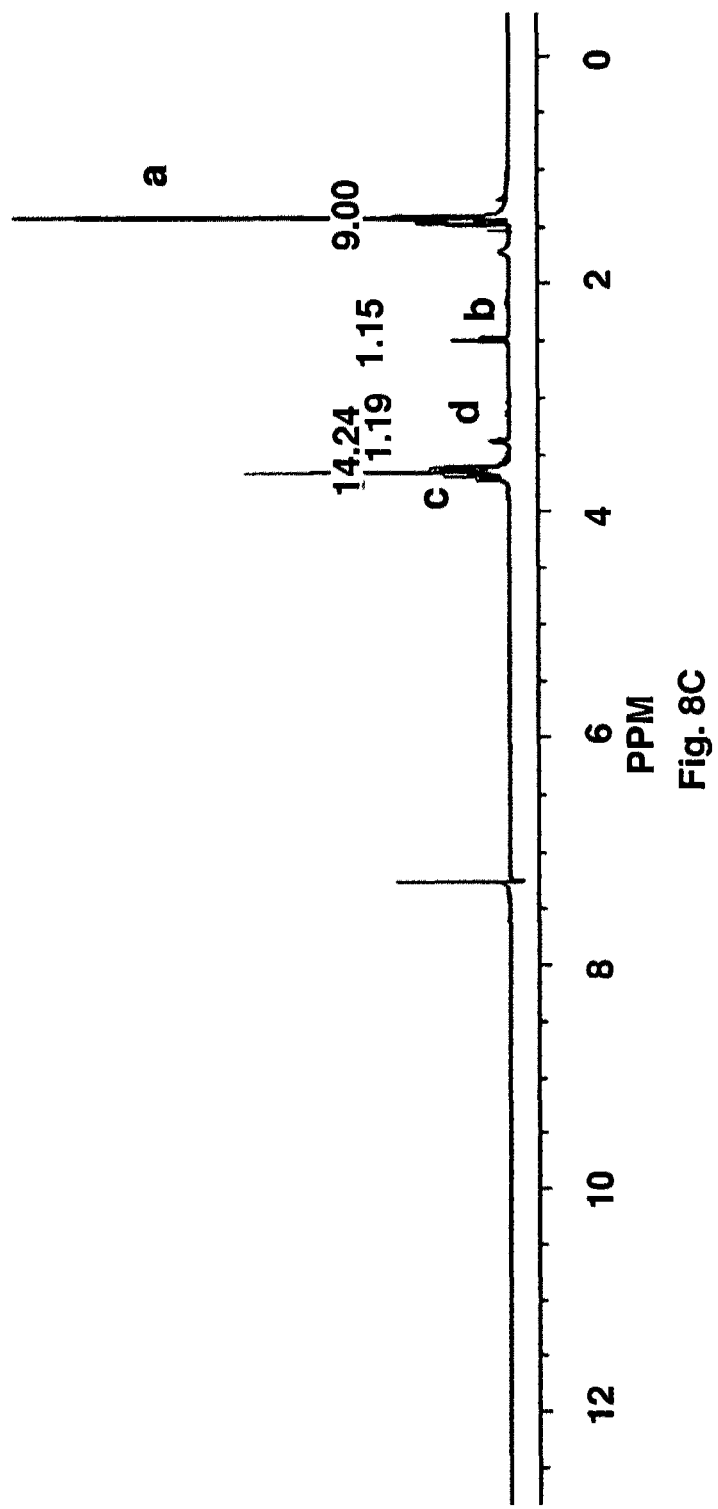
Figure 8D:
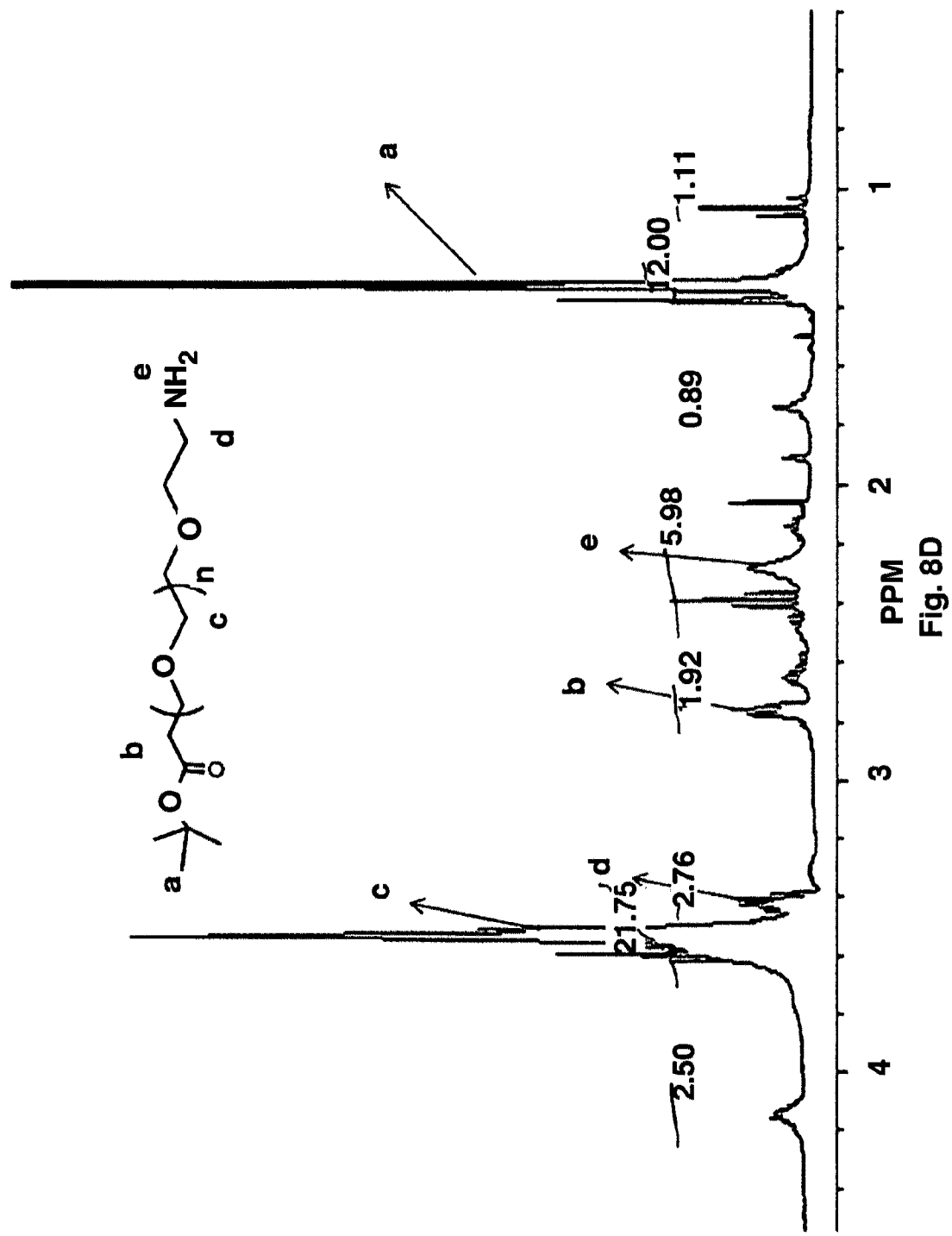
Figure 8E:
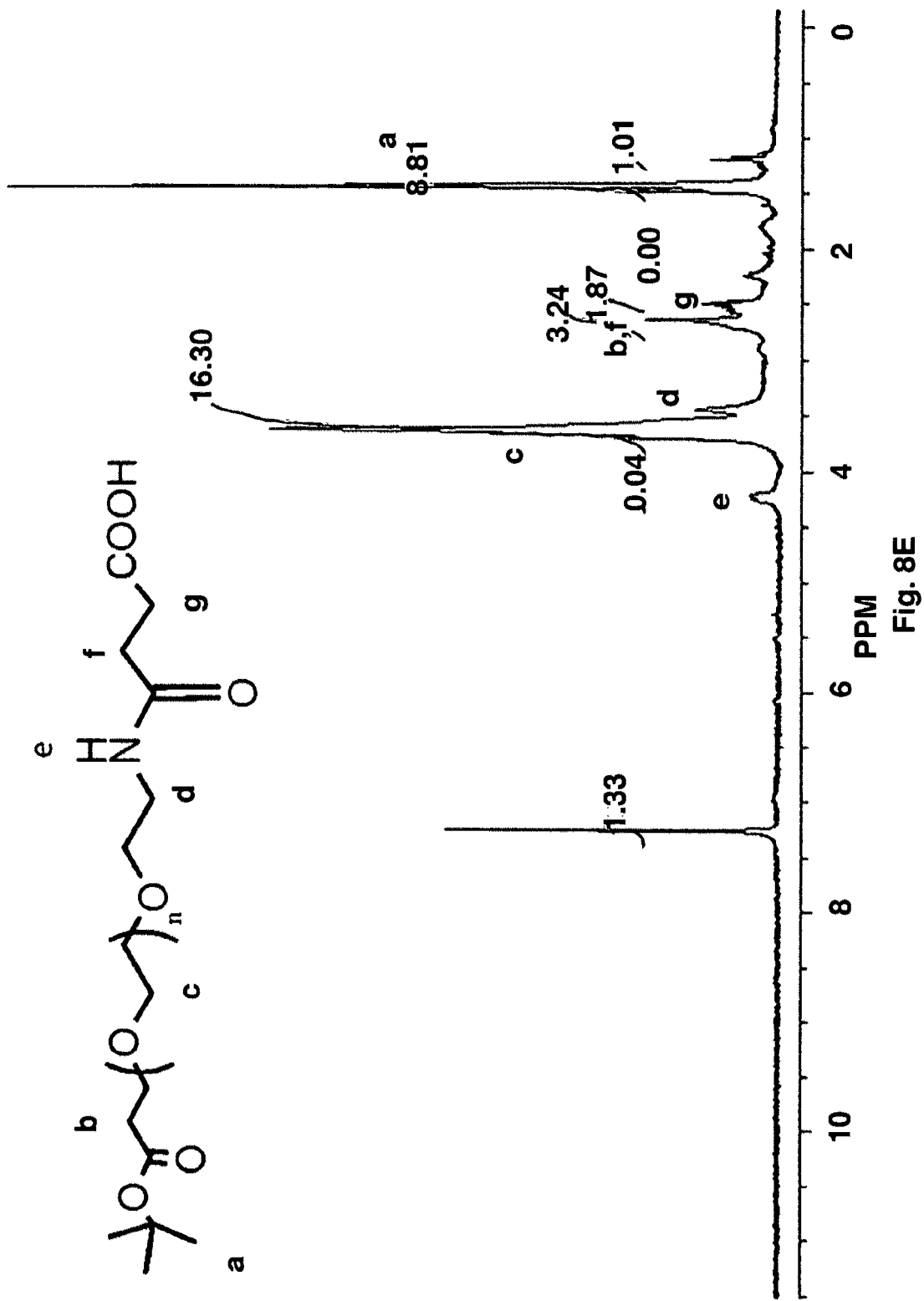
Figure 8F:
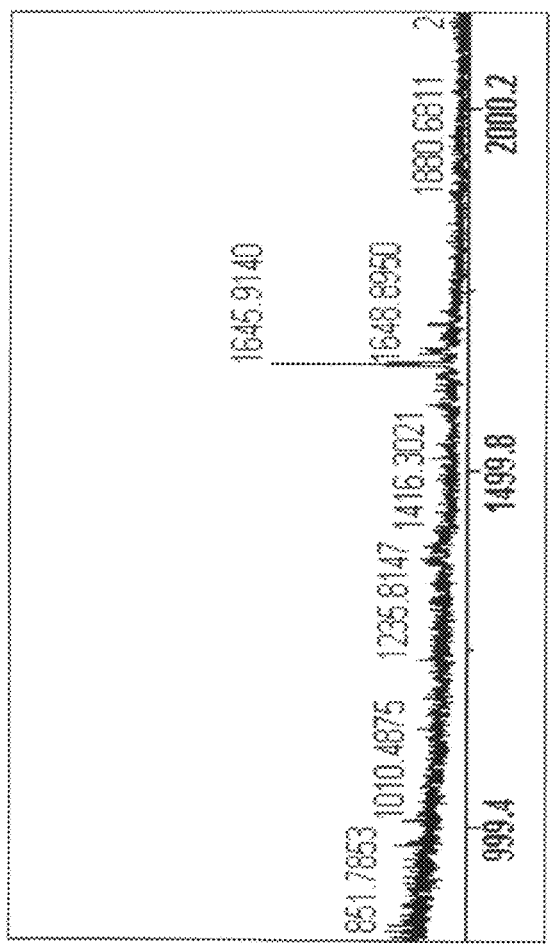

FIGS. 8A-8F depict the NMR spectra of OH-TEG-Ots (FIG. 8A), OH-TEG-N$_3$ (FIG. 8B), t-butyl ester-TEG-N$_3$ (FIG. 8C), NH$_2$-TEG-t-butylester (FIG. 8D), t-butylester-TEG-COOH (FIG. 8E), and the MALDI-TOF data for dual bioresponsive peptide (FIG. 8F).

Figure 9:
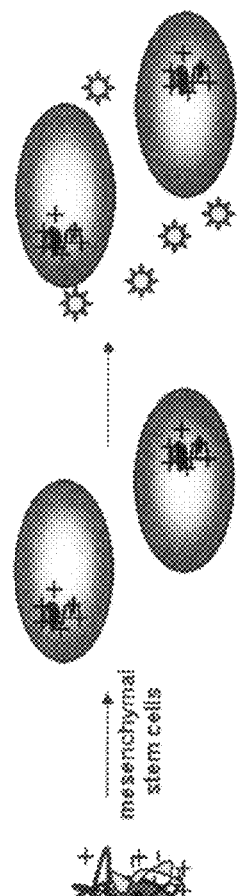

FIG. 9 is a schematic representation of IL-12 protein from nanoparticle-transfected MSCs homing to tumor cells.

Figure 10A:
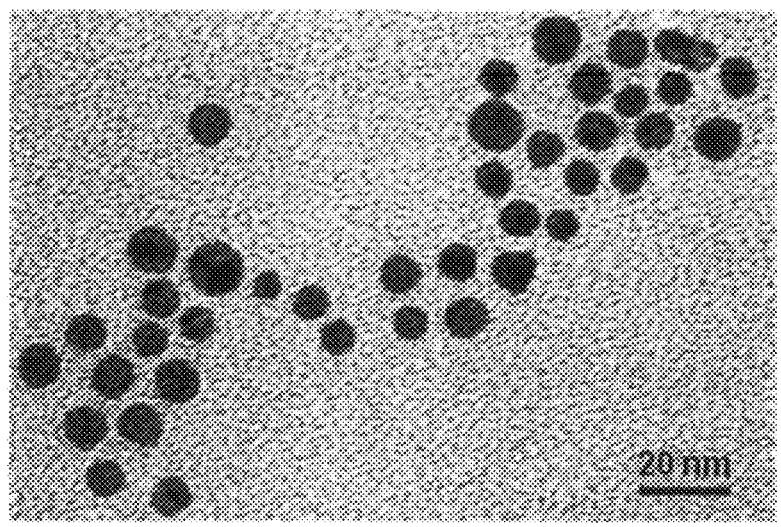
Figure 10B:
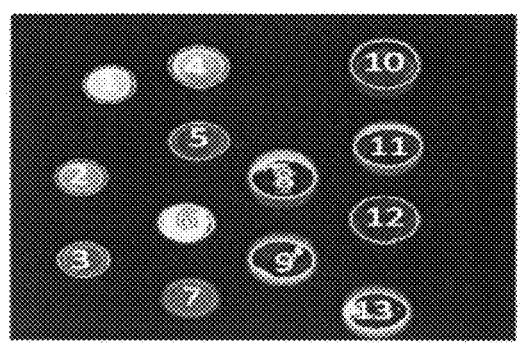

FIGS. 10A-10B depict the TEM image of synthesized Au-coated 4% Gd[III]-doped iron oxide nanoparticles where scale=20 nm (FIG. 10A) and the MRI images of new contrast agents; Samples 1-7=CuSO$_4$; 8-9=4%, 10-11=0%, and 12-13=2% iron oxide-doped Gd nanoparticles (FIG. 10B).

Figure 11:
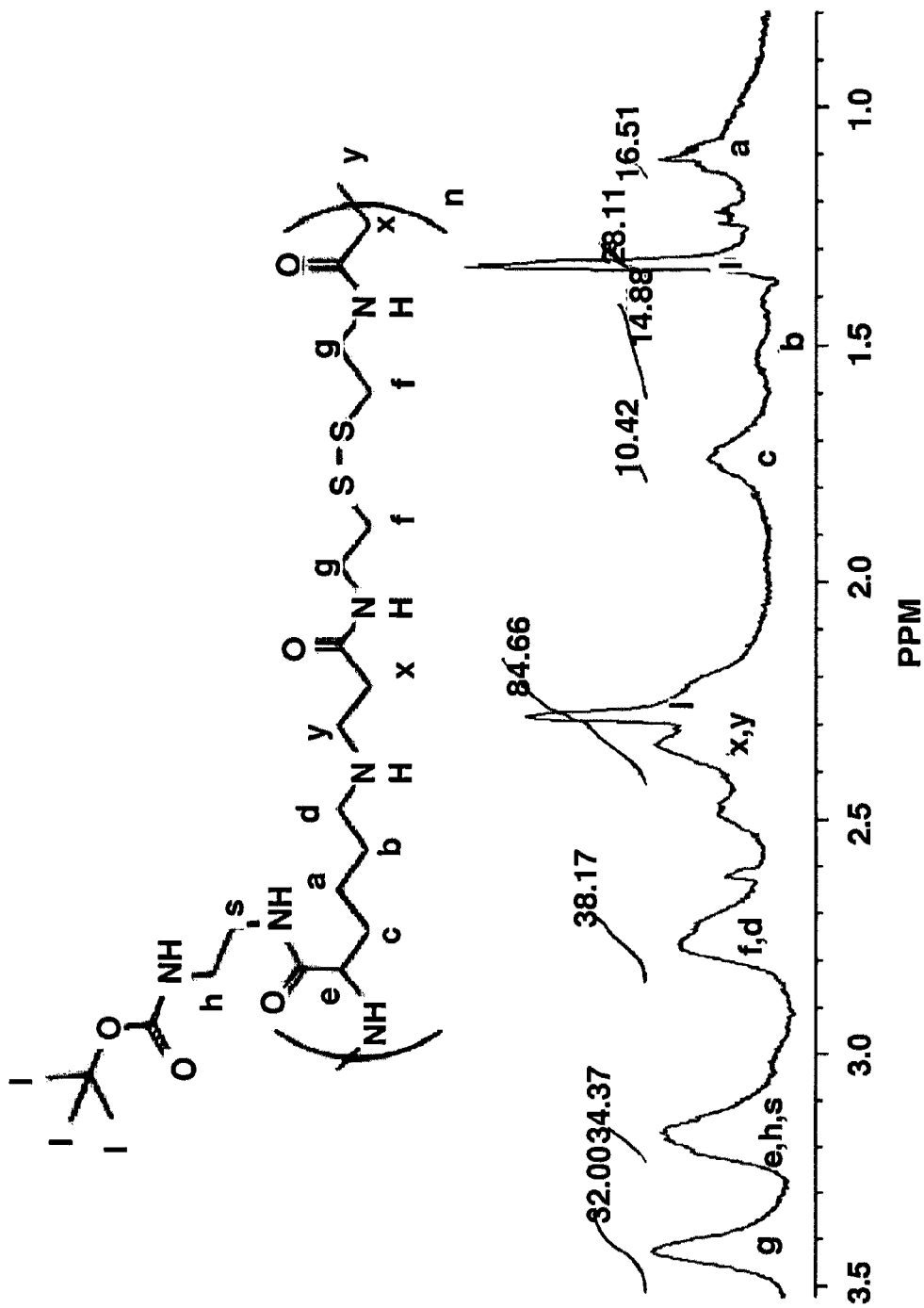

FIG. 11 depicts the $^1$H NMR spectrum of synthesized reducible LLC-N-boc conjugated polymers.

Figure 12:
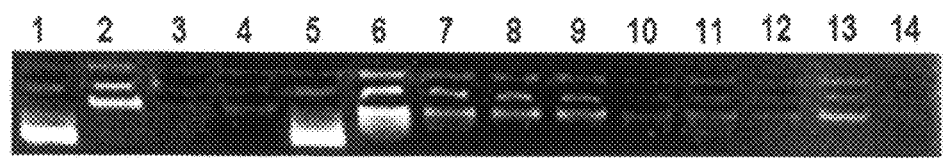

FIG. 12 depicts the gel retardation assay of deprotected reducible LLC coplymers: 1=free DNA; 2=linear PEI; 3=branched PEI; 4=PLL; 5=1/1; 6=5/1; 7=10/1; 8=15/1; 9=20/1; 10=25/1; 11=30/1; 12=40/1; 13=50/1; and 14=100/1 N/P ratios.

Figure 13A:
Figure 13B:
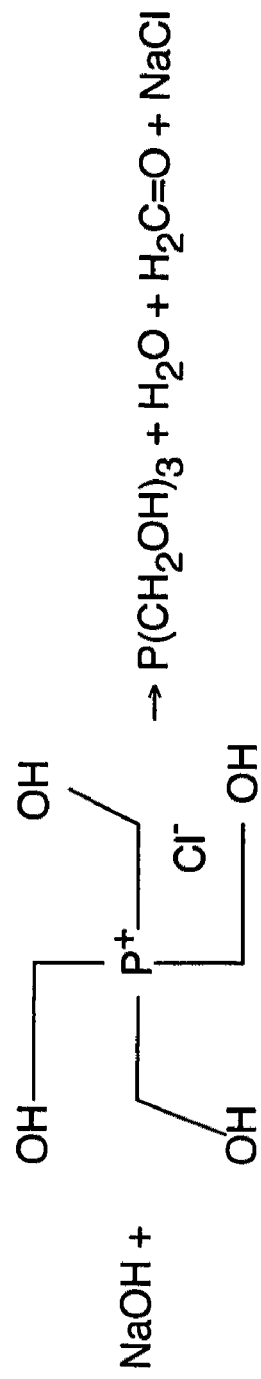
Figure 13C:
Figure 13D:
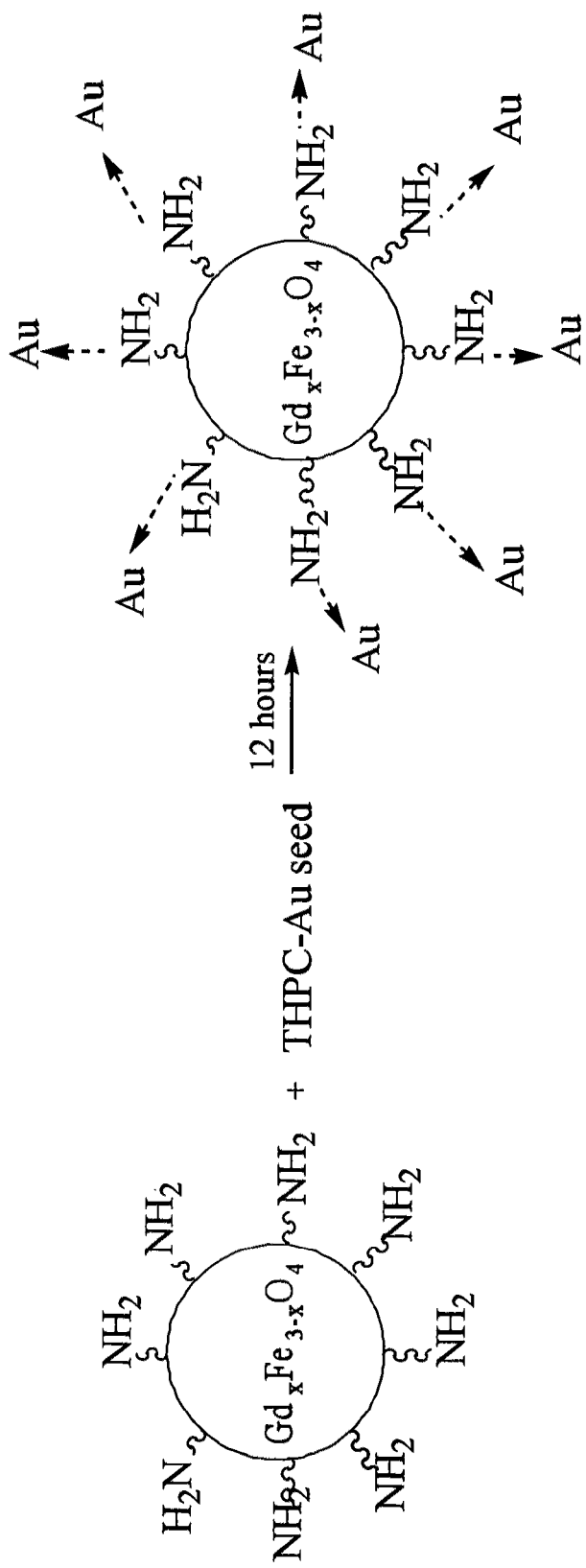
Figure 13E:
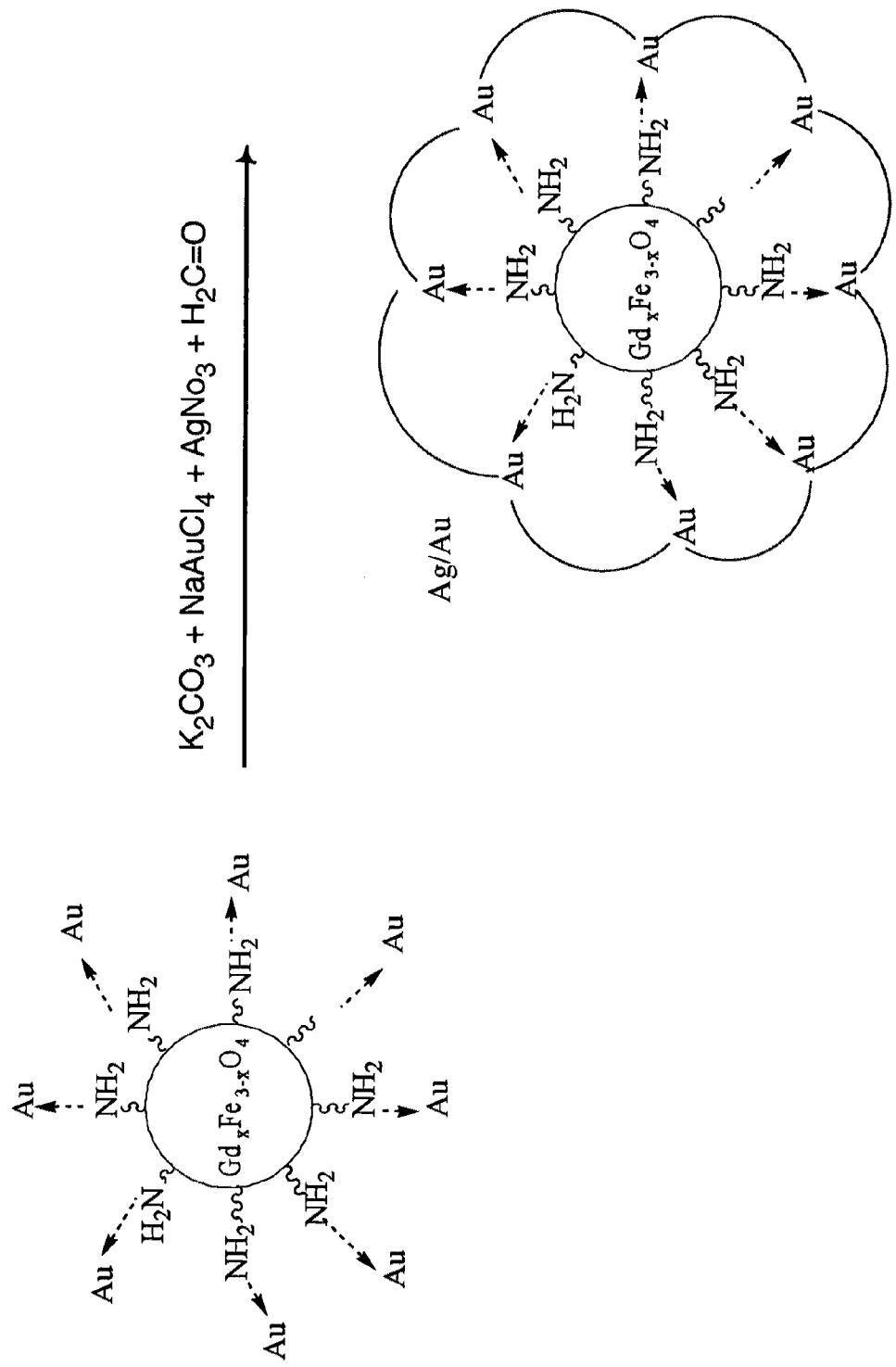

FIGS. 13A-13E depict the chemical steps to synthesize gold-silver alloy nanoshells onto gold-seeded Gd$_x$Fe$_{3-x}$O$_4$—NH$_2$ nanoparticles showing the formation of Fe$_3$O$_4$ (FIG. 13A), the formation of the tetrakis(hydroxy ethyl) phosphonium chloride-gold (THPC-Au) solution (FIGS. 13B-13C), the deposition of the gold seeds onto the Gd$_x$Fe$_{3-x}$O$_4$—NH$_2$ nanoparticles (FIG. 13D), and the deposition of the silver/gold nanoshell onto the gold-seeded Gd$_x$Fe$_{3-x}$O$_4$—NH$_2$ nanoparticles (FIG. 13E).

Figure 14:
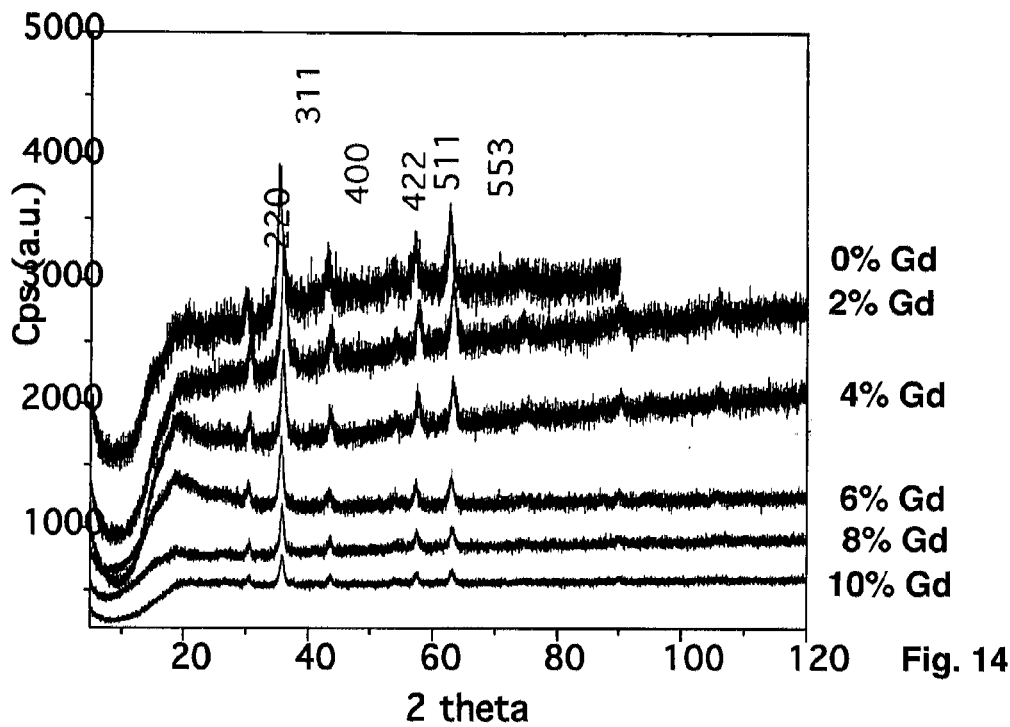

FIG. 14 shows a comparison of X-ray powder patterns of Fe$_3$O$_4$ and Gd$_x$Fe$_{3-x}$O$_4$ (x=2-10%) indicating the proof of incorporation of Gd(III) in the spinel structure of Fe$_3$O$_4$; hkl indices are shown for Fe$_3$O$_4$.

Figure 15:
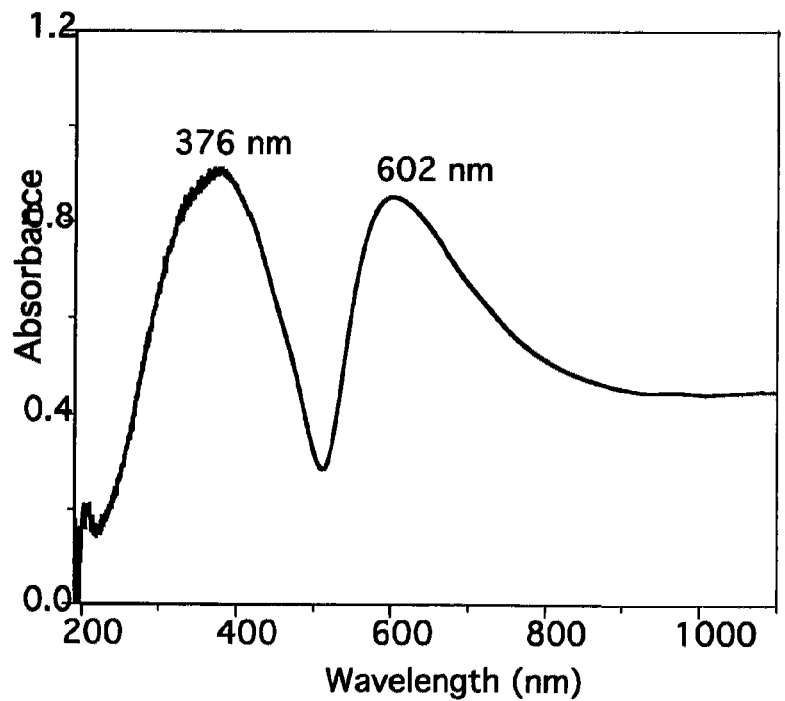

FIG. 15 is a UV-Vis spectrum of GdxFe$_{3-x}$O$_4$—NH$_2$/Au seeds (x=10%) using a THPC-Au seeds solution (0.5 mL) as a background.

Figure 16A:
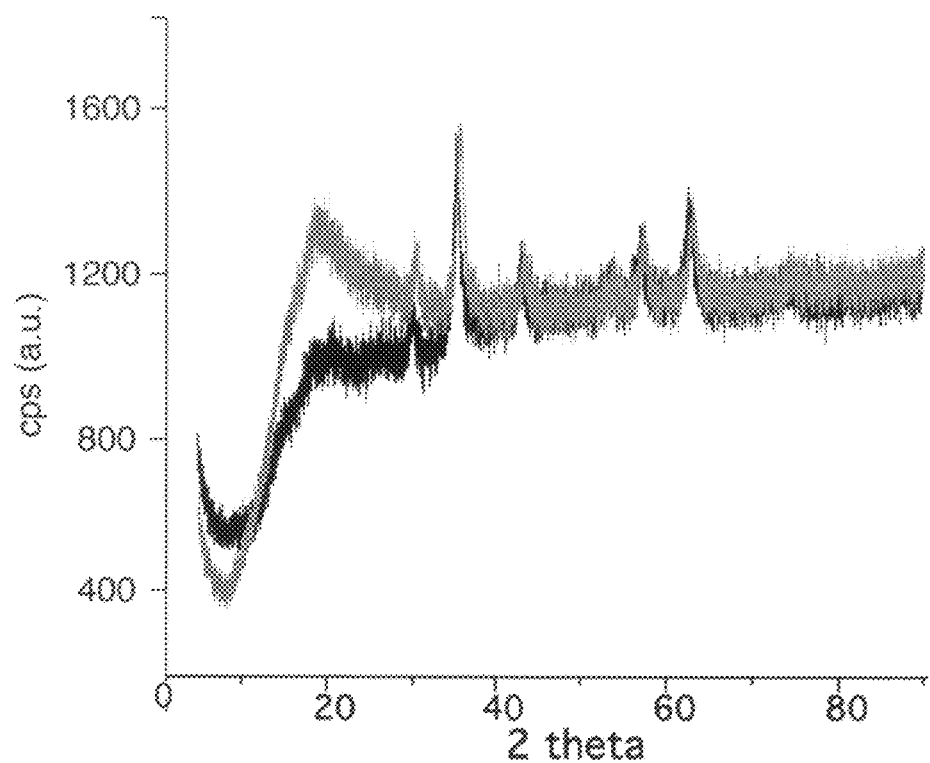
Figure 16B:
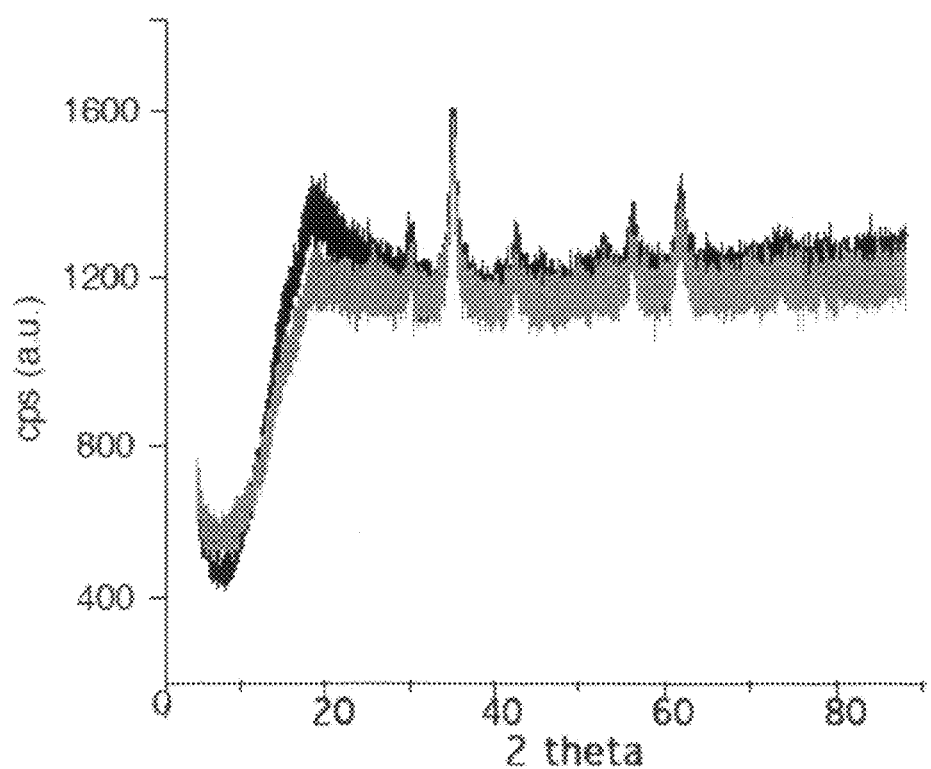

FIGS. 16A-16B are comparisons of the powder patterns of Fe$_3$O$_4$/γ-Fe$_2$O$_3$ for 3 hours (black) and 10 minutes (red) reaction time (FIG. 16A) and of Fe$_3$O$_4$ before (black) and after (red) the deposition of SiO$_2$ (FIG. 16B).

Figure 17:
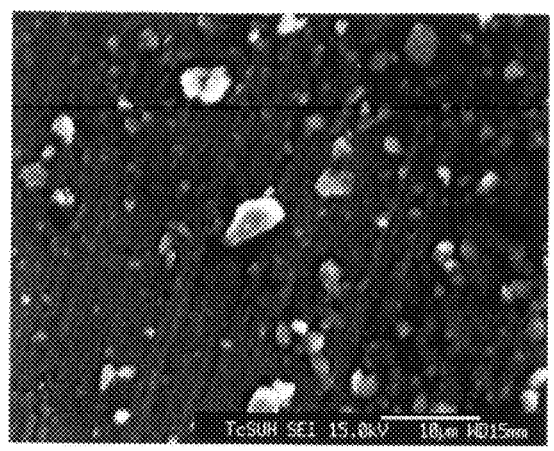

FIG. 17 shows SEM data for Fe$_3$O$_4$ (44.91% O and 55.09% Fe) formed after 10 minutes reaction time.

Figure 18A:
Figure 18B:

FIGS. 18A-18B are SEM photographs of γ-Fe$_2$O$_3$/SiO$_2$ particles.

Figure 19:
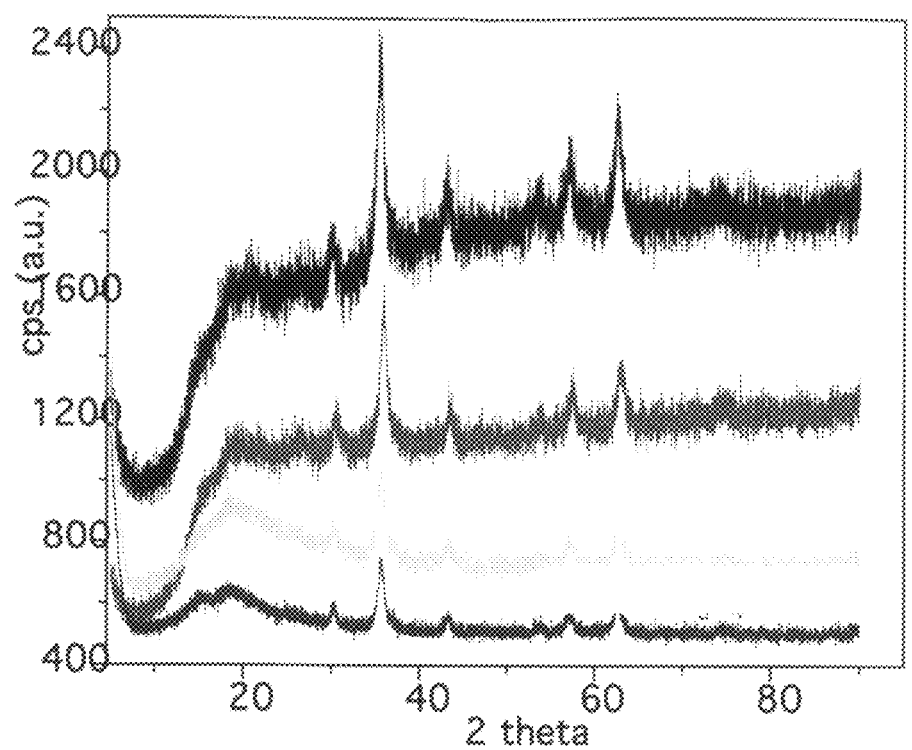

FIG. 19 is a comparison of X-ray powder patterns of Fe$_3$O$_4$ and Ru$_x$Fe$_{3-x}$O$_4$ (x=2,4 and 8%) indicating the proof of incorporation of Ru(III) in the spinel structure of Fe$_3$O$_4$.

Figure 20A:
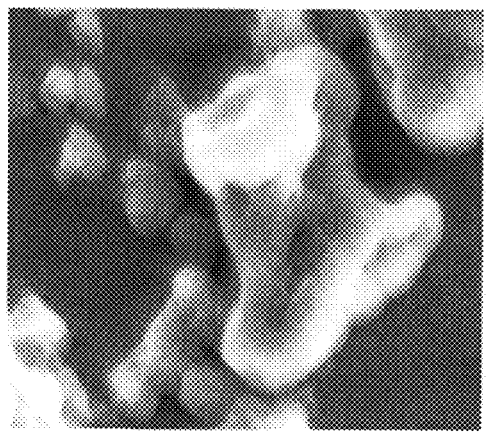
Figure 20B:
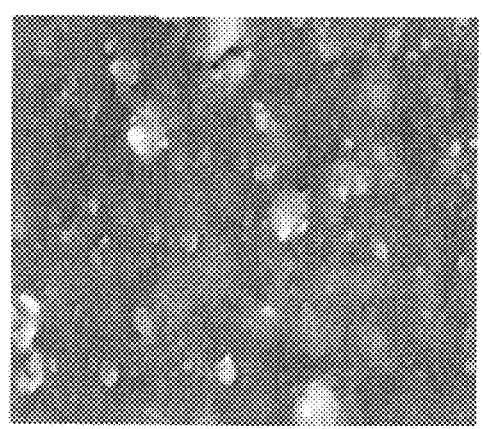
Figure 20C:
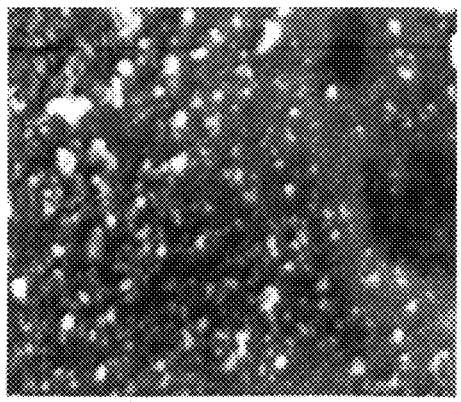
Figure 20D:
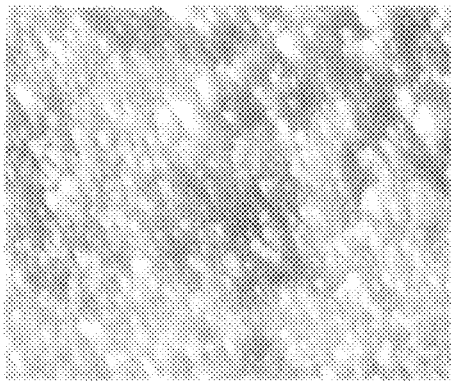
Figure 20E:
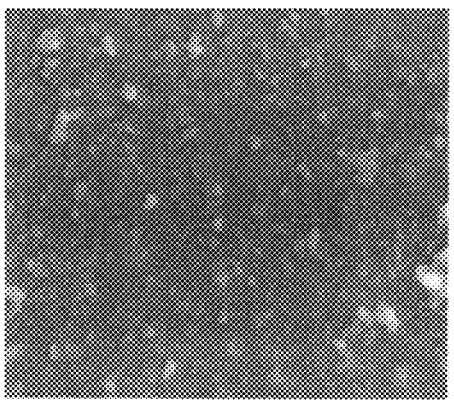
Figure 20F:
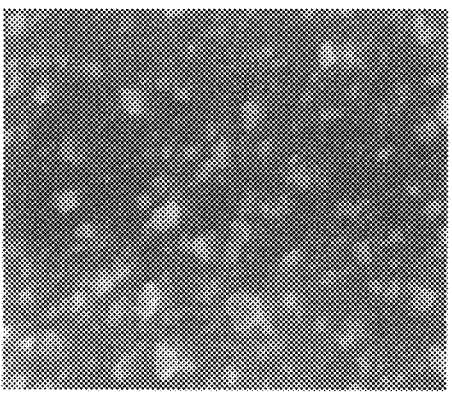
Figure 20G:
Figure 20H:
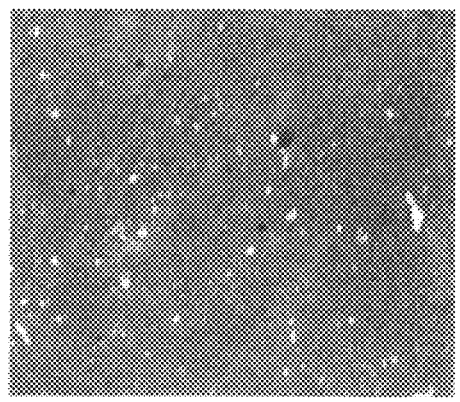

FIGS. 20A-20H are SEM micrographs of a) Ru$_x$Fe$_{3-x}$O$_4$ (x=2%) (FIG. 20A), b) Ru$_x$Fe$_{3-x}$O$_4$—NH$_2$ (x=2%; FIG. 20B), d) Ru$_x$Fe$_{3-x}$O$_4$ (x=4%; FIG. 20C), e) Ru$_x$Fe$_{3-x}$O$_4$—NH$_2$ (x=4%; FIG. 20D), g) Ru$_x$Fe$_{3-x}$O$_4$ (x=6%; FIG. 20E), h) Ru$_x$Fe$_{3-x}$O$_4$—NH$_2$ (x=6%; FIG. 20F), j) Ru$_x$Fe$_{3-x}$O$_4$ (x=8%; FIG. 20G), and l) Ru$_x$Fe$_{3-x}$O$_4$—NH$_2$/Au (x=8%; FIG. 20H).

Figure 21A:
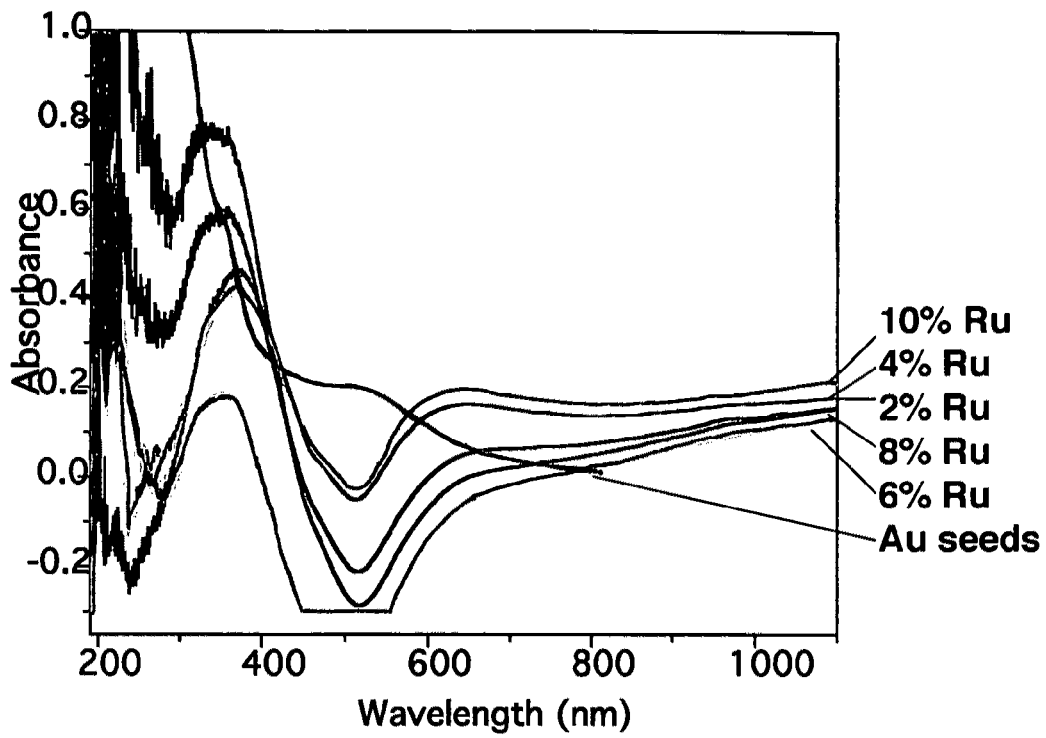
Figure 21B:
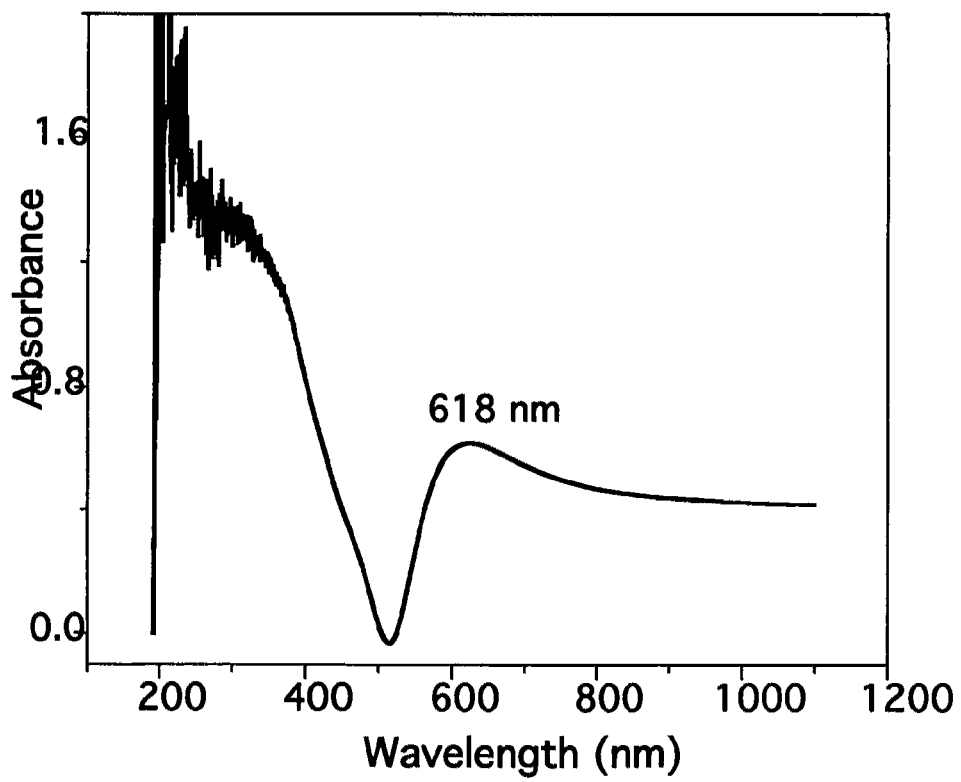

FIGS. 21A-21B are the UV-Vis spectra of Ru$_x$Fe$_{3-x}$O$_4$—NH$_2$ (x=2-10%) before and after Au-seeds deposition (FIG. 21A) and of Ru$_x$Fe$_{3-x}$O$_4$—NH$_2$/Au seeds (x=8%) using a THPC-Au seeds solution (0.5 mL) as background (FIG. 21A).

DETAILED DESCRIPTION OF THE INVENTION

As used herein, the term, "a" or "an" may mean one or more. As used herein in the claim(s), when used in conjunction with the word "comprising", the words "a" or "an" may mean one or more than one.

As used herein "another" or "other" may mean at least a second or more of the same or different claim element or components thereof. Some embodiments of the invention may consist of or consist essentially of one or more elements, method steps, and/or methods of the invention. It is contemplated that any method or composition described herein can be implemented with respect to any other method or composition described herein.

As used herein, the term "subject" refers to any recipient of the contrast agents and/or magnetic nanoparticles provided herein.

In one embodiment of the present invention there is provided a biomimetic contrast agent, comprising an amine-functionalized iron (II) oxide/iron(III) oxide nanoparticle core; a targeting ligand attached to the nanoparticle core via a linker; an inert outer layer of a hydrophilic polymer conjugated to the targeting ligand. Further to this embodiment the biomimetic contrast agent comprises a metal doping agent in the nanoparticle core. Examples of a metal doping agent are gadolinium, manganese or cobalt. In another further embodiment the biomimetic contrast agent comprises a gold coating on the nanoparticle core.

In all embodiments the ratio of the iron (II) to the iron(III) in the nanoparticle core may be about 1:1. Also, in all embodiments the linker may comprise a triethylene glycol polymer or a polyethylene glycol polymer. In addition, the inert outer layer may comprise a polyethylene glycol polymer.

Also, in all embodiments the targeting ligand may comprise a contiguous peptide sequence of an enzyme cleavable sequence and a targeting sequence in tandem. Further to these embodiments the targeting ligand may comprise a blocking agent bound to a terminal sidechain amino acid of the peptides. In an aspect of these embodiments the enzyme cleavable sequence may be cleavable by an enzyme associated with ovarian cancer cells. For example, the enzyme cleavable sequence may be a metalloproteinase-13 cleavable sequence, particularly the sequence shown in SEQ ID NO: 1. In another aspect the targeting sequence may be an endothelin-1 (ET-1) sequence, particularly the sequence shown in SEQ ID NO: 2, an integrin-binding sequence shown in SEQ ID NO: 3, or a human immunodeficiency virus Tat peptide sequence shown in SEQ ID NO: 4. Also in this aspect, the targeting ligand may have the contiguous sequences shown in one of SEQ ID NOS: 5-7.

In a related embodiment the present invention provides a kit comprising the biomimetic contrast agent as described supra.

In another embodiment the present invention provides an in vivo method using magnetic resonance imaging for detecting an early stage primary or metastatic cancer in a subject, comprising administering to the subject a sufficient amount of the biomimetic contrast agent described supra to provide a detectable contrast image of the contrast agent within the primary or metastatic cancer therein, wherein a location of the image correlates to a location of the cancer. Representative cancers may be ovarian cancer or breast cancer or other cancer expressing MMP-13 enzyme.

In yet another embodiment the present invention provides a contrast agent, comprising a metal-doped iron (II) oxide/iron(III) oxide nanoparticle core; an inert layer of gold coating the nanoparticle core; and a biodegradable cationic polymer linked thereto. Further to this embodiment the contrast agent comprises DNA encoding an anti-tumor cytokine complexed with the cationic polymer. In both embodiments the anti-tumor cytokine may be interleukin-12. Also, the doping metal may be gadolinium (III), manganese, cobalt, or ruthenium. In addition, the cationic polymer may comprise disulfide-reducible, linear, L-lysine-modified copolymers (LLC).

In a related embodiment the present invention provides a kit comprising the dual contrast agent described supra or this dual contrast complexed to a DNA encoding an anti-tumor cytokine. Further to this related embodiment the kit comprises the buffers and reagents effective to transfect mesenchymal stem cells with the contrast agent-DNA complex.

In another related embodiment the present invention provides a dual contrast agent and gene delivery system, comprising mesenchymal stem cells (MSCs) transfected with the contrast agent described supra complexed with a DNA encoding an anti-tumor cytokine. An example of an anti-tumor cytokine is interleukin-12.

In yet another embodiment of the present invention there is provided method for reducing metastasis of tumor cells in a subject, comprising administering to the subject an amount of the mesenchymal stem cells (MSCs) comprising the dual contrast agent and gene delivery system described herein sufficient to target metastatic tumor cells; simultaneously delivering the contrast agent and the anti-tumor cytokine thereto; and obtaining a magnetic resonance image of the contrast agent within the metastatic tumor cells; wherein simultaneously imaging the contrast agent and delivering the anti-tumor cytokine locates a site of metastatic tumor cells and induces a pro-inflammatory response against the same, thereby reducing metastasis of the tumor cells. Further to this embodiment the method comprises implementing one or both of a surgical regimen or one or more other chemotherapeutic regimens.

In yet another embodiment of the present invention there is provided a magnetic nanoparticle comprising an inner functionalized iron oxide core; an inert metal seeding the functionalized core; and an outer inert metal alloy nanoshell.

Further to this embodiment the magnetic nanoparticles may comprise a metal-doping agent in the nanoparticle core. Examples of metal-doping agents are gadolinium, manganese, cobalt, or ruthenium. In particular aspects the metal-doping agent comprises about 2% to about 10% of the iron oxide core. In another further embodiment the magnetic nanoparticles may comprise a targeting ligand attached to the nanoshell via linker. The linkers may comprise triethylene glycol polymer or a polyethylene glycol polymer.

In all these embodiments the inert seeding metal may be gold. Also, the inert metal-alloy comprising the nanoshell is a gold-silver alloy. In one aspect of these embodiments the iron oxide core comprises iron(III) oxide functionalized with an aminopropyl moiety. In another aspect the iron oxide core comprises an iron(III) oxide/iron(II) oxide functionalized with a silica layer.

In a related embodiment the present invention provides a magnetic nanoparticle comprising an amine-functionalized metal-doped iron(III) oxide core; a layer of gold seeding the amine-functionalized metal-doped iron oxide core; an outer gold-silver alloy nanoshell; and a targeting ligand attached to the nanoshell via a linker. In this embodiment the linker may comprise a triethylene glycol polymer or a polyethylene glycol polymer. Also, the iron(III) oxide core may be doped with gadolinium or ruthenium. In addition, the gadolinium or the ruthenium may comprise about 2% to about 10% of the iron oxide core.

In another related embodiment the present invention provides a magnetic nanoparticle comprising an iron(III) oxide/iron(II) core; a layer of silica around the core; an outer gold-silver alloy nanoshell; and a targeting ligand attached to the nanoshell via a linker. The linker may be as described supra.

In yet another embodiment of the present invention there is provided an in vivo method using magnetic resonance imaging for detecting an early stage primary or metastatic cancer in a subject, comprising administering to the subject a sufficient amount of the magnetic nanoparticles described supra to provide a detectable contrast image of the magnetic nanoparticles within the primary or metastatic cancer therein, where a location of the image correlates to a location of the cancer. Further to this embodiment the method may comprise irradiating the magnetic nanoparticles with a near infrared wavelength to generate heat therewithin effective to ablate the primary or metastatic cancer. Examples of primary or metastatic cancer are ovarian or breast cancer.

In yet another embodiment of the present invention there is provided a method for treating metastatic or primary cancer in a subject comprising administering the magnetic nanoparticles described supra to the subject to target one or both of the metastatic or primary cancers; and irradiating the magnetic nanoparticles with a near infrared wavelength effective to heat the same; where the heated nanoparticles cause thermolysis of cells comprising the cancer(s) thereby treating the metastatic or primary cancer in the subject. In this embodiment, the near infrared wavelength may be about 650 nm to about 900 nm. The primary and metastatic cancers are described supra.

In yet another embodiment of the present invention there is provided a method for ablating atherosclerotic plaque in a subject comprising administering the magnetic nanoparticles described supra to the subject to target vascular tissues having atherosclerotic plaque therein; and irradiating the magnetic nanoparticles with a near infrared wavelength effective to heat the same; where the heated nanoparticles ablate the atherosclerotic plaque in the subject. The near infrared wavelength is described supra.

The present invention provides biomimetic ultrasmall paramagnetic iron oxide (USPIO) nanoparticles (USPIO) with dual bioresponsive elements effective to selectively target tumor cells in the preclinical stage of development for early detection of cancer for use in magnetic resonance imaging. Such contrast agents act as early detection probes with broad availability to patients and lead to life saving early detection and treatment of cancer. The USPIO nanoparticles enhance sensitivity during magnetic resonance imaging (MRI) because of increased specificity for the target by providing a modifiable surface. The presence of two levels of targeting, based on specific tumor biochemistry, significantly increases the targeting of the probe to the tumor that would overcome the hurdles of late detection, safety, rapid elimination, and non-specific extravasation.

The contrast agent comprises an amine-functionalized nanoparticle core of an undoped or metal-doped iron oxide, a linker, a targeting ligand and an outer inert or stealth layer. The nanoparticle core may be an Fe(II)/Fe(III) oxide, such as which is biodegradable. The nanoparticles may be about 10-100nm, where ultrasmall nanoparticles are less than 50 nm, preferably about 20 nm to about 50 nm in diameter. For example, Fe(II)/Fe(III) oxide may be present in the core in a 1:1 ratio. A suitable doping metal is, but not limited to, gadolinium, manganese, cobalt, or ruthenium. The linker may comprise a short polyethylene glycol polymer (PEG), for example, a $PEG_{400}$ polymer, or a triethylene glycol polymer. Optionally, the nanoparticle core may be coated with an inert layer of gold.

The targeting ligand is covalently attached, conjugated or linked to the nanoparticle core via the linker. The targeting ligand comprises two contiguous peptide targeting sequences. The first targeting peptide sequence is cleavable by an enzyme associated with a cancer. For example, the cancer may be any cancer expressing the metalloproteinase-13 enzyme, such as ovarian cancer, and the peptide may be cleavable by metalloproteinase-13 enzyme. This peptide sequence may comprise a PQGLA sequence (SEQ ID NO: 1). The second targeting peptide sequence is a cancer cell specific peptide that binds to the tumor cells. For example, the second targeting peptide sequence may be an endothelin-1 (ET-1) sequence, such as CSCSSLMDKECVYFCHLDIIW (SEQ ID NO: 2) or an integrin-binding sequence, such as an RGDS peptide sequence (SEQ ID NO: 3) or a human immunodeficiency virus (HIV) Tat peptide sequence, such as YGRKKRRQRRR (SEQ ID NO: 4). The peptides comprising the targeting sequences may be blocked, that is, the amino acid side chains comprising the peptides may be blocked by a blocking agent selective for the amino acid. The peptides are synthesized as described in Example 3.

Thus, a contiguous targeting ligand sequence may comprise the MMP-13 cleavable sequence PQGLA and the ET-1 sequence as GCSCSSLMDKECVYFCHLDIIWGPQGLAG (SEQ ID NO: 5), the integrin-binding sequence as GRGDS-GPQGLAG (SEQ ID NO: 6), and the HIV Tat sequence as GYGRKKRRQRRRGPQGLAG (SEQ ID NO: 7). Glycine residues are added as spacers at the beginning and end of the contiguous sequence and between the first and second targeting sequences to increase enzyme recognition of the sequence. The nanoparticle-targeting ligand conjugate further comprises an inert or stealth outer layer, such as a hydrophilic polymer, for example, but not limited to, a polyethylene glycol polymer conjugated to the targeting ligand. The PEG polymers may be a $PEG_{2000}$ to about $PEG_{5000}$.

As a representative example, the contrast agents disclosed herein take advantage of the presence and role of metalloproteinase-13 (MMP-13) in ovarian cancer and other cancers, such as breast cancer, because this enzyme is active within these carcinomas that also express specific cellular receptors. The endothelin receptor ($ET_AR$) and endothelin-1 (ET-1) peptide are produced in both primary and metastatic ovarian tissue as well as the integrin ($\alpha_v\beta_3$) receptors that bind the arginine-glycine-aspartic acid-serine (RGDS) sequence. In addition, the HIV Tat protein transduction domain has been shown to be a very effective and promiscuous cell penetrating peptide.

In general, upon administering the biomimetic contrast agent to a subject, the outer layer prevents non-specific cellular uptake of the contrast agent as well as to limit premature interactions with blood and immune components. At the first level of targeting, the enzyme cleavable peptide sequence is recognized and cleaved only within the tumor compartment by the enzyme which releases the outer protective stealth layer. Release of the stealth layer reveals, as the second level of targeting, the second peptide sequence, which as a ligand, specifically binds to the tumor cells for cellular uptake of the contrast agents for magnetic resonance imaging.

The present invention also provides a dual contrast agent and gene delivery system useful with a MRI imaging modality. The system comprises a nanoparticle-based platform (USPIO) to enable detection and cell-based gene therapy treatment of metastatic cancer, such as, but not limited to, metastatic breast cancer. The contrast agent may comprise the gold-coated metal-doped iron oxide nanoparticle core described herein. Particularly, a gadolinium-doped, such as gadolinium (III), iron oxide nanoparticle core is coated with an inert layer of gold.

The gold-coated nanoparticles are conjugated to cationic polymers that may comprise novel disulfide-reducible, linear, L-lysine-modified copolymers (LLC). The cationic polymers are effective to form a complex with a therapeutic gene, particularly a chemotherapeutic gene. Examples of therapeutic genes may be interleukins, such as, interleukin-12. It is contemplated that plasmid DNA encoding the therapeuic gene is complexed with the cationic polymer using well-known and standard molecular biological techniques.

The cationic polymer-AuGdUSPIO nanoparticle conjugate further functions in a gene or drug delivery system. These cationic nanoparticles can transfect mesenchymal stem cells (MSCs) using standard molecular biological techniques. MSCs demonstrate homing properties to tumor cells, have been used as gene delivery vehicles, have reduced immunogenicity and are easy to expand and maintain in cell culture.

In addition, the present invention also provides kits comprising the contrast agents, including the contrast agent complexed to a DNA encoding a therapeutic DNA. Also, a kit comprising the contrast agent useful in the gene delivery system may further comprise those buffers, reagents, etc. standard in the art that are useful during transfection of a mesenchymal stem cell with the DNA-contrast agent complex.

As such, the present invention provides in vivo magnetic resonance imaging methods using the contrast agents described herein. These contrast agents may be administered in amounts sufficient to produce a detectable magnetic resonance image in cancerous cells or tissues or tumors. These methods are well suited to detect early stage primary or metastatic cancers, such as, but not limited to, ovarian or breast cancers, upon targeting thereto. One of ordinary skill in the art is well-suited to determine amounts of the contrast agents to administer to a subject, the route of administration and the MRI imaging conditions necessary to obtain a useable detectable image. Furthermore, such early detection greatly enhances the prognosis of the subject.

Also, the present invention provides methods of simultaneously detecting one or more sites of metastatic cancer cells and reducing metastasis of metastatic cells distal to a primary cancer or tumor using the dual contrast agent and gene delivery system described herein during MRI. The method is particularly useful in reducing metastasis of a breast cancer to or metastatic breast cancer cells in the bones, lung, liver, and brain of the subject. It is contemplated that delivery of the anti-tumor gene, such as, interleukin-12 would induce a pro-inflammatory response against the metastatic cancer cells. One of ordinary skill in the art is well able to determine the dosage of the transfected MSCs based on the type of metastatic cancer, the progression of the cancer, the health of the subject, etc. and the conditions for MRI are easily determined. Upon location of the metastatic cells in the subject, the methods further provide for additional therapeutic intervention, such as, surgical removal of cancerous tissue and/or one or more additional chemotherapeutic agent or drug regimens as are well-known and standard.

The present invention further provides magnetic nanoparticles that comprise a gold-silver alloy nanoshell. The magnetic core of the nanoparticles may be an iron oxide, doped with a suitable metal doping agent (M), such as but not limited to gadolinium, ruthenium, manganese, or cobalt, preferably gadolinium, such as gadolinium(III), or ruthenium. The metal doping agent forms a nanoparticle, $MFe_3O_4$, where the percentage of metal doping agent in the magnetic core is, but not limited to, about 2% to about 10%. The magnetic core is functionalized further with, for example, an amino-containing moiety such as an aminopropyl moiety, which can form an amido with an inert metal. For example, the functionalized magnetic nanoparticles may be seeded with gold. A gold-silver alloy nanoshell forms an outer layer around the functionalized magnetic nanoparticles.

Alternatively, the iron oxide core may comprise a silica layer around which the gold-silver alloy nanoshell is formed. Silica is deposited onto a $Fe_3O_4/\gamma\text{-}Fe_2O_3$ core which is subsequently seeded with an inert metal, such as gold, as with the metal-doped iron oxide nanoparticles. The gold-silver alloy nanoshell is formed around the seeded silica layer.

The magnetic nanoparticles may be further modified as provided herein to provide efficacious contrast agents and drug delivery agents. Furthermore, by adjusting the percentage and type of doping metal in the magnetic core, the magnetic nanoparticles become tunable. That is, a particular magnetic nanoparticle composition will have an absorption maximum in the near infrared range, for example, from about 650 to about 900 nm. At these wavelengths, hemoglobin and water have their lowest extinction coefficients. Therefore, tissues can be heated at these wavelengths without damaging cells.

Thus, the present invention also provides a method for treating a pathophysiological condition, such as a cancer or a condition associated with vascular tissue or cells, for example, atherosclerosis. The magnetic nanoparticles, which are targeted to cells, tissue or other site of interest associated with the pathophysiological condition, will absorb near infrared radiation delivered thereto and, upon becoming heated by the NIR, result in selective thermolysis or ablation or other damage or cell death without damaging untargeted cells or tissues. Devices and methods for delivering radiation of a particular wavelength, such as by, but not limited to, lasers, to a targeted site are well-known and standard in the art.

The following examples are given for the purpose of illustrating various embodiments of the invention and are not meant to limit the present invention in any fashion.

EXAMPLE 1

Synthesis of Metal- and Undoped Ultrasmall Paramagnetic Iron Oxide Nanoparticles (USPION)

The synthesis of undoped iron oxide nanoparticles and gadolinium, manganese, cobalt, and ruthenium doped iron oxide nanoparticles were carried out using a modified procedure by Hong et al. (17) For metal-doped particles, the concentration of the gadolinium ions in the final product was 0, 2, 4, 6, 8, and 10 % and was 8% for both manganese and cobalt to the total amount of the $Fe^{3+}/Fe^{2+}$ ions. Calculations were done such that the concentration of $Fe^{2+}/Fe^{3+}=1$. Calculated amount of $FeCl_2 \cdot 4H_2O$ (M.W: 198.81) and $FeCl_3 \cdot 6H_2O$ (M.W: 270.3) and, for metal-doped nanoparticles, a stoichiometric amount of metal chloride salts were weighed and dissolved in ultra-pure water. Table 1 shows the amounts of $FeCl_2 \cdot 4H_2O$, $FeCl_3 \cdot 6H_2O$ and gadolinium used in the nanoparticle core.

TABLE 1

| | Amount of $FeCl_2 \cdot 4H_2O$ | Amount of $FeCl_3 \cdot 6H_2O$ |
|---|---|---|
| 1.5 g $Fe_3O_4$ + 0 g Gd (0%) | 0.6348 g (3.2 mmol) | 0.8651 g (3.2 mmol) |
| 1.47 g $Fe_3O_4$ + 0.03 g Gd (2%) | 0.6221 g (3.136 mmol) | 0.8478 g (3.136 mmol) |
| 1.44 g $Fe_3O_4$ + 0.06 g Gd (4%) | 0.6094 g (3.072 mmol) | 0.8305 g (3.072 mmol) |
| 1.41 g $Fe_3O_4$ + 0.09 g Gd (6%) | 0.596 g (3.008 mmol) | 0.813 g (3.008 mmol) |
| 1.38 g $Fe_3O_4$ + 0.12 g Gd (8%) | 0.5841 g (2.944 mmol) | 0.7959 g (2.944 mmol) |
| 1.35 g $Fe_3O_4$ + 0.15 g Gd (10%) | 0.5713 g (2.88 mmol) | 0.778 g (2.88 mmol) |

After the complete dissolution of the reactants, the mixture was transferred to a three neck round bottom flask in an inert atmosphere. The reaction mixture was then heated to 60° C. for about 15-20 mins followed by the addition of liquid ammonia to a rapidly stirring mixture. Additional ammonia was added to adjust the pH of the solution in the range of 8-9, and the nanoparticles were allowed to grow for additional 90 minutes. After 90 minutes the reaction mixture was split in two 500 ml centrifuge tube and the nanoparticles obtained were centrifuged for 20 mins at 5000 r.p.m. Supernatant liquid obtained was discarded and nanoparticles obtained were washed 3 times with ultra pure water until it showed a negative test for the presence of chloride ions. After no more chloride ions were present, half of the particles were transferred to a three neck round bottom flask with Ethanol/Water as the suspending solvent for functionalization, while other half was stored in water in the 500 ml centrifuge tube for further characterization.

Figure 2A:
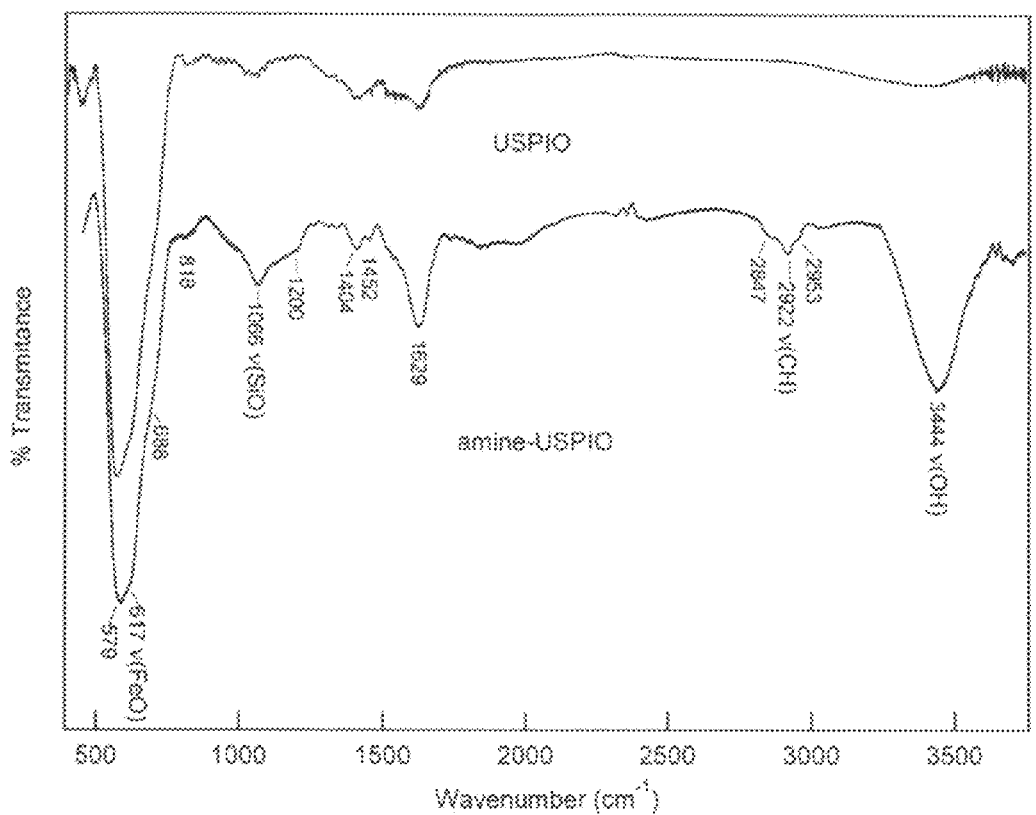
FIGS. 2A-2C are the FTIR spectrum of USPIO and amine-USPIO (FIG. 2A) and the TEM image of USPIO (FIG. 2B) and amine-USPIO (FIG. 2C).
Figure 2B:
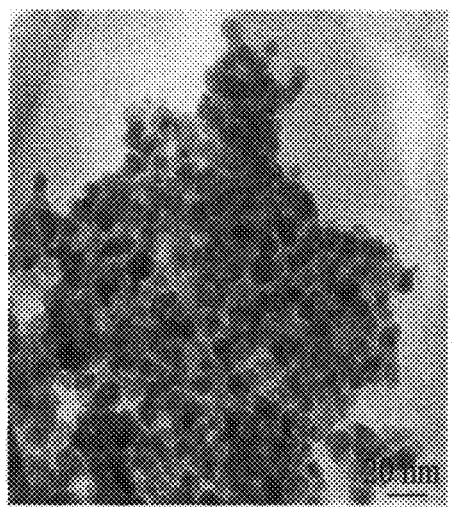
Figure 2C:
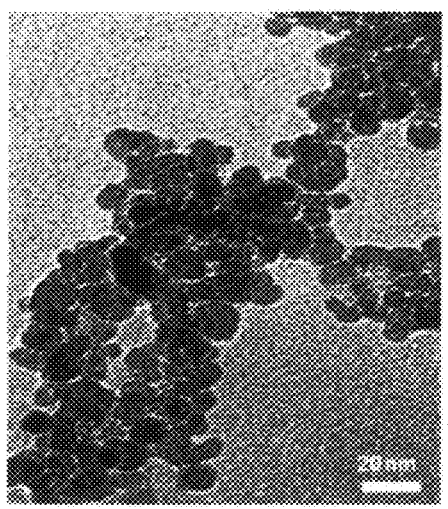
Figure 3:
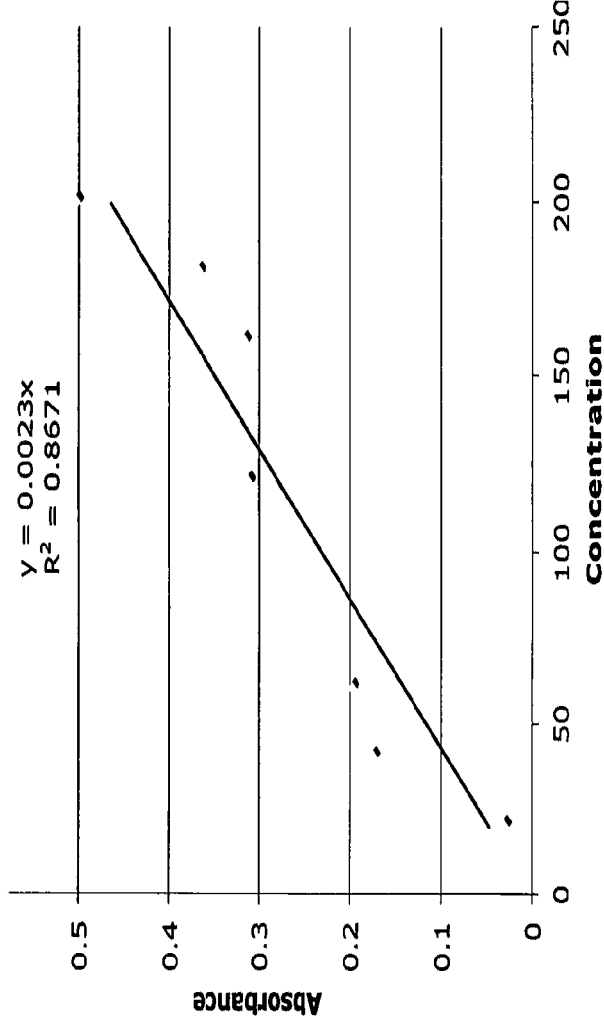
FIG. 3 shows results for the ninhydrin assay for the quantitative determination of the conjugation of 3-aminopropyltrimethoxysilane (APTMS) to ultra small paramagnetic iron oxide nanoparticles

Synthesis of Amine-functionalized Gadolinium-Doped Ultrasmall Paramagnetic Iron Oxide (Amine-GdUSPIO) Nanoparticles FIGS. 1A-1B are synthetic schema for Gd-doped USPIOs and amine-GdUSPIOs. The metal-doped and undoped USPIO nanoparticles obtained in the previous step were transferred to a three neck round bottom flask and heated to 60° C. for about 15 minutes. After 15 minutes, 15 mls of 3-aminopropyltrimethoxysilane (APTMS) was added drop wise through addition funnel or with a syringe to the rapidly stirring mixture. The reaction mixture was further heated at 60° C. for about an hour with constant stirring to allow complete functionalization. After the completion of reaction, the reaction mixture was again transferred to 500 ml centrifuge tube and the mixture was centrifuged for about 20 minutes at 5000 r.p.m. The supernatant liquid was discarded and functionalized nanoparticles were washed three times with ethanol followed by washing with water, and finally the reaction mixture was stored in water for further characterization. FIG. 2A shows the IR spectrum of USPIO and amine-USPIO. Whereas the particle size measure by TEM was observed to be around 8-10 nm (FIGS. 2B-2C). Results for the quantitative determination of the conjugation of APTMS to ultra small paramagnetic iron oxide nanoparticle using a standard ninhydrin assay are shown in FIG. 3 and the values obtained with this assay are shown in Table 2.

TABLE 2

| | Samples Absrobance | Blank | Final | Conc. Amine nmole/ml |
|---|---|---|---|---|
| | 0.173 | 0.066 | 0.107 | 46.52173913 |
| | 0.142 | 0.066 | 0.076 | 33.04347826 |
| | 0.124 | 0.066 | 0.058 | 25.2173913 |
| | 0.091 | 0.066 | 0.025 | 10.86956522 |
| Average | 0.1325 | 0.066 | 0.0665 | 28.91304348 |
| STDEV | 0.034278273 | 0 | 0.03427827 | 14.90359696 |

Synthesize Au-coated $M_xFe_2O_3$

Figure 4A:
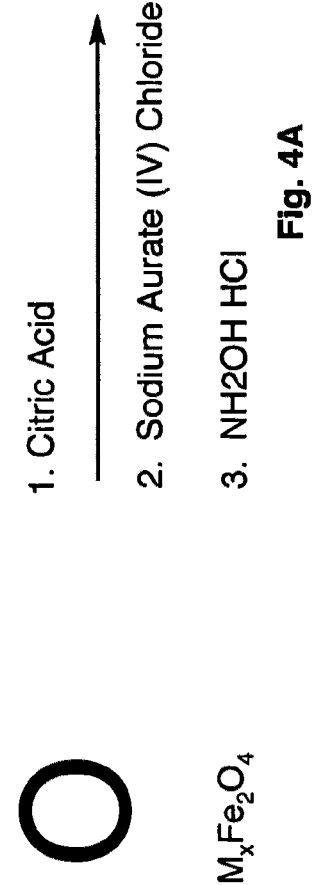
FIGS. 4A-4C depict the synthesis of gold coated doped iron oxide nanoparticles (FIG. 4A) and the electronic absorption spectra of various gold coated doped iron oxide nanoparticles (FIG. 4B) and TEM images of gold-coated doped nanoparticles (FIG. 4C).

FIG. 4A is the synthetic scheme for gold-coated doped USPIOs. 100 ml of metal (Gd, CO, or Mn) doped iron oxide nanoparticle was diluted to 1 ml with water and the particles were suspended with 2 mls of 0.1 M citiric acid. Once the particles were suspended it was followed by the successive alternate addition of 1 ml of 1 % $HAuCl_4$ and 2ml of $NH_2OH.HCl$. The addition of 1% $HAuCl_4$ was increased to 2 ml after $1^{st}$ two additions. The amount of 0.1M $NH_2OH.HCl$ was maintained same for all the five additions. After the solution turned faint purple or pink. Two more iterations of $HAuCl_4$ were added to precipitate all the particles which were then separated using magnet.

Figure 4B:
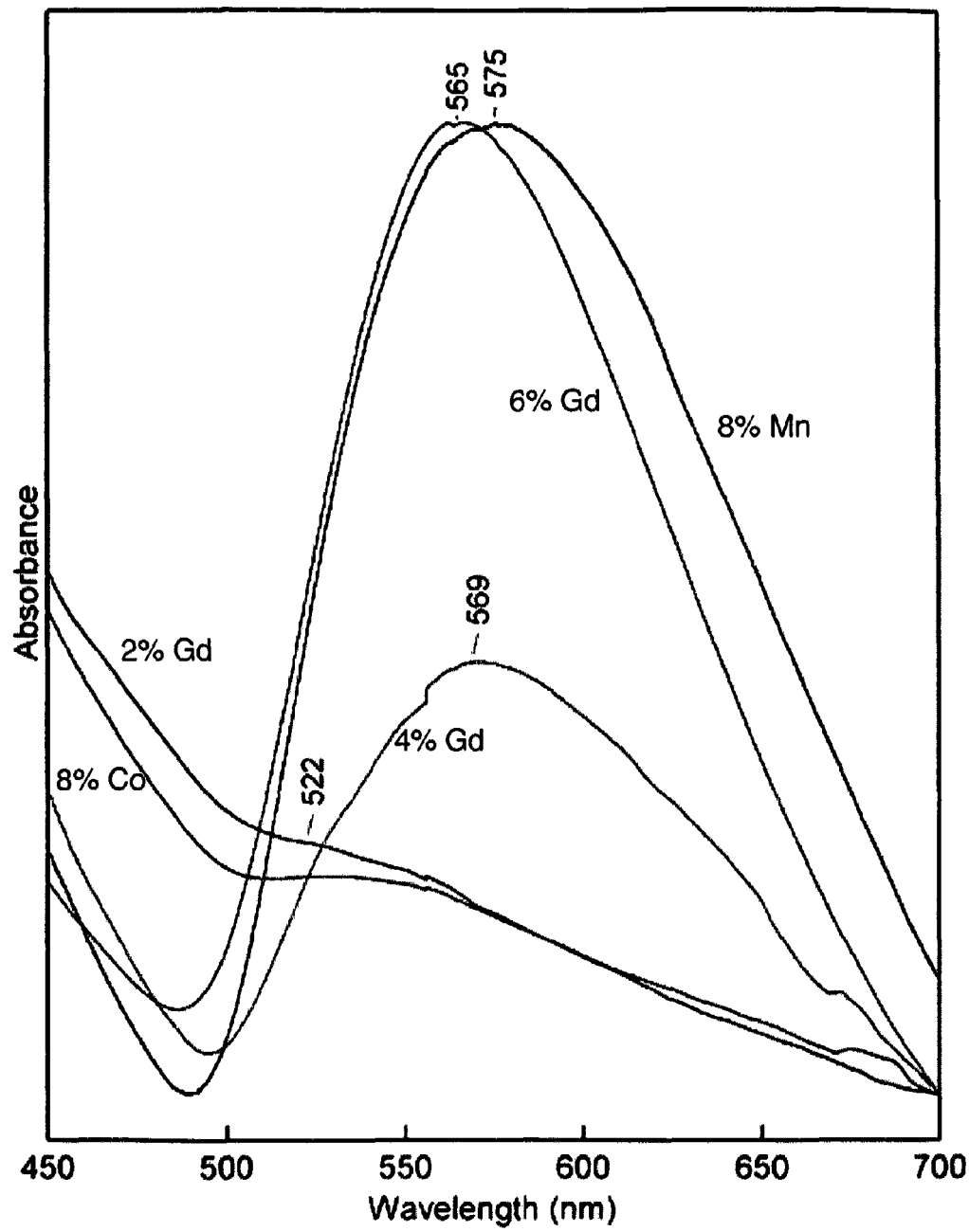
Figure 4C:
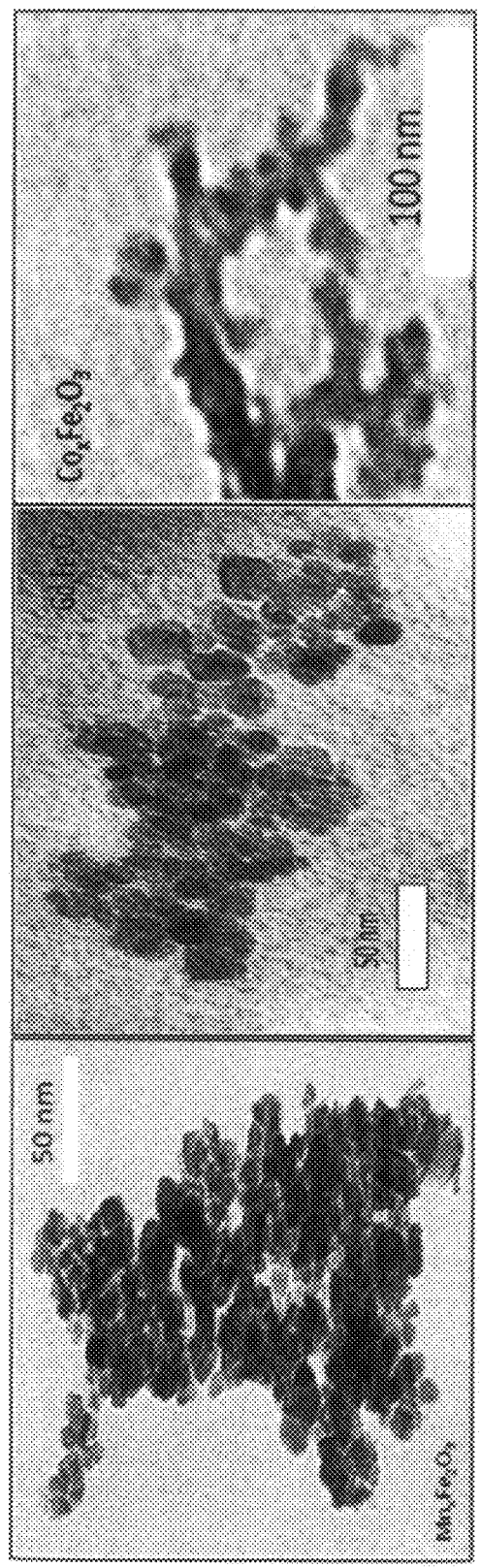

UV visible absorption spectra in FIG. 4B shows ~530-575 nm absorption of energy by the gold coated nanoparticles in various samples. The presence of Gd, Mn and Co in various samples was characterized using ICP-AES. Table 3 shows the relative concentration of all the elements in various samples. Further, the concentration of Gd in most of the sample was displayed as 0 due to very low solubility of these gold coated samples into the solution which resulted in overall decrease in the detection limit of gadolinium. These particles were characterized with the particle size of 15-20 nm as shown in the TEM images in FIG. 4C.

TABLE 3

| Samples | Fe | Gd | Mn | Co | Au |
|---|---|---|---|---|---|
| USPIO | 118.20 | 0.00 | | | |
| 4% Gd USPIO | 114.40 | 0.38 | | | |
| 6% Gd USPIO | 109.54 | 0.41 | | | |
| 8% Gd USPIO | 101.50 | 9.20 | | | |
| 10% Gd USPIO | 87.50 | 10.53 | | | |
| Gold Coated Samples | | | | | |
| 2% Gd USPIO | 15.4 | 0.08 | 0 | 0 | 65.93 |
| 4% Gd USPIO | 2.15 | 0 | 0 | 0 | 36.33 |
| 6% Gd USPIO | 1.5 | 0 | 0 | 0 | 63.25 |
| 8% Gd USPIO | 2.9 | 0 | 0 | 0 | 53.58 |
| 10% Gd USPIO | 2.4 | 0 | 0 | 0 | 28.3 |
| 8% Mn USPIO | 40.7 | 0 | 1.3 | 0 | 3.09 |
| 8% Co USPIO | 36.06 | 0 | 0 | 1.12 | 3.97 |

EXAMPLE 2

Spectroscopic Characterization of GdUSPIO and Amine-GdUSPIO Nanoparticles Fourier Transform-Infra Red (IR) Vibrational Spectrum To confirm the presence of the amine groups present on amine-GdUSPIO, FT-IR spectroscopy was used for both GdUSPIO and amine-GdUSPIO. The FT-IR spectra were measured at room temperature with a Nicolet Avator 360 FT-IR spectrophotometer (Varian, Palo Alto, Calif.). Sample concentrations in the pellets were ~1 mg of sample/200 mg of KBr salt. The synthesized MNPs were pressed into KBr pellets to record the solid state infrared spectra. To improve the signal-to-noise ratio, multiple scans (264) of each sample were collected and the slowly sloping baselines were subtracted from the digitally collected spectra using GRAMS/32 software package (Thermo Galactic, Inc. Salem, N.H.).

Figure 5A:
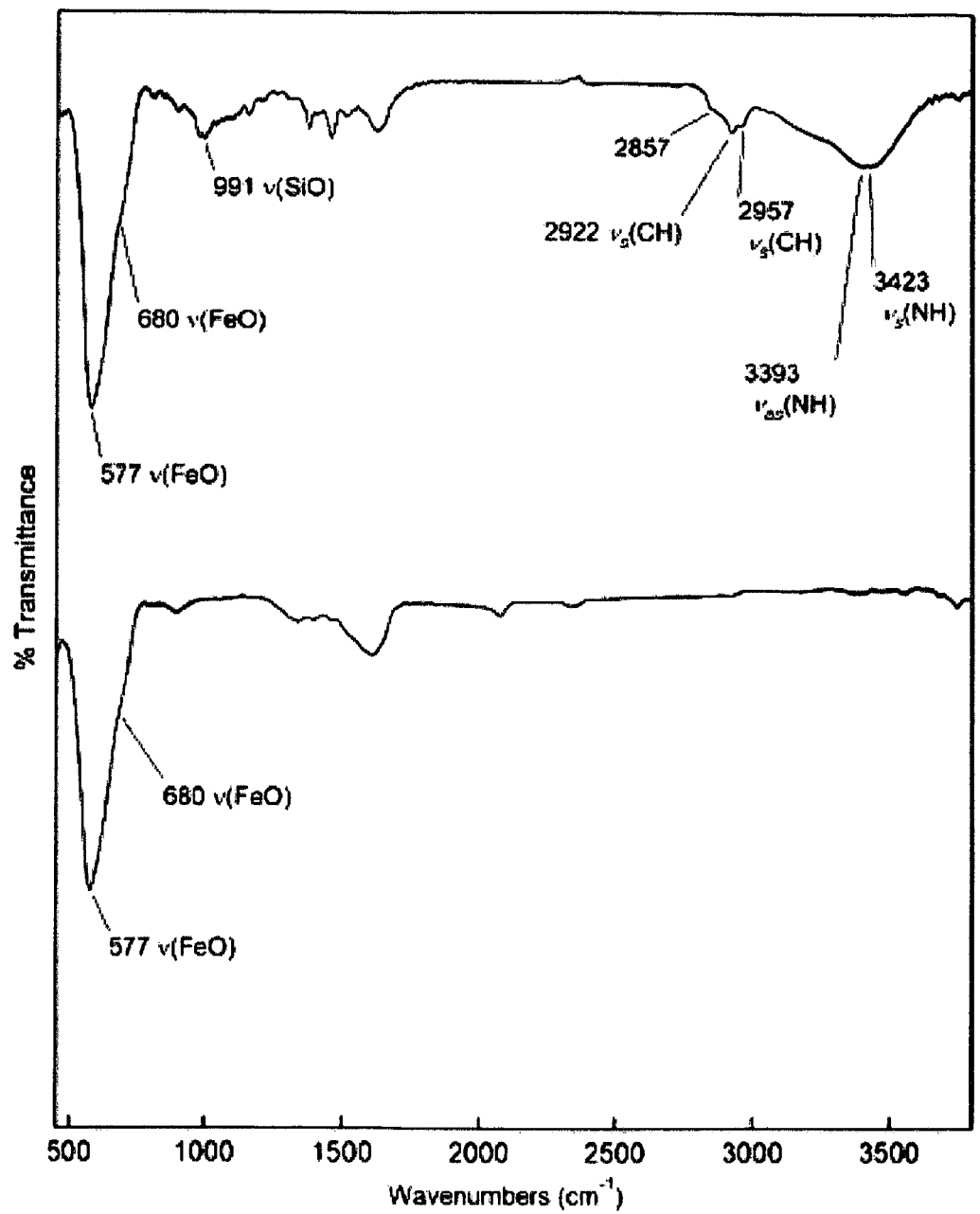
FIG. 5A-5D depict the Fourier Transform-Infrared (FT-IR) vibrational spectra of synthesized amine-GdUSPIO (top) and GdUSPIO (bottom) nanoparticles (FIG. 5A), the X-Ray Diffraction (XRD) pattern of synthesized GdUSPIO (top) and amine-GdUSPIO (bottom) nanoparticles (FIG. 5B) and the Transmission Electron Microscopy (TEM) images of synthesized (FIG. 5C) GdUSPIO and (FIG. 5D) amine-GdUSPIO nanoparticles.

The combined FT-IR spectra of synthesized amine-GdUSPIO (FIG. 5A—top) and GDUSPIO (FIG. 5A—bottom) showed the spinel structure of GdUSPIO and amine-GdUSPIO with vibrational bands at 577 and 680 $cm^{-1}$, which corresponded to the stretching vibrations of magnetite (n(Fe—O)) having different symmetry. In addition, the vibrational band at 577 $cm^{-1}$ is attributed to the $T_{2g}$ modes of vibrations and the vibrational band at 686 $cm^{-1}$ is attributed to the presence of $A_{1g}$ modes of vibrations of the Fe—O. These vibrations in the IR region confirmed the presence of the magnetite crystal lattice.

The surface functionalization of the magnetite lattice was confirmed by the presence of the 2922 and 2957$cm^{-1}$ vibrational bands in the IR spectrum of amine-GdUSPIO. These vibrational bands of amine-GdUSPIO can be attributed to the symmetric ($n_s$(CH)), and asymmetric stretching vibrations ($n_{as}$(CH)), respectively, which corresponds to the —$CH_2$ present in the APTMS molecule. The absorption band at 2843 $cm^{-1}$ can be attributed to the symmetric stretching vibrations of ($n_s$(O—$CH_3$)) of APTMS. The amine functionalized GdUSPIO was confirmed by the presence of the amine symmetric (($n_s$(NH)) and asymmetric ($n_{as}$(NH)) stretching vibrations of —$NH_2$ at 3423 and 3393 $cm^{-1}$, respectively.

Finally, the presence of the symmetric stretching vibrations of the silane groups ($n_s$(Si—O)) at 991 $cm^{-1}$ in amine-GdUSPIO confirmed the presence of the siliane molecules bonded to the metal oxide surface. This further confirmed the amine-functionalization of the GdUSPIO nanoparticles. The observed FT-IR vibrational frequencies for both GdUSPIO and amine-GdUSPIO are also tabulated in Table 4 for better comparison.

TABLE 4

| Assigments | GdUSPIO ($cm^{-1}$) | amine-GdUSPIO ($cm^{-1}$) |
|---|---|---|
| n(Fe—O) | 577 | 577 |
| n(Fe—O) | 680 | 686 |
| $n_s$(SiO) | — | 991 |
| $n_s$(O—$CH_3$) | — | 2843 |
| $n_{as}$(CH) | — | 2922 |
| $n_s$(CH) | — | 2957 |
| $n_s$(NH) | — | 3423 |
| $n_{as}$(NH) | — | 3393 |

X-Ray Diffraction (XRD) Pattern

The phase morphology of the MNPs was identified from the XRD pattern of the nanoparticles that was obtained from the Siemen D5000 q/2q Diffractometer (Siemen, New York, N.Y.) using Cu Ka X-Ray line. Briefly, 1.0 mg of sample was suspended in isopropanol to form a concentrated slurry, which was then finely ground with a mortar and pestle. The sample was spread on to the sample holder to form a thin layer of nanoparticles and the XRD pattern was recorded by varying 2q from 15-77°. The tube voltage was kept at 40 kV and the current used was 30 mA at all time points. All the spectral figures were prepared with the IGOR Pro (version 6.0) software. The reflection at 311 lattice plane was used to estimate the average crystalline size by applying the Scherrer model. The Scherrer model is expressed as Equation 1:

$$d = 0.91 l / b \cos q \quad \text{Eq. (1)}$$

where I=0.154 nm for Cu $K_a$ line; d is the crystalline diameter, b is the full width at the half maximum of the 311 peak in radians, and q is the peak position in radians.

Figure 5B:
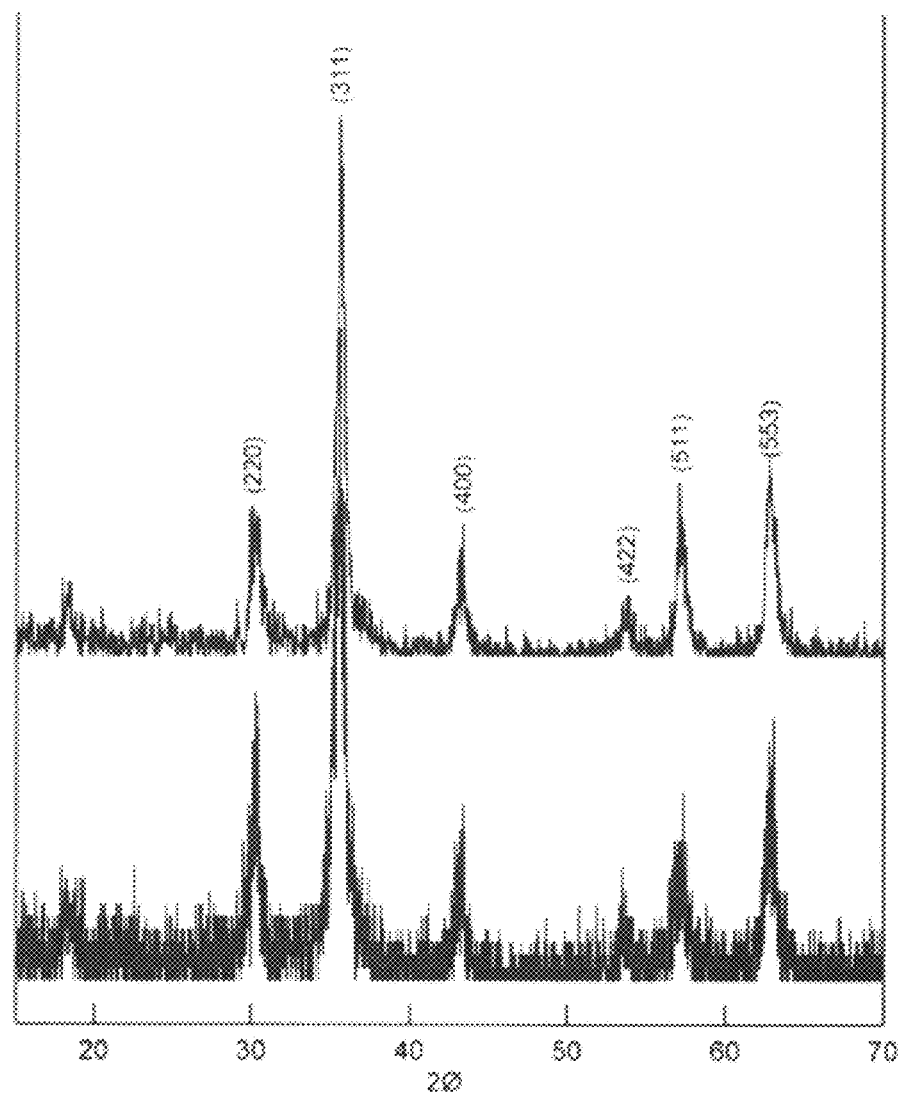

The spinel structure of both GdUSPIO and amine-GdUSPIO magnetite nanoparticles was confirmed from their XRD pattern. The XRD pattern of both GdUSPIO and amine-GdUSPIO is shown in FIG. 5B. The XRD pattern for both GdUSPIO and amine-GdUSPIO showed similar peaks for the pure phase of magnetite. In addition, the particles do not display sharp diffraction peaks, which are typically observed for amorphous and ultrafine materials. An average. crystalline size of 8.45 nm was calculated using Eq. 1 for both GdUSPIO and amine-GdUSPIO nanoparticles.

Transmission Electron MicroscoDe (TEM)

The particle size and the morphology of both GdUSPIO and amine-GdUSPIO were characterized using TEM. A carbon coated TEM grid (Pelco® No. 160) was used for nanoparticle visualization via a transmission electron microscope (Jeol Transmision Electron Microscopy, JEM-2010, Tokyo, Japan). Briefly, 20 µl of the nanoparticles suspended in water was pipetted on to a carbon-coated grid. The sample was allowed to settle on the grid for approximately 1 minute in a 100 % humidified atmosphere. The carbon-coated grid was then washed with one drop of water, followed by the addition of another 20 µl of the nanoparticles onto the carbon coated grid. The grids were then left for approximately 45 seconds before gently removing excess sample through drying with a filter paper.

Figure 5C:
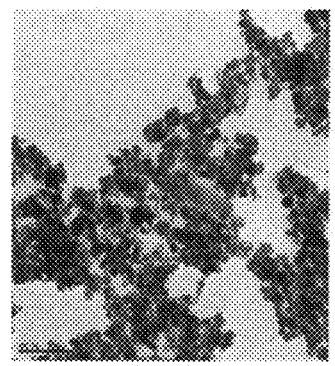
Figure 5D:
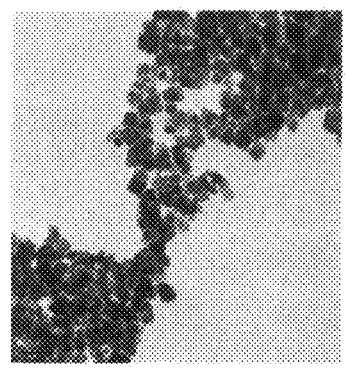

The TEM images of the GdUSPIO and amine-USPIO showed the presence of MNPs having a distinct spheroidal morphology and size. The particle size observed for both GdUSPIO and amine-GdUSPIO was found to be approximately 10-15 nm as shown in FIGS. 5C-5D, respectively. This suggests that modification of the nanoparticles does not affect the overall size and morphology of the nanoparticles. The TEM images also showed the agglomeration of the particles due to the particles being highly magnetic.

Inductively Coupled Plasma-atomic Emission Spectroscopy: (ICP-AES)

The concentration of iron and gadolinium in all samples were measured with an inductively coupled plasma-atomic emission spectrophotometer (ICP-AES) instrument (Thermo, Waltham, Mass.). Briefly, 1.0 mg of the GdUSPIO and amine-GdUSPIO was digested in concentrated HCl for about 45 mins to dissolve. Once the particles were completely dissolved, the HCl was evaporated on a hot plate at 110° C. for 30 mins. The solid nanoparticles were then redissolved by heating with 1.0 mL of concentrated HNO3. Once the sample was dissolved, the solution was diluted 10 times with water to a final concentration of approximately 100 ppm. These solutions were finally used to obtain the ICP-AES data.

Elemental analysis by ICP-AES confirmed the presence of Gd ions in the nanoparticles. The ICP-AES data with respective concentrations in ppm and in moles for Fe, Gd, and Si are tabulated in Table 5. The elemental analysis by ICP-AES also showed the relative Si in the samples. The amount of the Gd in both 4 and 6% doped nanoparticles was found to be approximately 0.4 ppm as compared to 114 and 109.54 ppm of iron, respectively. This suggested that the effective doping of the Gd in 4 and 6% GdUSPIO is approximately 0.1%. Similarly, the amount of the doping in 8 and 10% Gd-doped USPIO was found to be 3.2 and 4.2%, respectively. This also corresponds to the doping efficiency of 42% in 10% GdUSPIO samples.

These discrepancies in the results can be attributed to the lower detection limit of the instrument for the amount of Gd present in the sample. The ICP-AES instrument can measure the Fe concentration in the range of 10-120 ppm, Hence, the samples were prepared considering the maximum concentration of 120 ppm for $Fe^{2+}/Fe^{3+}$ ions. However, this decreased the detection limit for the Gd ions as they were doped starting with the initial ratio of 4 and 6% and the actual doping was lower. Additionally, the molar ratio of the Gd in the sample decreased, as signal-to-noise ratio for the detection of Gd ions in the sample decreased. This led to an inaccuracy in the detection of the Gd at the lower limit. Furthermore, the molar ratio of the amount of the Fe to the amount of the Gd for 10% GdUSPIO was calculated to be 1.56:0.066 as compared to 2.98:0.02 shown before (16). The presence of the Si metal in amine-functionalized samples further confirmed the amine-functionalization of Gd-doped USPIO nanoparticles.

TABLE 5

| Sample | Concentration in ppm | | | Moles | | |
|---|---|---|---|---|---|---|
| | Fe | Si | Gd | Fe | Si | Gd |
| USPIO | 118.20 | 0.00 | 0.00 | 2.11 | 0 | 0 |
| USPIO-amine | 112.78 | 3.83 | 0.00 | 2.019 | 0.13 | 0 |
| 4% Gd USPIO | 114.40 | 0.00 | 0.38 | 2.048 | 0 | 0.002 |
| 4% Gd USPIO-amine | 147.20 | 3.14 | 0.57 | 2.63 | 0.11 | 0.0036 |
| 6% Gd USPIO | 109.54 | 0.00 | 0.41 | 1.96 | 0 | 0.0026 |
| 6% Gd USPIO-amine | 102.70 | 2.68 | 5.85 | 1.83 | 0.095 | 0.037 |
| 8% Gd USPIO | 101.50 | 0.00 | 9.20 | 1.81 | 0 | 0.058 |
| 8% Gd USPIO-amine | 113.14 | 3.06 | 9.38 | 2.02 | 0.10 | 0.059 |
| 10% Gd USPIO | 87.50 | 0.00 | 10.53 | 1.56 | 0 | 0.066 |
| 10% Gd USPIO-amine | 90.72 | 2.92 | 7.72 | 1.62 | 0.10 | 0.049 |

EXAMPLE 3

$USPIO-PEG_{400}-b-Peptide-mPEG_{2000}$
Synthesis of Homobifunctional $COOH-PEG_{400}-COOH$ Diacid The homobifunctional $PEG_{400}$ diacid is synthesized according to the following procedure. Briefly, 20 g of $PEG_{400}$ is dissolved in 300 mL acetone with vigorous stirring in an ice bath. After 15 minutes, 40 mL of Jones reagent (chromium oxide, sulfuric acid, and water) is slowly added and the reaction is stirred for 16 hours. After this time, 20 mL of isopropanol is added to quench the reaction and 2 g of activated carbon is added and stirred for 2 hours. After this time, the reaction mixture is filtered and the solvent is evaporated. The product is obtained from solvent extraction with methylene chloride ($CH_2Cl_2$) and characterized with $^1H$ NMR. FIG. 6A shows that PEG methylene (—$CH_2$) protons, and end methylene (—O—$CH_2$) protons of $PEG_{400}$ are observed at about 1.35 ppm (a), 4.23 ppm (b) and 3.79 ppm (c) with no impurities observed from the spectrum as expected.

Synthesis of heterobifunctional $HOOC-PEG_{400}-NHS$

The homobifunctional $PEG_{400}$ diacid synthesized from the previous step (5 g, 8.96 mmol) is reacted with DCC (3.69 9, 17.8mmol) and NHS (0.896 g, 8.96 mmol) in 100 mL of anhydrous methylene chloride ($CH_2Cl_2$) and the reaction is stirred for 24 hours. The reaction is quenched with ultra-pure $H_2O$, filtered, and concentrated. The unreacted NHS is removed by solvent extraction with benzene and the polymers are precipitated in ether. The product is then column chromatographed to obtain pure heterobifunctional $COOH-PEG_{400}-NHS$. The quantitative analysis of the NHS substitution is determined with $^1H$ NMR, MALDI-TOF and FT-IR.

Synthesis of Blocked Peptides (b-Peptides)

Each of the bioresponsive peptides—ET-1, the RGDS, and the HIV tat peptide are synthesized in tandem with the MMP-13 cleavable sequence, PQGLA, to produce three separate contiguous peptides: GCSCSSLMDKECVYFCHLDIIWG-PQGLAG (SEQ ID NO: 5), GRGDSGPQGLAG (SEQ ID NO: 6), and GYGRKKRRQRRRGPQGLAG (SEQ ID NO: 7), respectively, in which glycines (gly, G) is added as spacer amino acids to increase enzyme recognition of the peptides. These peptides are synthesized using standard fluorenyl-methoxycarbonyl (Fmoc) chemistry on an Applied Biosystems 431A peptide synthesizer (Foster, Calif.). As controls, scrambled peptides are also synthesized and conjugated to nanoparticles in order to demonstrate specificity of the peptides for enzyme cleavage as well as receptor binding and cell penetration.

Figure 6B:
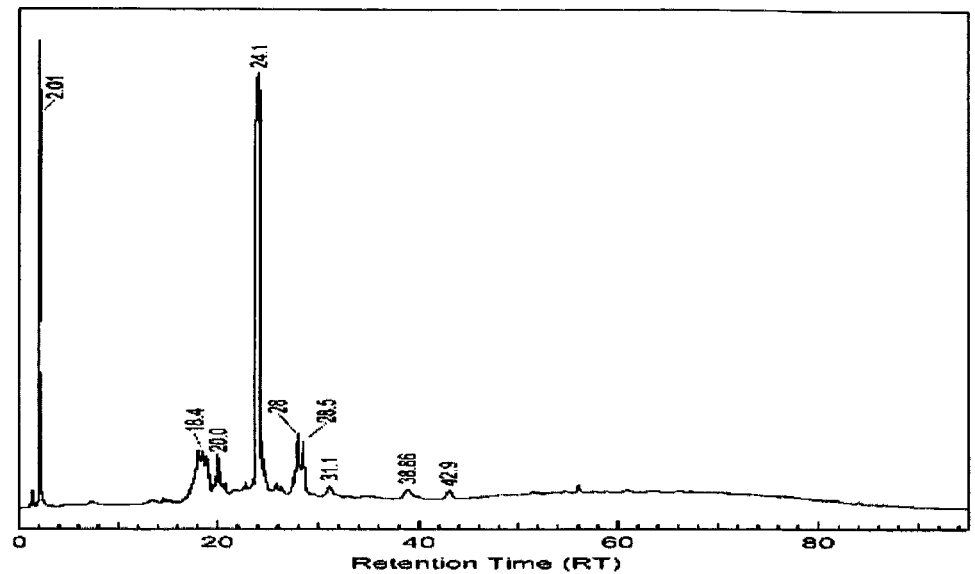
Figure 6C:
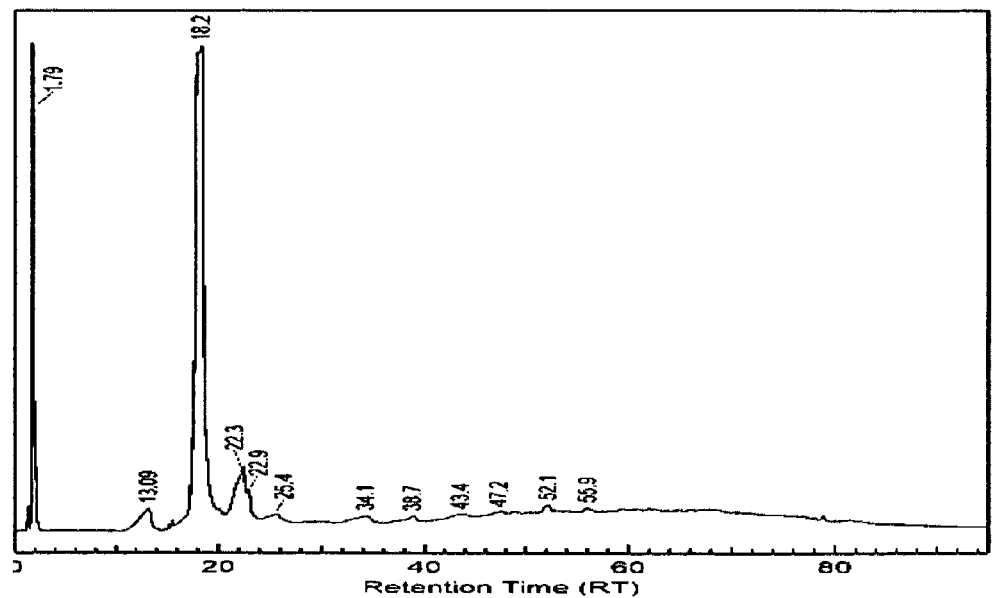

All peptides are synthesized with an ethylene diamine resin on the C-terminus of the peptides (synthesis occurs from the C- to N-terminus), which after cleaving the peptide from the resin introduces an amine group for conjugation to the carboxylate group of the $PEG_{400}$ linker. Moreover, all peptides are synthesized with 'blocked' amino acids in which all reactive side chains of the amino acids are protected. Selective blocking (different blocking groups) and deprotection of the N-terminal glycine facilitates conjugation of the peptide to the outer stealth PEG layer via the N-terminal amine group. After synthesis, the resin of each of the b-peptide is cleaved. Briefly, 800 mg of each peptide is dissolved in 25 mL of 3% trifluoacetic acid in $CH_2Cl_2$ and the reaction mixture is stirred for 4 hours. After this time, the reaction mixture is filtered to remove the cleaved resin. The cleaved peptides are purified with reverse phase high pressure liquid chromatography as shown in FIGS. 6B-6C for GRGDSGPQGLAG (RGDS) containing peptide.

Synthesis of Ultra Small Paramagnetic Iron Oxide-$PEG_{400}$

Each of the synthesized bioresponsive peptides GCSCSS-LMDKECVYFCHLDIIWGPQGLAG, GRGDSG-PQGLAG, and GYGRKKRRQRRRGPQGLAG are conjugated to ultra small paramagnetic iron oxide nanoparticles separately via a short ($PEG_{400}$) linker. Briefly, 1 g of amine-functionalized ultra small paramagnetic iron oxide nanoparticles are dispersed in basic water and stirred for 30 minutes under argon gas. After this time, a 3.0 mole excess of COOH-$PEG_{400}$-NHS is added slowly through an addition funnel and stirred overnight. The reaction mixture is acidified, centrifuged to remove unreacted $PEG_{400}$, and washed with ultrapure water as previously described. The product is characterized for the absence of the amine groups and the presence of $PEG_{400}$ with a ninhydrin assay and FT-IR spectroscopy. These pegylated nanoparticles are then conjugated to the bioresponsive peptides.

Synthesis of Ultra Small Paramagnetic Iron Oxide-$PEG_{400}$-b-Peptide

Briefly, a 3.0 mole excess of RGDS, ET-1, and HIV Tat with MMP-13 cleavable sequence or scrambled peptide sequence of each of the contiguous peptides mentioned above are weighed separately and each are dissolved in 25 mL of $CH_2Cl_2$ and transferred to separate three-neck round bottom flasks purged with argon gas. After about 30 minutes, 0.5 g of the ultra small paramagnetic iron oxide-$PEG_{400}$ nanoparticles are added to each of the reaction solutions, which are then stirred overnight. The reaction mixtures are then washed separately with water and $CH_2Cl_2$ to remove unreacted peptide and each of the different peptide-conjugated nanoparticles are washed with 0.1M HCl to quench the reaction, followed with 0.1M NaOH for neutralization. The $CH_2Cl_2$ is dried with anhydrous $MgSO_4$, filtered, and the solvent is evaporated. The different peptide-conjugated nanoparticles are then characterized with a standard bicinchoninic assay (BCA) as per the manufacturer's instruction to determine the amount of peptides conjugated per nanoparticle.

Synthesis of Stealth Layer: Heterobifunctional COOH-$PEG_{2000}$-OMe

Commercially available monomethoxy-PEG (HO-$PEG_{2000}$-OMe) (MW 2000) is converted to COOH-$PEG_{2000}$-OMe and conjugated to the bioresponsive peptides (from the N-terminus selectively deprotected glycine) to form an inert outer stealth layer that is released upon subsequent cleavage by MMP-13 enzymes in the tumor to reveal a targeting ligand.

Figure 6D:
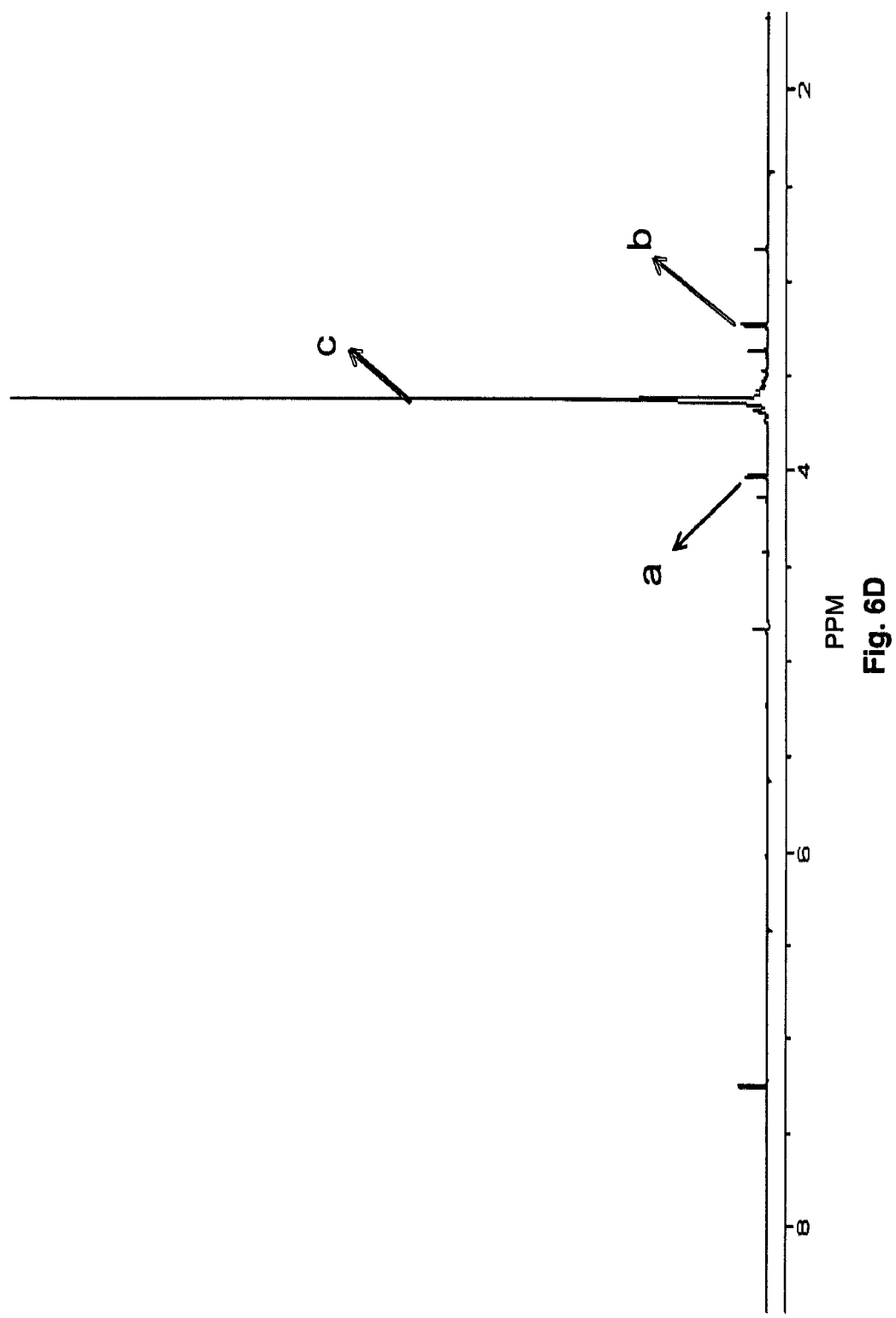

The synthesis of COOH-$PEG_{2000}$-OMe (outer stealth layer) is performed according to the following procedure. Commercially available monomethoxy-PEG (HO-$PEG_{2000}$-OMe) (MW 2000) is converted to COOH-$PEG_{2000}$-OMe and conjugated to the bioresponsive peptides (via N-terminus selectively deprotected glycine) to form an outer stealth layer that is released upon cleavage by MMP-13 enzymes in the tumor to reveal a targeting ligand. This polymer is synthesized and characterized exactly as described above. As can be seen from FIG. 6D, the carboxyl (—COOH), PEG methylene (—CH2) protons, and end methylene (—O—CH2) protons of $PEG_{2000}$ are observed at 4.0 ppm, 3.6 ppm, and 3.3 ppm respectively, with no impurities observed from the spectrum as expected.

Synthesis of Ultra Small Paramagnetic Iron Oxide-$PEG_{400}$-b-Peptide-$mPEG_{2000}$ Briefly, 0.5 g of each different ultra small paramagnetic iron oxide-$PEG_{400}$-b-Peptide nanoparticles are dissolved in 30 mL $CH_2Cl_2$ in separate three-neck round bottom flasks purged with argon gas. After 30 minutes, 25% piperidine in dimethylformamide is added to each reaction mixture that is stirred for 2 hours. After this time, a 3 mole excess of COOH-$PEG_{2000}$-OMe is added to each of the reaction mixture, which is stirred for 4 to 6 hours. The solvent is then evaporated and the products are washed separately to remove unreacted $mPEG_{2000}$. The final biomimetic ultra small paramagnetic iron oxide-$PEG_{400}$-Peptide-$mPEG_{5000}$ nanoparticles are obtained by deprotection of the conjugated peptides. Briefly, 0.5 g of each different ultra small paramagnetic iron oxide-$PEG_{400}$-b-Peptide-$mPEG_{2000}$ nanoparticles are dissolved in 30 ml 50% TFA in $CH_2Cl_2$ in separate three-neck round bottom flasks under argon gas for 3 to 4 hours. After the reaction time, the nanoparticles are filtered from the solvent containing the protecting groups, and the nanoparticles are washed several times with $CH_2Cl_2$. The final nanoparticles are then dried in vacuo. These nanoparticles are characterized with TEM and dynamic light scattering to determine the particle size and hydrodynamic volume respectively.

Quantitative Determination of the T2 Relaxivities

MRI experiment are performed on a 3.0 T horizontal bore General Electric Excite HD imaging system, using the standard 8 channel head coil. Multi-Echo (n=8) Spin-Echo images are obtained for each sample set. The TE values for the echo train are centered around the T2 values determined with a large TR=5000 s to exclude any influence of T1 relaxation effects. The T2 relaxation times are calculated from a linear fit of the logarithmic region-of-interest signal amplitudes versus TE using the Matlab (Mathworks Inc.) software. Relaxivity values aree derived according to equation (1)

$$\frac{1}{T_2} = \frac{1}{T_{20}} + r \cdot c \quad (1)$$

with $T_{20}$ as the T2 value for the agarose gel, r as relaxivity and c as concentration. Statistical analysis (ANOVA and Student's t test) are performed on each data set.

Agarose phantom gels with and without the nanoparticles are prepared and analyzed with an MRI scanner. Agarose gels are used in these studies to simulate the protons present in a tissue environment. The controls for the experiment include agarose gels only and commercially purchased Ferumoxsil® (Mallinckrodt, Inc., Hazelwood, Mo.) with a crystal size of 10 nm.

A set of seven phantoms are built for these studies that contain agarose gels only, agarose gels with Ferumoxsil®, and agarose gels with varying concentrations of the following: synthesized ultra small paramagnetic iron oxide nanoparticles, amine-functionalized ultra small paramagnetic iron oxide nanoparticles, ultra small paramagnetic iron oxide-$PEG_{400}$ nanoparticles, and each of the different ultra small paramagnetic iron oxide-PEG$_{400}$-Peptide nanoparticles, and ultra small paramagnetic iron oxide-PEG$_{400}$-Peptide-PEG$_{2000}$ nanoparticles.

The T$_2$ values for each of the intermediate ultra small paramagnetic iron oxide nanoparticlesm e.g. ultra small paramagnetic iron oxide-PEG$_{400}$, are determined in order to fully characterize the relaxation of the nanoparticles at each modification step. Briefly, Ferumoxsil® and iron oxide nanoparticles at concentrations of 0.001, 0.01, 0.1, 1.0, 10.0, 25.0, 50.0, 75.0, and 100 µg/mL are added to a boiled agarose solution to form a final concentration of 1% agarose gel. The solution is mixed and quickly poured into sterile 15 mL polypropylene tubes that are slowly cooled to room temperature so as to avoid trapping air bubbles inside the tubes. The tubes are then placed in a polystyrene rack that and are secured in a water bath fitted to a MRI head coil.

Figure 6E:
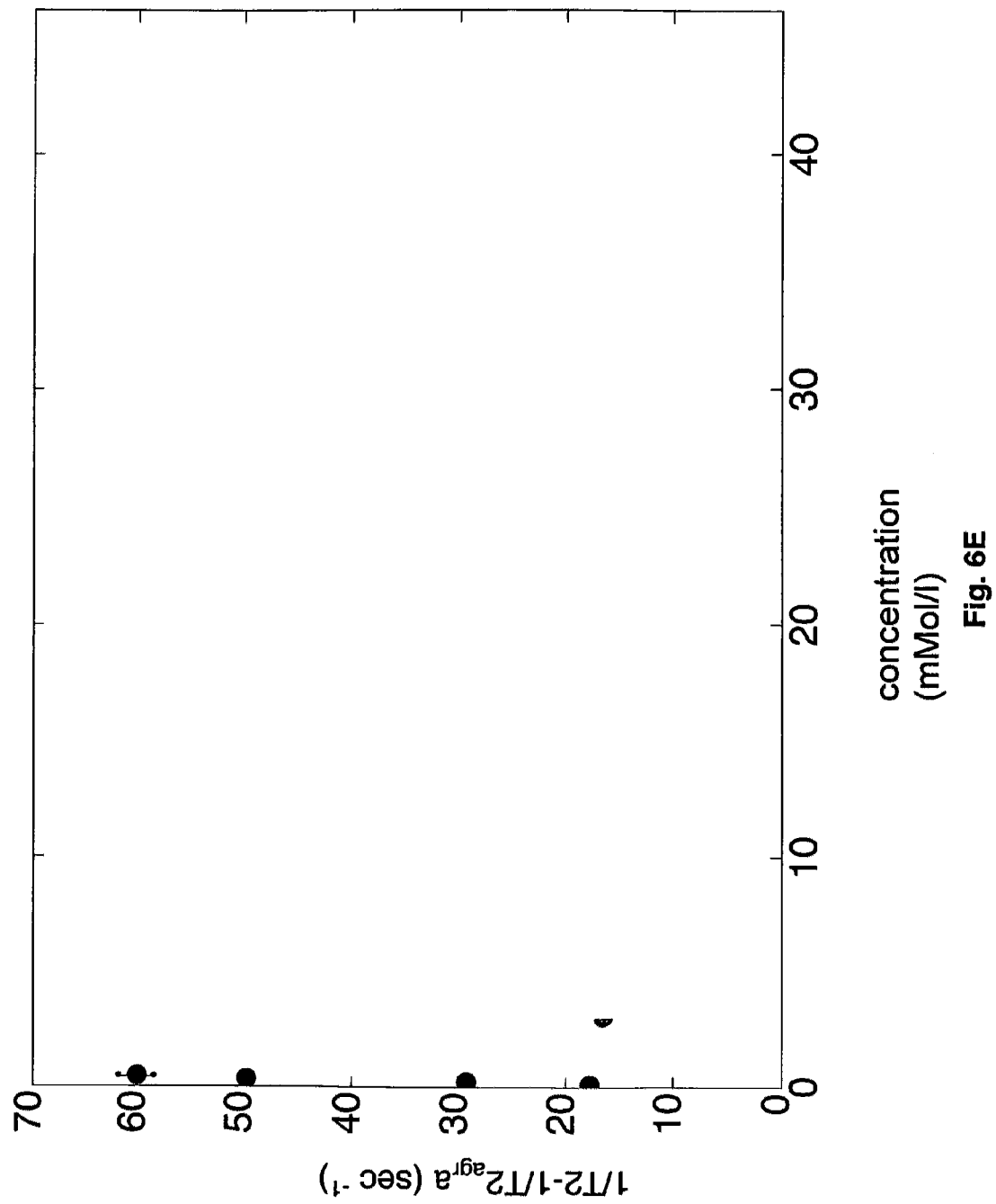

FIG. 6E shows relaxivities values of control ultra small paramagnetic iron oxide nanoparticles, synthesized ultra small paramagnetic iron oxide nanoparticles (130.8 mmol/s), and amine-functionalized ultra small paramagnetic iron oxide nanoparticles (5.5 mmol/s).

The enzymatic degradation of the nanoparticles with MMP-13 (collagenase-3)-labile domains is assessed by monitoring the kinetics of mass loss of the ultra small paramagnetic iron oxide nanoparticles as a function of time and enzyme concentration. The cleavage of the MMP-13 sequence within the nanoparticle results in the release of the outer stealth PEG layer that corresponds to a molecular weight of about 2000 but produces nanoparticles with a smaller hydrodynamic volume. The specificity of the sequence for cleavage via MMP-13 is investigated with the non-specific enzyme elastase.

Release Kinetics of Outer PEG Layer: MMP-13-Dependent Degradation Of Biomimetic USPIO Nanoparticles The three different biomimetic ultra small paramagnetic iron oxide nanoparticles (ET-1, RGDS, HIV Tat) and their corresponding ultra small paramagnetic iron oxide nanoparticles with scrambled peptide sequences are weighed separately and incubated with varying concentrations of MMP-13 or with elastase. Briefly, 100 mg of each iron oxide nanoparticles are added to separate vials each with 1.0 mL of phosphate buffered saline (PBS) with 0.2 mg/mL of sodium azide and 1 mM calcium chloride (CaCl$_2$). Four sets of vials are labeled as 0, 8, and 24 hours and 0.025, 0.0050, and 0.0025 mg/mL (collagenase) and 0.025 mg/mL elastase. Crude collagenase or elastase is then added to the vials to produce the enzyme concentrations listed above. Control samples also include untreated biomimetic ultra small paramagnetic iron oxide nanoparticles. All samples are incubated at 37° C. and at predetermined time intervals stated above samples are removed and analyzed with HPLC, MALDI-TOF, and TEM to determine the molecular weight of the released PEG and the nanoparticle size for both treated and non-treated samples. Statistical analysis (ANOVA and Student's t test) is performed on each data set (N=3). Only nanoparticles containing the correct MMP-13 cleavable sequence are cleaved by the enzymes to release the outer PEG$_{2000}$ layer.

Receptor-Mediated Uptake Of Biomimetic USPIO Nanoparticles with ET-1 and RGDS

Cells (OVCA and HUVECs) are seeded at a density of 9×10$^5$ cells/well in a 6-well plate and incubated at 37° C. for at least 24 hours prior to treatment with nanoparticles. The cells are untreated or treated with plain, bioresponsive, or scrambled nanoparticles at a concentration of 0.03 µmol/mL. In addition, the cells are simultaneously treated with crude collagenase to facilitate the release of the PEG stealth layer. Controls also include cells not treated with the enzyme. After incubation of the cells at predetermined time intervals of 0 hour, 4 hours, 8 hours, and 24 hours, the cells are washed thrice with 1x PBS (0.1 mol/L, pH 7.4) buffer, trypsinized, centrifuged for 5 minutes at 1500 rpm, and counted with a hemocytometer. A total of 7×10$^5$ cells are then mixed with 1% agarose at 37° C. and the T$_2$ relaxation values are measured with MRI. For the competition assay, either free ET-1 or RGDS ligand at a 10,000:1 ratio (ligand:nanoparticles) is used to pretreat the cells prior to the addition of the nanoparticles and T$_2$ values are determined.

Receptor-independent Uptake of Biomimetic Ultra Small Paramagnetic Nanoparticles with HIV Tat Cells (OVCA and HUVECs) are seeded, treated, and analyzed as described above except that the incubation times are performed at 4° C. and 37° C., to demonstrate that uptake of the biomimetic nanoparticles occurs in a receptor-independent manner in which receptor-mediated uptake is inhibited at 4° C.

For Prussian blue staining, cells are plated and treated with plain, bioresponsive, or scrambled nanoparticles as described above except that glass coverslips is placed in the 6-well plates prior to seeding the cells and the cells are incubated for 24 hours. After incubation, the coverslips are washed with PBS and fixed with the organic solvents methanol and acetone. Briefly, the coverslips are added to cooled (−20° C.) in methanol for 10 minutes. The coverslips are then removed from the methanol and the cells are permeabilized with cooled acetone (−20° C.) for 1 minute. The coverslips are then added to 10% potassium ferrocyanide for 5 min and 10% potassium ferrocyanide in 20% hydrochloric acid for 30 minutes, and the nuclei are counterstained by adding the coverslip to a solution of propidium iodide at a concentration of 0.01 mg/mL. The coverslips are then washed thrice with 1×PBS buffer to remove excess propidium iodide and analyzed with microscopy to show uptake of the bioresponsive nanoparticles that are apparent as blue granules.

Cytotoxicity of Biomimetic Ultra Small Paramagnetic Iron Oxide Nanoparticles

Cells (OVCA and HUVECs) are seeded and treated as described above. After the incubation times, the cells are treated with MTT with the method of Mossman. Briefly, the cells are washed with 1×PBS and then incubated with a solution of MTT in 1×PBS buffer at a concentration of 2 mg/mL. The plates are then incubated at 37° C. for 4 hours, after which the medium is removed and 1.0 mL of dimethylsulfoxide is added to the wells to dissolve the formazan crystals. The absorbance of the samples is determined at 570 nm and the readings are normalized to that of the untreated cells.

EXAMPLE 4

USPIO-TEG-Peptide-PEG Contrast Agent

The synthesis of biomimetic USPIO-TEG-Peptide-mPEG$_{5000}$ is depicted in FIGS. 7A-7E.

Synthesis of HO-TEG-Ots 10 gms (0.0255 moles) of TEG was weighed in a 3 neck RBF purged with nitrogen. To the mixture 4.86 gms of Tosyl-chloride was added at 0° C. and the mixture was stirred for 3 hours. At the end of three hours 0.85 mls of TEA was added to neutralize the acid formed and the reaction mixture was left to stir overnight. The progress of the reaction was then monitored by TLC. After the completion of the reaction the solvent was evaporated and the sample was dried under vaccum. The crude product was then chromatographed using ethyl acetate as the solvent. Initial fractions were then left out and the fractions containing pure product were then pooled together and solvent was evaporated and kept in vaccum. Sample obtained was 3.5 gms and NMR showed pure product as shown in FIG. 8A.

Synthesis of HO-TEG-$N_3$ 1.5 gms of HO-TEG-Ots was dissolved in 25-30 mls of DMF followed by the addition of 0.007 gms of sodium azide. The reaction mixture was refluxed and progress of the reaction was monitored by TLC. The TLC showed the formation of the product and the completion of the reaction using 2% methanol in methylene chloride NMR in FIG. 8B shows the presence of the pure product.

Synthesis of $N_3$-TEG-t-butyl Ester 0.047 gms of potassium t-butoxide (M.W: 111.22, 0.425 mmoles) was weighed under nitrogen and transferred to a 50ml round bottom flask containing 10 mls of anhydrous THF purged with $N_2$. After 30 mins, 1 gm of $N_3$O-TEG-OH (0.425 mmoles) was added slowly to the solution using a syringe. Reaction mixture was allowed to react under the nitrogen atmosphere for almost 3-4 hours. After all the solid went into the solution, 0.064 gms t-butyl acrylate( M.W: 128.17, 0.5mmoles) was added slowly to the solution using a syringe. On the addition of t-butyl acrylate the reaction temperature increased and care was taken to maintain at ambient. The reaction mixture was allowed to stir overnight. The progress of the reaction was monitored by TLC. After the completion of the reaction, the solvent was evaporated and the oily residue along with the solid obtained was dissolved in mixture of ethyl acetate and water (50:50) and layers were separated. The reaction mixture was then purified using column chromatography using Ethyl acetate/Hexane as the solvent. Various fractions which seemed similar in TLC were pooled together and the product obtained was characterized by NMR. NMR indicated the presence of pure product (FIG. 8C).

Synthesis of $NH_2$-TEG-t-butyl ester 1.5 gms of $N_3$-TEG-t-butyl ester was weighed under nitrogen and transferred to a 50 ml round bottom flask containing 25 mls of anhydrous THF purged with $N_2$. After 30 mins, 1.2 moles of triphenyl phosphine was added slowly to the reaction mixture. Reaction mixture was allowed to react overnight under the nitrogen atmosphere. The progress of the reaction was monitored by TLC (Methanol/Ethy Acetate 1/10). After the completion of the reaction, the solvent was evaporated and the oily residue was then purified using column chromatography. Various fractions which seemed similar in TLC were pooled together and the product obtained was characterized by NMR. NMR indicated the presence of pure product (FIG. 8D).

Synthesis of HOOC-TEG-t-butyl Ester

Figure 7A:
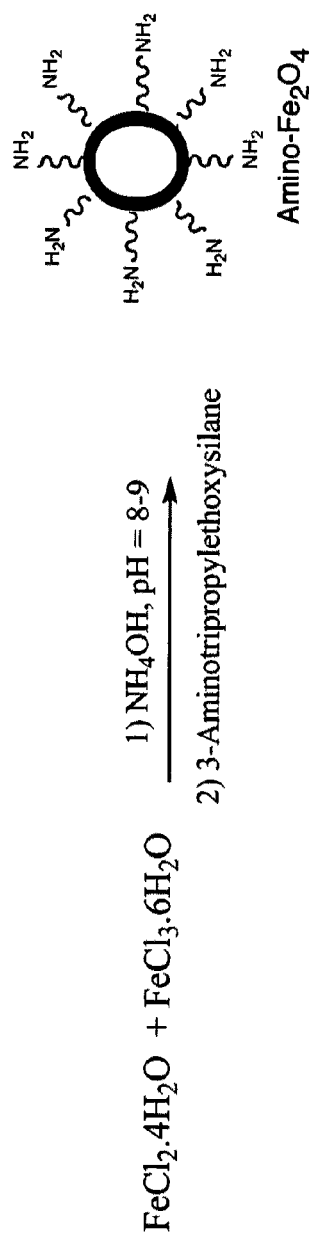
FIGS. 7A-7E depict synthetic schema for amine-functionalized iron oxide nanoparticles (FIG. 7A) HOOC-TEG-t- butyl acrylate synthesis (FIG. 7B), peptide synthesis (FIG. 7C), USPIO-TEG-COOH synthesis (FIG. 7D), and USPIO-TEG-Peptide-mPEG$_{5000}$synthesis (FIG. 7E).
Figure 7B:
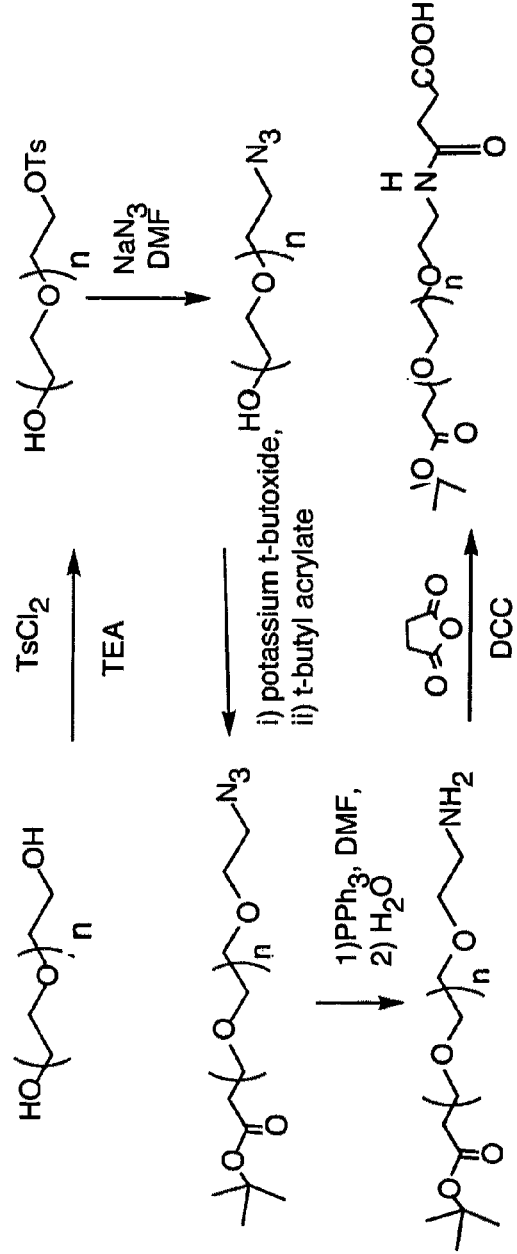

FIG. 7A is the synthetic scheme for amine-functionalized iron oxide nanoparticles. FIG. 7B is the synthetic scheme for HOOC-TEG-t-butyl ester. 1.5 gms of $NH_2$-TEG-t-butyl ester was weighed under nitrogen and transferred to a 50 ml round bottom flask containing 25 mls of anhydrous THF purged with $N_2$. After 30 mins, 1.2 moles of succinic anhydride was added slowly to the reaction mixture. Reaction mixture was allowed to react overnight under the nitrogen atmosphere. The progress of the reaction was monitored by TLC (Methanol/Ethy Acetate 1/10). After the completion of the reaction, the solvent was evaporated and the oily residue was then purified using column chromatography. Various fractions which seemed similar in TLC were pooled together and the product obtained was characterized by NMR. NMR indicated the presence of pure product (FIG. 8E).

Purification of Peptide

Figure 7C:
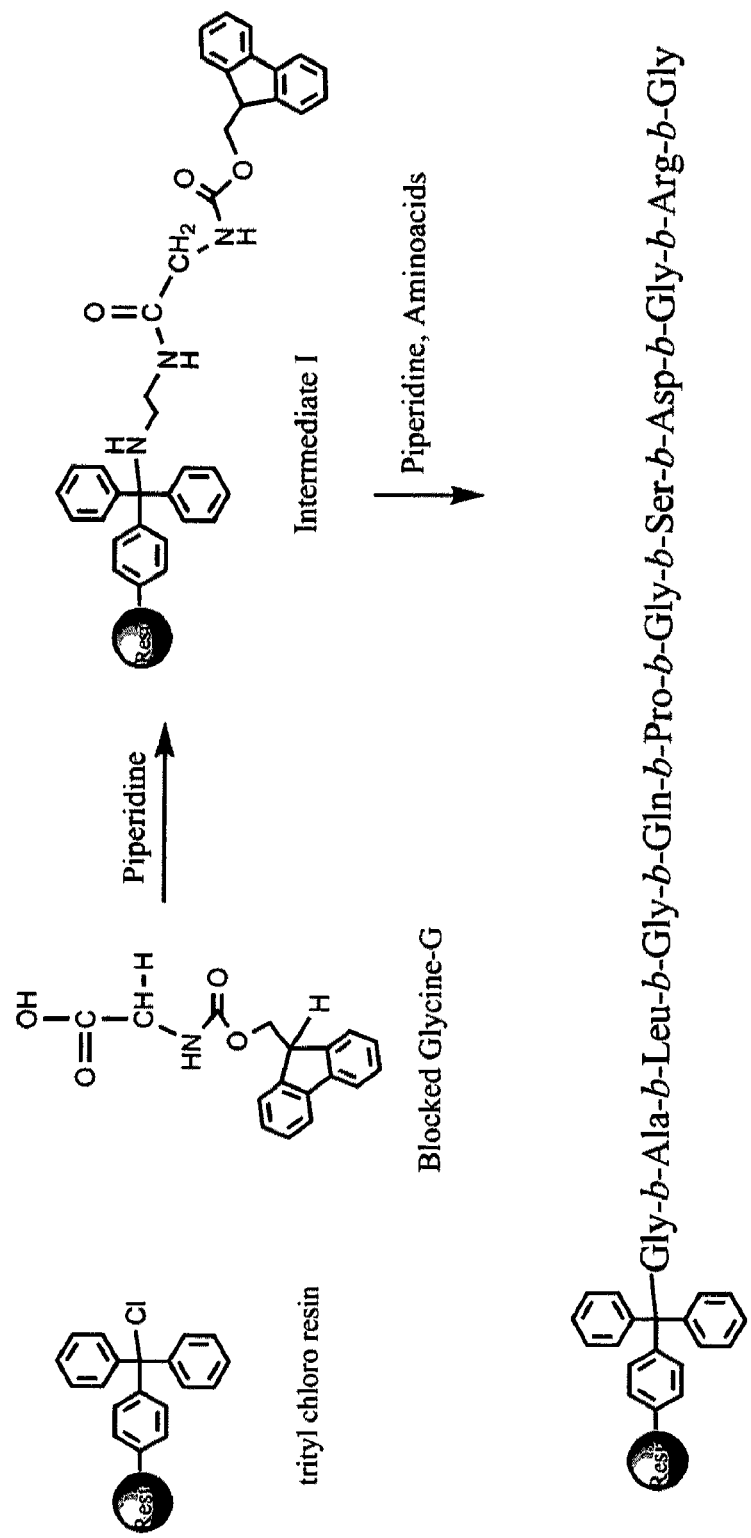

FIG. 7C is the synthetic scheme for peptide synthesis. Peptide was synthesized using solid phase peptide synthesizer on a trityl chloride resin. The purification of peptide was done by recystallization and extraction of the peptide in methylene chloride and water. 10 mg of peptide was dissolved in methylene chloride was extracted with water. This extraction was repeated several times followed by the drying of water using methanol. Once water was dried off the solution was then used for MALDI analysis. The MALDI analysis gave the pure product with minute amount of impurities (FIG. 8F).

Synthesis of USPIO-TEG-t-butyl Ester

30mg of HOOC-TEG-t-butyl ester was mixed with 15.7 mg of EDC in 1 ml of MES buffer and the reaction mixture was heated at 50° C. for about 15-20 mins. This mixture was then added to the suspension of 13 mg of USPIO-amine in 3 mls of water and the reaction mixture was shaken on the shaker for 12 hours. After 12 hours the reaction mixture was centrifuged and washed with water and the solid was separated using magnet and kept in lypholyzer.

Synthesis of USPIO-TEG-Peptide 15 mg of USPIO-TEG t-butyl ester was first hydrolyzed with mixture of methylene chloride and TFA (50:50) for about 2 hours and the solvent was evaporated. After the evaporation of the solvent the sample was kept in lypholyzer for further elemental analysis using EDS. Part of the material (USPIO-TEG) ~15 mg was mixed with 15.7 mg of EDC in 1 ml of MES buffer and the reaction mixture was heated at 50° C. for about 15-20 mins. To this mixture 50 mgs of peptide was then added along with acetonitrile to make the peptide more soluble into the reaction solution. The reaction mixture was shaken on the shaker for 12 hours. After 12 hours the reaction mixture was centrifuged and washed with water and the solid was separated using magnet and kept in lypholyzer.

Figure 7D:
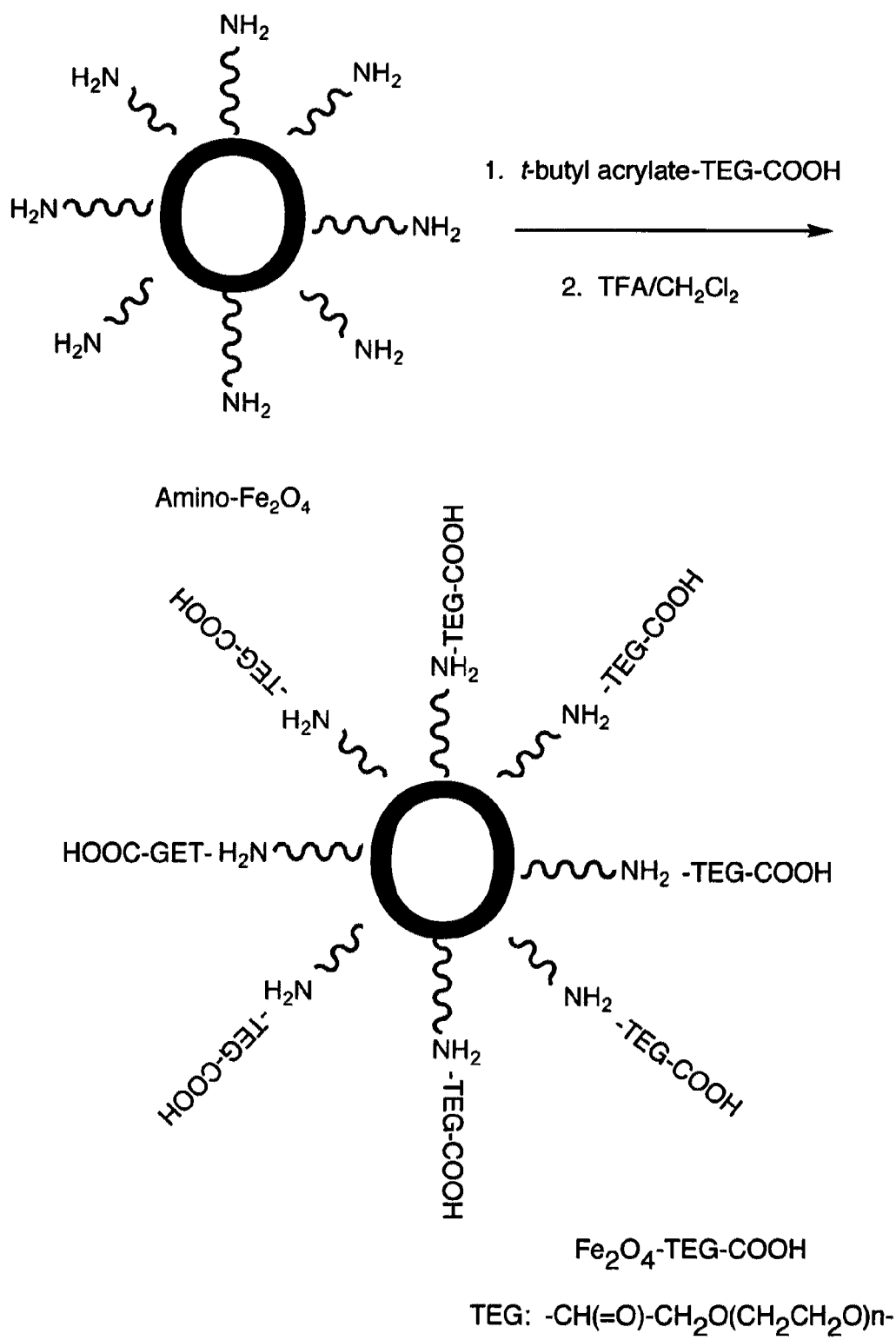
Figure 7E:
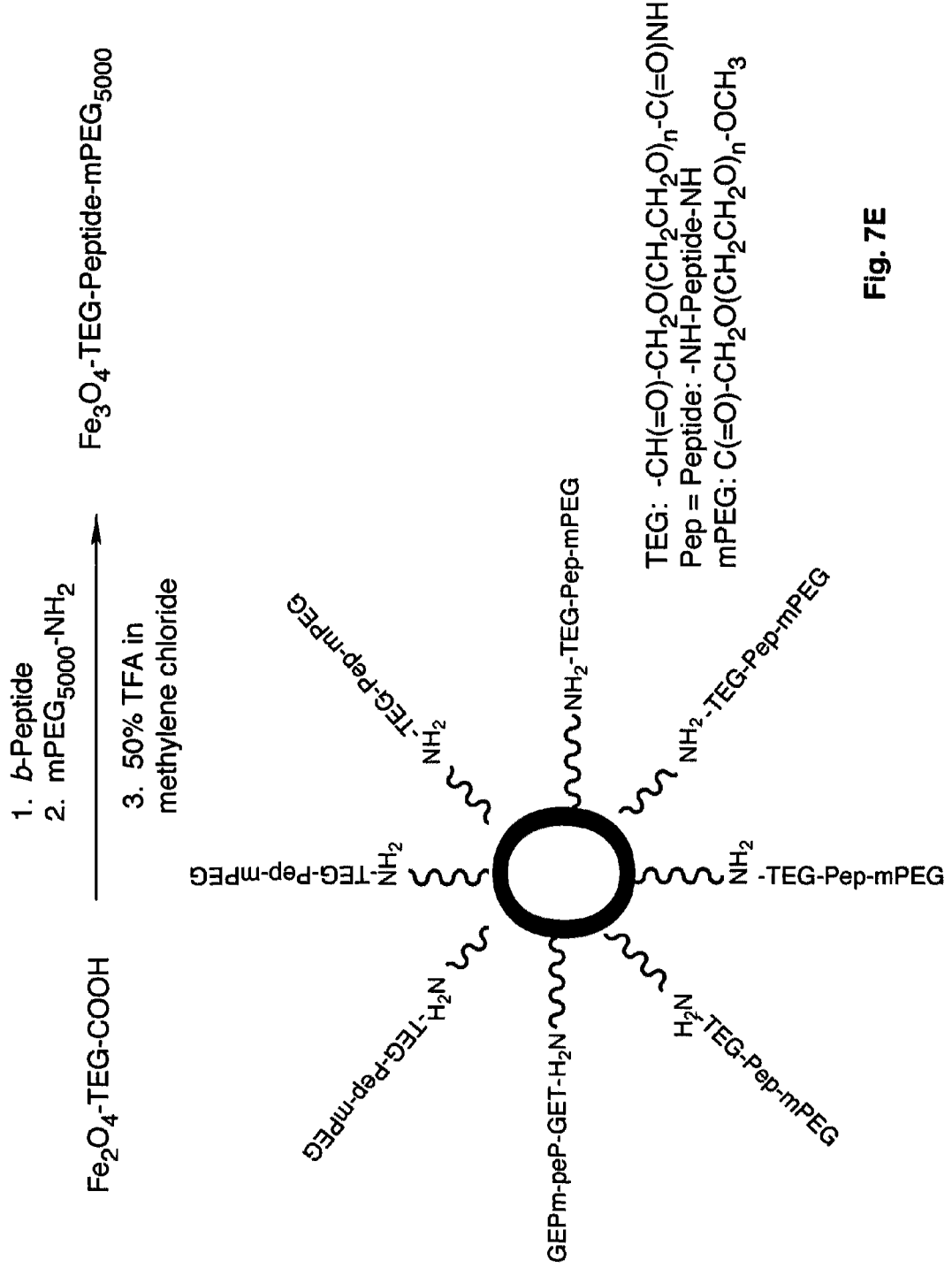

Synthesis of USPIO-TEG-Peptide-mPEG$_{5000}$ 25 mg of USPIO-TEG-peptide was mixed with 23.7 mg of EDC in 1 ml of MES buffer and the reaction mixture was heated at 50° C. for about 15-20 mins. To the reaction mixture 50 mg of PEG-$NH_2$ was then added along with 1 ml of water. The reaction mixture was shaken on the shaker for 12 hours. After 12 hours the reaction mixture was centrifuged and washed with water and the solid was separated using magnet and kept in lypholyzer. Finally the USPIO-TEG-Peptide-PEG was totally deprotected by stirring the in the solution of 1:1 [TFA:$CH_2Cl_2$] for 4 hours. The solvent was evaporated and the product obtained was washed with methylene chloride and reprecipitated using a very powerful magnet while the solution was decanted. This procedure was repeated 3 times so as to make sure that all the impurities are being washed out. FIGS. 7D-7E are synthetic schema for the synthesis of USPIO-TEG-Peptide-mPEG$_{5000}$.

EXAMPLE 5

Dual Functioning Nanoparticles

A dual magnetic resonance imaging (MRI) contrast agent and nonviral gene delivery system comprises iron oxide gadolinium (Gd[III])-doped nanoparticles, coated with an inert layer of gold (Au) are conjugated to a novel biodegradable cationic polymer disulfide-reducible, linear, L-lysine-modified copolymers (LLC). The cationic nanoparticles are transfect mesenchymal stem cells (MSCs) with the IL-12 gene or other anti-tumor gene (FIG. 9).

Synthesis of Functionalized Gold-coated Gd[III]-doped Iron Oxide Nanoparticles

Gd[III]-doped iron oxide ($Fe_3O_4$) nanoparticles are oxidized to $Fe_2O_3$ by boiling in nitric acid ($HNO_3$), and are then coated with gold using a hydroxylamine seedling method with chloroauric acid ($HAuCl_4$). Six different reaction mixtures ranging from 0 to 10% of Gd[III] ions are prepared. As can be seen from the transmission electron microscopy (TEM) image of the 4% Gd-doped nanoparticles in FIG. 10A, the synthesized particles are spheroidal in shape with a particle size of ~7-10 nm. In addition, iron oxide nanoparticles with 0, 2, and 4% Gd[III] ions were analyzed with a 3.0 T Horizontal Bore General Electric Excited HD imaging system to determine if the contrast agents could be detected. As can be seen from FIG. 3, all of the newly synthesized nanoparticles could be detected with MRI (copper sulfate (CuSO4) samples were used as phantom controls) (FIG. 10B). Suspended nanoparticles are reacted with 100 mg of SH-PEG-$NH_2$ with stirring for 12 hr with methods used in our laboratory and purified with a magnet.

Synthesis of Au-Coated Reducible LLC Conjugated Nanoparticles without Ethylenediamine L-lysine HCl and CBA are added to suspended nanoparticles in (80/20 v/v) of methanol/water (MeOH/$H_2O$) with stirring in the dark under nitrogen. Conjugated nanoparticles are purified with a magnet. To investigate the feasibility of the reducible LLC polymers binding DNA, linear copolymers not conjugated to the nanoparticles were synthesized. FIG. 11 shows the $^1H$ NMR of 25% N-boc conjugated polymer with all of the expected peaks of the final product.

Conjugation of N-boc Ethylenediamine to Au-Coated Reducible LLC Nanoparticles

Reducible LLC conjugated Au-coated nanoparticles suspended in water are mixed with a molar excess of 1-ethyl-3-(3-dimethylaminopropyl) carbodiimide hydrochloride (EDC) and N-boc ethylenediamine with stirring in an oil bath at 40° C. in the dark under nitrogen. Conjugated nanoparticles are purified with a magnet. The acid-liable N-boc amine protection group present on the conjugated ethylenediamine are removed with a (TFA)/$H_2O$ mixture (75/25 v/v) trifluoroacetic acid.

Gel Retardation Assay

To evaluate the ability of the conjugated nanoparticles to complex plasmid DNA, a previously published gel retardation assay is performed with a plasmid coding for the luciferase gene (pCMV-Luc). FIG. 12 shows the synthesized LLC polymers were able to successfully condense plasmid DNA from a 25/1 N/P ratios (nitrogens of polymer/phosphates of DNA).

Reduction of Au-coated Reducible LLC Nanoparticles

To a solution of conjugated nanoparticles, 1,4-dithio-DL-threitol (DTT) is added and the solution is incubated at room temperature. The reduction of the disulfide bonds in the cationic polymers is monitored with UV spectroscopy to determine the mechanism of reaction.

Determination of $T_1$ and $T_2$ Relaxations

The longitudinal ($T_1$) and transverse ($T_2$) relaxations of the Au-coated nanoparticles are determined in agarose phantoms. Commercially purchased Ferumoxsil® (Mallinckrodt, Inc., Hazelwood, Mo.) with a crystal size of 10 nm is used as a control.

Transfection Efficiency and Cytotoxicity

Cells are plated and transfected with the contrast agents, i.e., nanoparticles and DNA with luciferase The luciferase assay is performed as previously published. Cells are plated and treated with optimized contrast agents and analyzed with a 3-(4, 5-dimethylthiazol-2-yl)-2, 5-diphenyltetrazolium bromide (MTT) assay for mitochondrial damage and a lactate dehydrogenase assay for cytosolic damage as previously published.

MR Detection of Molecular Probes within Cells

To image MR probes within cells, MSCs treated with the optimized contrast agents are fixed and mixed with an agarose phantom to determine whether or not there are differences in the $T_1$ and $T_2$ values of the nanoplexes following internalization by MSCs on the MRI scanner.

Transwell Migration Studies

The migration of transfected MSCs to plated 4T1 murine metastatic mammary breast cancer cells is studied using cells plated in a transwell cell culture dish. Cells are analyzed with microscopy.

In Vivo Mouse Model

A metastatic mouse model based on 4T1 cells injected subcutaneously in Balb/c mice is established as previously published. MSCs transfected with optimized contrast agents are injected intravenously via the tail vein after tumors have a volume of 75-120 $mm^3$ and lung metastases have been detected. Animals are anesthetized and imaged as a function of time. After this, animals are treated and imaged twice a week for three weeks, blood is sampled and is analyzed for IL-12 expression with an enzyme-linked immunosorbent assay (ELISA). The animals are then sacrificed and tissue sections are obtained for analysis with hematoxylin and eosin.

EXAMPLE 6

Synthesis of Gold Alloy Nanoshells on Gd-Doped $Fe_3O_4$ ($Gd_xFe_{3-x}O_4$) Nanoparticles Synthesis of $Gd_xFe_{3-x}O_4$ and amine functionalized $Gd_xFe_{3-x}O_4$—$NH_2$ Stoichiometic amounts of $FeCl_2.4H_2O$ and $FeCl_3.6H_2O$ were dissolved in 200 mL pure water. The amount of $GdCl_3.xH_2O$ added to the resulting solution was calculated as being x% (x=2, 4, 6, 8 and 10) of the total number of moles of Fe(II) and Fe(III), keeping the molar ratio Fe(III):Fe(II) constant, namely 1:1. The resulting solution was loaded in a 3-neck round bottom flask and purged with Ar for 10 min. In parallel, 100 mL of 1.5 M NaOH (6 g NaOH dissolved in 100 mL pure water) was purged with Ar for 10 min. Afterwards, the NaOH solution was quickly transferred in a funnel which was attached to the 3-neck round bottom flask. The flask was immersed in an oil bath and heated at 65° C. under inert atmosphere (Ar). When the target temperature was reached, the NaOH solution was added drop wise, under continuous stirring, to the solution containing chlorides (light yellow). The final color of the solution was black due to the formation of $Fe_3O_4$ (FIG. 13A). The reaction was carried for 3 hours at 65° C. in inert atmosphere, under vigorous stirring. The black precipitate obtained was centrifuge and washed with pure water three times. The separation from the mother liquid was done by means of a magnet. The resulted samples were stored in the lyophilizer.

$Gd_xFe_{3-x}O_4$ was suspended in a mixture of 100 mL ethanol and 100 mL pure water; the solution was transferred in a 3-neck round bottom flask and flushed with Ar for 10 minutes. The solution was then heated at 60° C. for 15 minutes; the next step was the drop wise addition of 25 mL of $NH_4OH$ (28-30%). After 15 minutes of stirring, 15 mL of 3-aminopropyltriethoxysilane was drop wise added, while stirring. The reaction was carried in inert atmosphere at 60° C. for 3 h. The final solution was centrifuged and the black precipitate washed three times with ethanol and three times with water. The final product was saved in the lyophilizer.

Preparation of Au-seeds Solution (THPC-Au Solution)

1 mL of 0.6 M NaOH, 2 mL of tetrakis(hydroxymethyl) phosphonium chloride (THPC) and 200 mL pure water were mixed and transferred in a 250 mL Erlenmeyer flask. The mixture was vigorously stirred for 30 minutes, to allow formation in situ of formaldehyde (FIG. 13B). After 30 minutes of stirring, 4 mL of 1% $NaAuCl_4.2H_2O$ were quickly added to the flask. The solution became light yellow and after 4-5 seconds dark red. The dark red color is an indication of the formation of the gold nanoparticles with approximately 2 nm in size. The reaction which occurs in solution is a reduction of Au(III) to metallic gold (FIG. 13C). The red solution was stored in refrigerator for at least 3 days prior to be used. The solution has to be used within a week, otherwise a dark red precipitate forms on the bottom of the flask.

Deposition of THPC-Au Seeds on $Gd_xFe_{3-x}O_4$ Nanoparticles ($Gd_xFe_{3-x}O_4$—NH/Au Seeds Nanoparticles)

At least three days old THPC-Au seeds solution was used for the deposition of the gold seeds onto the surface of the $Gd_xFe_{3-x}O_4$—$NH_2$ nanoparticles (FIG. 13D). First, the functionalized magnetic nanoparticles, $Gd_xFe_{3-x}O_4$—$NH_2$, (0.1852 g) were dispersed in 5 mL of pure water and sonicated for 15 minutes. 100 mL of THPC-Au seeds solution was transferred in a 25 mL Erlenmeyer flask. The solution containing the dispersed nanoparticles was added in aliquots of 0.5 mL to the THPC-Au seeds solution, while shaking. The reaction was carried at room temperature while shaking for 15 minutes. Afterwards, the solution was stored overnight in the absence of light. The initial color of the THPC-Au seeds solution was dark red and at the end of the reaction was dark-brown.

Preparation of Ag/Au Alloy Solution 0.025 g $K_2CO_3$ and 100 mL pure water were transferred in a 250 mL Erlenmeyer flask and stirred until completely dissolved. To this solution, 1 mL $AgNO_3$ (1%) and 2 mL $NaAuCl_4.2H_2O$ (1%) were simultaneously added. The solution changed from colorless to milky dark yellow. The reaction was carried for 1 hour under vigorous stirring. The color of the solution at the end of the reaction was clear light yellow.

Deposition of Ag/Au Alloy on $Gd_xFe_{3-x}O_4$—$NH_2$/Au Seeds Nanoparticles 8 mL of Ag/Au alloy solution was transferred in a 25 mL Erlenmeyer flask. In parallel, $Gd_xFe_{3-x}O_4$—$NH_2$/Au seeds nanoparticles were dispersed in 12 mL pure water and sonicated for 30 minutes. Different volumes of this solution (0.2 mL; 0.4 mL; 0.6 mL; 0.8 mL; 1.0 mL; 1.2 mL; 1.4 mL; 1.6 mL; 1.8 mL) were added at room temperature while shaking to the Ag/Au solution while shaking. After 15 minutes of shaking, 0.02 mL formaldehyde and 0.05 mL $NH_4OH$ (28-30%) were simultaneously added. A cluster of Ag/Au alloy, formed from the reduction of Ag(I) and Au(III), should deposit on the surface of Au seeds (FIG. 13E). The mixture was stirred for 30 minutes. UV-Vis spectra were recorded for each sample after 30 minutes, 1 day, 3 days and 5 days of shaking. It was previously observed that the optimum volume of $Gd_xFe_{3-x}O_4$—$NH_2$/Au seeds solution used for the deposition of Ag/Au alloy is 0.5 mL. This was also confirmed by calculations of the optimum concentration of the seeds solution.

X-ray Powder Diffraction of $Fe_3O_4$ and $Gd_xFe_{3-x}O_4$

The samples were ground inside a glove box and loaded on a zero background sample holder. Kapton film was used to protect the samples. The X-ray scan was performed from 5-120° for 18 min/scan using a PanAnalytical diffractometer. As shown in FIG. 14, the incorporation of Gd(III) in the spinel structure of $Fe_3O_4$ occurs, the shift of the peaks towards smaller angle being consistent with an increase of the unit cell as a result of a higher ionic radius of Gd(III) compared to Fe(III) and Fe(II) ($r_{Gd(III)}$=1.053 Å, $r_{Fe(III)}$=0.78 Å, $r_{Fe(II)}$=0.92 Å). However, for 2% Gd-doped $Fe_3O_4$ a decrease of the unit cell is observed (peaks shift towards bigger angles). This might be due to the fact that the samples were analyzed between two repairs of the instrument.

UV-Vis Spectroscopy

All the measurements were performed using THPC-Au seeds solution as background. FIG. 15 is the UV-Vis spectrum of $Gd_xFe_{3-x}O_4$—$NH_2$/Au seeds doped with 10% Gd. Table 6 is a summary of the UV-Vis maximum absorption data for $Gd_xFe_{3-x}O_4$—$NH_2$/Auseeds/AgAu alloy nanoparticles (x=2%, 4%, 6%, 8%, 10% Gd) formed from various reaction times.

TABLE 6

| Sample | Volume of nanoparticles (mL) | Reaction time (time of shaking) | Maximum of absorption (nm) |
|---|---|---|---|
| 2% Gd | 0.2 | 30 min | 686 |
| | 0.2 | 5 days | 710 |
| | 1.0 | 30 min | 610 |
| | 1.0 | 5 days | 720 |
| | 1.8 | 30 min | 655 |
| | 1.8 | 5 days | 664 |
| 4% Gd | 0.2 | 30 min | |
| | 0.2 | 5 days | 720 |
| | 1.0 | 30 min | 676 |
| | 1.0 | 5 days | |
| | 1.8 | 30 min | |
| | 1.8 | 5 days | |
| 6% Gd | 0.2 | 30 min | |
| | 0.2 | 5 days | |
| | 1.0 | 30 min | 720 |
| | 1.0 | 5 days | |
| | 1.8 | 30 min | |
| | 1.8 | 5 days | |
| 8% Gd | 0.2 | 30 min | 653 |
| | 0.2 | 5 days | |
| | 1.0 | 30 min | 616 |
| | 1.0 | 5 days | 682 |
| | 1.8 | 30 min | 642 |
| | 1.8 | 5 days | 627 |
| 10% Gd | 0.2 | 30 min | 625 |
| | 0.2 | 5 days | 682 |
| | 1.0 | 30 min | 623 |
| | 1.0 | 5 days | 635 |
| | 1.8 | 30 min | 610 |
| | 1.8 | 5 days | 659 |

EXAMPLE 7

Synthesis of Gold Alloy Nanoshells on $Fe_3O_4/SiO_2$ Nanoparticles

Synthesis of $Fe_3O_4$ 4.43 g of $FeCl_3.6H_2O$ and 1.625 g of $FeCl_2.4H_2O$ (molar ratio 2:1) were dissolved in 190 mL pure water. The resulting solution was transferred in a 3-neck round bottom flask and purged with Ar for 10 min. In parallel, 10 mL of $NH_4OH$ (25%) was transferred in a funnel which was subsequently attached to the round bottom flask. The drop wise addition of the $NH_4OH$ solution to the solution containing Fe (III) and Fe (II) was done at room temperature under vigorous stirring. While adding the $NH_4OH$, the color of the mixture was dark brown, and at the end of the reaction black, this being an indication of the formation of magnetite, $Fe_3O_4$, according to the reaction shown in FIG. 13A. The reaction was carried for 10 minutes in inert atmosphere, while stirring. The mixture was centrifuged three times; the mother liquid was removed with the help of a magnet. The black precipitate was washed three times with pure water. The final product was stored in the lyophilizer.

Conversion of $Fe_3O_4$ to $\gamma$-$Fe_2O_3$ 3.2770 g of $Fe_3O_4$ obtained as described above, was dispersed in 50 mL of 2M $HNO_3$. The solution was purged with Ar for 15 minutes under vigorous stirring. After 15 minutes, the solution was removed and the precipitate re-dispersed in 50 mL of 2M $HNO_3$ and stirred under Ar flow for another 15 minutes. Afterwards, the black precipitate was stored in the lyophilizer.

Deposition of the Silica ($SiO_2$) Layer 1.0094 g of γ-$Fe_2O_3$ obtained as described above, was dispersed in 60 mL of pure water and sonicated at room temperature for 45 minutes. In parallel, 2.85 mL of tetraethylorthosilicate (TEOS) was diluted with 200 mL ethanol and stirred for 10 minutes. The two solutions (containing γ-$Fe_2O_3$ and TEOS, respectively) were transferred in a round bottom flask and stirred for 10 minutes. Afterwards, a volume of 1.10 mL of triethylamine was drop wise added under continuous stirring to the solution containing γ-$Fe_2O_3$ and TEOS. The reaction was carried for two hours. The mixture was centrifuged three times and the mother liquid separated by means of a magnet. The precipitate was washed three times with water. Final product was stored in the lyophilizer. Preparation of the THPC-Au solution, deposition of the THPC-Au seeds on the $Fe_3O_4$/γ-$Fe_2O_3$ nanoparticles /$SiO_2$ nanoparticles, preparation of Ag/Au alloy solution and deposition of Ag/Au alloy on the $Fe_3O_4$/γ-$Fe_2O_3$ nanoparticles/$SiO_2$/Au seeds nanoparticles were carried out as in Example 6.

X-ray Powder Diffraction of $Fe_3O_4$

The sample preparation was performed as described in Example 6. The reaction time seems to influence the nature of the product (FIG. 16A). Also, FIG. 16B demonstrates that the amorphous structure of $SiO_2$ will not affect the crystalline structure of $Fe_3O_4$/γ-$Fe_2O_3$.

Scanning Electron Microscopy of γ-$Fe_2O_3$/$SiO_2$ Particles

The samples were dispersed in pure water and sonicated for 30 min. The resulted suspensions were drop wise added on copper foils and allowed to evaporate in the oven (~300° C.). FIG. 17 is a SEM micrograph of $Fe_3O_4$ after 10 min reaction time. FIGS. 18A-18B are SEM micrographs of γ-$Fe_2O_3$/$SiO_2$ particles.

EXAMPLE 8

Synthesis of Gold Alloy Nanoshells on Ru-Doped $Fe_3O_4$ ($Ru_xFe_{3-x}O_4$) Nanoarticles Synthesis of $Ru_xFe_{3-x}O_4$—$NH_2$/Au Seeds Nanoparticles $FeCl_2.4H_2O$, $FeCl_3.6H_2O$, $RuCl_3xH_2O$ and 3-aminopropyltriethoxysilane are used to synthesize $RuxFe_{3-x}O_4$ and functionalize it to $RuxFe_{3-x}O_4$—$NH_2$ by the methods described in Example 6. Preparation of the THPC-Au solution, deposition of the THPC-Au seeds on the $RuxFe_{3-x}O_4$ nanoparticles, preparation of the Ag/Au alloy solution and deposition of Ag/Au alloy on the $Ru_xFe_{3-x}O_4$—$NH_2$/Au seeds nanoparticles were carried out as in Example 6.

X-ray Powder Diffraction of $Fe_3O_4$ and $Ru_xFe_{3-x}O_4$

The sample preparation was performed as described in Example 6. As shown in FIG. 19, the incorporation of Ru(III) in the spinel structure of $Fe_3O_4$ occurs. However, the shift of the peaks is not consistent. For 2% a decrease in the unit cell is observed, while for 4 and 8% an increase of the unit cell is observed. This is consistent with the increase of the ionic radius of Ru(III) ($r_{Ru(III)}$=0.68 Å, rFe(III)=0.645 Å).

Scanning Electron Microscopy of $Ru_xFe_{3-x}O_4$ (x=2-8%)

The sample preparation was performed as described in Example 7. FIGS. 20A-20H are SEM micrographs of 2%, 4%, 6%, and 8% Ru-doped $Fe_{3-x}O_4$. Table 7 presents semi quantitative analysis data by means of SEM/EDS for $Ru_xFe_{3-x}O_4$.

TABLE 7

| Sample | SEM/EDS results |
| --- | --- |
| $Ru_xFe_{3-x}O_4$ (x = 2%) | 42.45% O; Fe 56.11%; Ru 1.43% |
| $Ru_xFe_{3-x}O_4$—$NH_2$ (x = 2%) | 38.55% O; 47.89% Fe; 10.15% N; 3.35% Si |
| $Ru_xFe_{3-x}O_4$—$NH_2$/Au seeds (x = 2%) | ND |
| $Ru_xFe_{3-x}O_4$ (x = 4%) | 44.18% O; Fe 54.73%; Ru 1.08% |
| $Ru_xFe_{3-x}O_4$—$NH_2$ (x = 4%) | 40.05% O; 32.49% Fe; 0.62% Ru; 22.54% N; 4.28% Si |
| $Ru_xFe_{3-x}O_4$—$NH_2$/Au seeds (x = 4%) | ND |
| $Ru_xFe_{3-x}O_4$ (x = 6%) | 58.98% O; Fe 39.02%; Ru 1.98% |
| $Ru_xFe_{3-x}O_4$—$NH_2$ (x = 6%) | 40.58% O; 30.15% Fe; 0.97% Ru; 24.61% N; 3.68% Si |
| $Ru_xFe_{3-x}O_4$—$NH_2$/Au seeds (x = 6%) | ND |
| $Ru_xFe_{3-x}O_4$ (x = 8%) | 48.65% O; 50.16% Fe; 1.77% Ru |
| $Ru_xFe_{3-x}O_4$—$NH_2$ (x = 8%) | ND |
| $Ru_xFe_{3-x}O_4$—$NH_2$/Au seeds (x = 8%) | ND |
| $Ru_xFe_{3-x}O_4$ (x = 10%) | ND |
| $Ru_xFe_{3-x}O_4$—$NH_2$ (x = 10%) | ND |
| $Ru_xFe_{3-x}O_4$—$NH_2$/Au seeds (x = 10%) | ND |

UV-Vis Spectroscopy

All the measurements were performed using pure water as background. FIG. 21A is a comparison of UV-Vis spectra of $Ru_xFe_{3-x}O_4$—$NH_2$ nanoparticles with Ru doping at 2%-10% before and after deposition of the Au-seeds. Maximum absorption with 2% Ru doping is 643 nm, with 4% Ru doping is 627 nm and with 10% Ru doping is 620 nm. FIG. 21B is UV-Vis spectrum of $Ru_xFe_{3-x}O_4$—$NH_2$/Au seeds (x=8%) using a THPC-Au seeds solution (0.5 mL) as background. Table 8 is a summary of the UV-Vis absorbance data for $Ru_xFe_{3-x}O_4$—$NH_2$/Au seeds/AgAu alloy nanoparticles.

TABLE 8

| Sample | Volume of nanoparticles (mL) | Reaction time (time of shaking) | Max. of Abs (nm) |
| --- | --- | --- | --- |
| 2% Ru | 0.5 | 30 min before washing and centrifuge (w, c) | 586 |
|  | 1.0 | 30 min before w, c | 544 |
|  | 1.5 | 30 min before w, c | 540 |
| 4% Ru | 0.5 | 30 min before w, c | 610 |
|  | 1.0 | 30 min before w, c | 611 |
|  | 1.5 | 30 min before w, c | 669 |

The following references were cited herein:
1. Young Soo Kang et al. Chem. Mater, 8:2209-2211,1996.
2. Cozzoli et al. Chem Soc Rev, 35(11):195-208, 2006.
3. Pankhurst et al. J. Phys. D: Appl. Phys. 36:R167, 2003.
4. West, J. L. and Halas, N. J. Curr Opin Biotechnol, 11(2): 215-7, 2000.
5. Yu et al. IEEE Transactions on Magnetics, 43(6):2436-2438, 2007.
6. Yabin Sun et al., Chem. Commun., 2006:2765 - 2767, 2006.
7. Dodson, J. Gene Ther, 13:283-287, 2006.
8. Rudge et al. J. Controlled Release, 2001 (74):335-340, 2001.
9. Mah et al., Mol. Ther. 6:106, 2002.
10. Ito et al. J. Biosci. Bioeng, 1:100, 2005.
11. Osaka et al. Anal. Bioanal. Chem, 384:593, 2006.
12. Dobson, J., Gene Ther 13:283, 2006.
13. Wang Y X, H. S., Krestin G P, Eur Radiol, 11:2319-2331, 2001.
14. Pilgrimm, H., 2003, USA, 6638494

15. LaConte et al. Journal of Magnetic Resonance Imaging, 26:1634-1641, 2007.
16. Drake et al. Journal of Material Chemistry, 17:4914-4918, 2007.
17. Hong et al. Chemistry Letters, 33(11):1468-1469, 2004.

Any patents or publications mentioned in this specification are indicative of the levels of those skilled in the art to which the invention pertains. Further, these patents and publications are incorporated by reference herein to the same extent as if each individual publication was specifically and individually indicated to be incorporated by reference.

One skilled in the art will appreciate readily that the present invention is well adapted to carry out the objects and obtain the ends and advantages mentioned, as well as those objects, ends and advantages inherent herein. Changes therein and other uses which are encompassed within the spirit of the invention as defined by the scope of the claims will occur to those skilled in the art.

What is claimed is:

1. A magnetic nanoparticle, comprising:
   a functionalized inner core comprising iron oxide, wherein said inner core is functionalized with a silica layer;
   an inert metal seeding the functionalized core; and
   an outer inert metal alloy nanoshell.

2. The magnetic nanoparticle of claim 1, further comprising a metal doping agent in the nanoparticle core.

3. The magnetic nanoparticle of claim 2, wherein the metal doping agent is gadolinium, manganese, cobalt, or ruthenium.

4. The magnetic nanoparticle of claim 2, wherein the metal doping agent comprises about 2% to about 10% of the iron oxide core.

5. The magnetic nanoparticle of claim 1, further comprising a targeting ligand attached to the nanoshell via a linker.

6. The magnetic nanoparticle of claim 5, wherein the linker comprises a triethylene glycol polymer or a polyethylene glycol polymer.

7. The magnetic nanoparticle of claim 5, further comprising an inert outer layer of a hydrophilic polymer conjugated to the targeting ligand.

8. The magnetic nanoparticle of claim 1, wherein the inert seeding metal is gold.

9. The magnetic nanoparticle of claim 1, wherein the inert metal alloy nanoshell is a gold-silver alloy nanoshell.

10. A kit comprising the magnetic nanoparticles of claim 1.

11. A magnetic nanoparticle, comprising:
    an amine-functionalized metal-doped iron(III) oxide core;
    a layer of gold seeding on the amine-functionalized metal-doped iron oxide core; an outer gold-silver alloy nanoshell;
    and a targeting ligand attached to the nanoshell via a linker.

12. The magnetic nanoparticle of claim 11, wherein the linker comprises a triethylene glycol polymer or a polyethylene glycol polymer.

13. The magnetic nanoparticle of claim 11, wherein the iron(III) oxide core is doped with gadolinium or ruthenium.

14. The magnetic nanoparticle of claim 13, wherein the gadolinium or the ruthenium comprise about 2% to about 10% of the iron oxide core.

15. A magnetic nanoparticle, comprising:
    an iron(III) oxide/iron(II) core;
    a layer of silica around the core;
    an outer gold-silver alloy nanoshell; and
    a targeting ligand attached to the nanoshell via a linker.

16. The magnetic nanoparticle of claim 15, wherein the linker comprises a triethylene glycol polymer or a polyethylene glycol polymer.

17. The magnetic nanoparticle of claim 15, further comprising an inert outer layer of a hydrophilic polymer conjugated to the targeting ligand.

* * * * *